US012674209B2

(12) United States Patent
Gupta et al.

(10) Patent No.: US 12,674,209 B2
(45) Date of Patent: Jul. 7, 2026

(54) COMPOSITIONS AND METHODS FOR THE SELECTIVE DETECTION OF TUMOR-DERIVED VIRAL DNA

(71) Applicant: THE UNIVERSITY OF NORTH CAROLINA AT CHAPEL HILL, Chapel Hill, NC (US)

(72) Inventors: Gaorav Gupta, Chapel Hill, NC (US); Bhishamjit S. Chera, Chapel Hill, NC (US); Sunil Kumar, Chapel Hill, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 874 days.

(21) Appl. No.: 17/906,032

(22) PCT Filed: Mar. 16, 2021

(86) PCT No.: PCT/US2021/022568
§ 371 (c)(1),
(2) Date: Sep. 9, 2022

(87) PCT Pub. No.: WO2021/188540
PCT Pub. Date: Sep. 23, 2021

(65) Prior Publication Data
US 2023/0103645 A1      Apr. 6, 2023

Related U.S. Application Data

(60) Provisional application No. 62/990,438, filed on Mar. 16, 2020.

(51) Int. Cl.
| | |
|---|---|
| *C12Q 1/68* | (2018.01) |
| *C12Q 1/6853* | (2018.01) |
| *C12Q 1/686* | (2018.01) |
| *C12Q 1/6888* | (2018.01) |
| *C12Q 1/70* | (2006.01) |

(52) U.S. Cl.
CPC ......... *C12Q 1/6888* (2013.01); *C12Q 1/6853* (2013.01); *C12Q 1/686* (2013.01); *C12Q 1/70* (2013.01); *C12Q 1/701* (2013.01); *C12Q 1/708* (2013.01)

(58) Field of Classification Search
None
See application file for complete search history.

(56) References Cited

U.S. PATENT DOCUMENTS

2018/0223338 A1      8/2018   Guerrero-Preston et al.

FOREIGN PATENT DOCUMENTS

| | | |
|---|---|---|
| CN | 103276105 A | 9/2013 |
| CN | 110042110 A | 7/2019 |
| CN | 110592279 A | 12/2019 |
| EP | 0402132 A2 | 12/1990 |
| KR | 20040006988 A | 1/2004 |

OTHER PUBLICATIONS

European Search Report, European Application No. 21771671.1, issued Mar. 26, 2024.
International Search Report and Written Opinion, International Patent Application No. PCT/US2021/022568, mailed Sep. 10, 2021.
Chera, Bhishamjit S., et al., "Plasma Circluating Tumor HPV DNA for the Surveillance of Cancer Recurrence in HPV-Associated Oropharyngeal Cancer," Journal of Clinical Oncology, vol. 38, No. 10 (2020) (11 pages).
GenBank submission KY306735.1, Human papillomavirus type 16 isolate PB27 ES gene, Oct. 30, 2017, https://www.ncbi.nlm.nih.gov/nuccore/KY306735, retrieved from internet on Aug. 1, 2021.
GenBank submission MF191636.1, Human papillomavirus type 16 strain MML14 E6 oncoprotein (E6) gene, partial cds, Sep. 30, 2017, https://ncbi.nlm.nih.gov/nuccore/MF191636, retrieved from internet on Aug. 1, 2021.
GenBank submission AY192155.1, Synthetic construct Human papillomavirus E7d peptide gene, partial cds, Jul. 25, 2016, https://www.ncbi.nlm.nih.gov/nuccore/AY192155, retrieved from internet on Aug. 1, 2021.
GenBank submission KP313777, 1 Human papillomavirus type 16 isolate HPV16E7/CongoBZV/2014/AM5 E7 protein (E7) gene, partial cs, Jun. 2, 2015, retrieved on Aug. 1, 2021.
GenBank submission KT, Human papillomavirus type isolate a E7 protein gene, partial cds, Mar. 28, 2016, https://www.ncbi.nlm.nih.gov/nuccore/KT943723, retrieved on Aug. 1, 2021.
Moustafa, Ahmed, et al., "The blood DNA virome in 8,000 humans," PLOS Pathogens, vol. 13, No. 3 (2017) (20 pages).
Bodaghi, Sohrab, et al., "Could Human Papillomaviruses be Spread through Blood?" Journal of Clinical Microbiology, vol. 43, No. 11 (2005), pp. 5428-5434.
Cocuzza, Clementina Elvezia, et al., "Human papillomavirus DNA detection in plasma and cervical samples of women with a recent history of low grade of precancerous cervical dysplasia," PLOS One, vol. 12, No. 11 (2017) (11 pages).
Ferreira, Ligia Lavezo, et al., "Plasma HPV DNA is detectable in oral leukoplakia patients," Pathology—Research and Practice, vol. 213 (2017), pp. 759-765.
Chen, Alice Che-Ha, et al., "Human Papillomavirus DNA Detected in Peripheral Blood Samples From Healthy Australian Male Blood Donors," Journal of Medical Virology, vol. 81 (2009), pp. 1792-1796.

(Continued)

*Primary Examiner* — Juliet C Switzer
(74) *Attorney, Agent, or Firm* — Thomas|Horstemeyer, LLP

(57)      ABSTRACT

The present disclosure provides methods and compositions of modified oligonucleotide primer and probe combinations, structurally modified with locked nucleic acids, quenchers, and dyes, effective to detect tumor-derived Human Papilloma Virus (HPV) and tumor-derived Epstein-Barr virus (EBV) and, especially, to distinguish viral DNA derived from tumors from viral DNA derived from infectious viral particles.

5 Claims, 15 Drawing Sheets

Specification includes a Sequence Listing.

(56) References Cited

OTHER PUBLICATIONS

Jensen, K.K., et al., "Circulating human papillomavirus DNA as a surveillance tool in head and neck squamous cell carcinoma: A systematic review and meta-analysis," Clinical Otolaryngology, vol. 43 (2018), pp. 1242-1249.

Higginson, D.S., et al., "Use of Human Papillomavirus 16 (HPV16) Cell Free DNA for Assessment of Response to Chemoradiation in HPV-Associated Oropharyngeal Cancer," Oral Scientific Sessions, vol. 93, No. 3S (2015), pp. S79-S80.

Cao, Hongbin, et al., "Quantitation of the Human Papillomavirus DNA in the Plasma of Patients with Oropharyngeal Carcinoma," Int. J. Radiat. Oncol. Biol. Phys., vol. 82, No. 3 (2012), pp. 351-358.

Dahlstrom, Kristina R., et al., "Circulating HPV DNA as a marker for disease extent and recurrence among patients with oropharyngeal cancer," Cancer, vol. 121, No. 19 (2015), pp. 3455-3464.

Hindson, Benjamin J., et al., "High-Throughput Droplet Digital PCR System for Absolute Quantitation of DNA Copy Number," Anal. Chem., vol. 83 (2011), pp. 8604-8610.

Pinheiro, Leonardo B., et al., "Evaluation of a Droplet Digital Polymerase Chain Reaction Format for DNA Copy Number Quantification," Anal. Chem., vol. 84 (2012), pp. 1003-1011.

Chinese Office Action for Application No. 202180030331.8, dated Jan. 9, 2026, 14 pages (Search Report Included with Translation).

13 of 73 patients in remission tested positive for blood test:

- None clinically symptomatic at the time of the test
- Imaging scans show 9/13 patients have recurrence
- Closely following remaining 4/13 for recurrence

Case study from blood test clinical trial

COMPOSITIONS AND METHODS FOR THE SELECTIVE DETECTION OF TUMOR-DERIVED VIRAL DNA

CROSS REFERENCE TO RELATED APPLICATION

This application claims priority from U.S. Provisional Application Ser. No. 62/990,438, filed on Mar. 16, 2020, which is incorporated herein by reference in its entirety.

FIELD

This disclosure relates to detecting viral nucleic acids in bodily fluids for the purpose of cancer or pre-cancer detection.

BACKGROUND

Viruses are known to promote the development of cancers. For example, infection with high-risk strains of Human Papillomavirus (HPV) is associated with cancers of the cervix, head/neck, anus, vulva, or penis. Other examples of viruses associated with cancer development include Hepatitis B Virus (HBV), Hepatitis C Virus (HCV), Human T-Lymphotropic Virus 1 (HTLV1), Epstein-Barr Virus (EBV), Cytomegalovirus (CMV), Human Endogenous Retrovirus type K (HERV-K), Merkel Cell Virus, Human Immunodeficiency Virus (HIV), and Kaposi's Sarcoma Herpes Virus (KSHV). Since circulating tumor DNA (ctDNA) is released by dying cancer cells, these viral nucleic acids may be detectable in the blood of patients with the corresponding cancer type.

While there is significant interest in detecting viral nucleic acids in bodily fluids for the purpose of cancer detection, there are two major challenges associated with this concept. First, the amount of circulating tumor-derived DNA (ctDNA) in blood, urine or saliva is extremely low—often on the order of a few molecules per mL of blood. Second, viral nucleic acids present in the circulation are commonly not derived from tumor-associated viruses, but from virions shed from non-tumor tissues. This is established by the finding that DNA sequences from many different types of viruses have been identified in the blood of healthy volunteers (Moustafa et al., PLoS Pathog. 2017 13 (3): e1006292). Given this finding, the detection of viral sequences in the circulation is, on its own, insufficient to conclude that a patient has a cancer associated with that virus, since the detected viral sequence may well be derived from normal, non-tumor tissues within the patient.

For example, any viral sequence detected in a blood sample could be associated merely with the viral infection itself and have no relationship to tumor burden in the host. This major confounding factor poses a significant challenge to using circulating viral DNA as a specific marker for cancer detection. Individuals with detectable viral DNA in the circulation could merely be infected with the virus and not have a cancer or pre-cancer.

Consistent with this, PCR-based methods have been reported for detecting HPV DNA in the circulation of patients with HPV-associated preneoplasia or cancers, but these methods also detect HPV DNA in the blood of a substantial proportion of patients who do not have a diagnosis of HPV+ cancer (Bodaghi et al., J Clin Microbiol. 2005 43(11):5428-5434; Cocuzza et al., PLoS One. 2017 12 (11): e0188592; Ferreira et al., Pathol Res Pract. 2017 213(7):759-765; Chen et al., J Med Virol. 2009 81(10):1792-

1796). Thus, since the presence of HPV virus in the circulation of a person could be due to infection of normal tissues, its detection does not necessarily indicate that a person has an HPV-associated cancer. Because currently available PCR detection methods are unable to distinguish between tumor-derived HPV DNA and HPV DNA deriving from normal tissue infected with the virus, they lack sufficient specificity to allow early detection of HPV-associated cancers.

For example, PCR-based methods for HPV detection have demonstrated a sensitivity of only about 54% to detect patients with HPV-associated cancers, which is insufficient to be clinically useful to distinguish patients who need further evaluation from those who do not need further evaluation (Jensen et al., Clin Otolaryngol. 2018 May 15; Higginson et al., Int J Radiat Oncol Biol Phys. 2015 93 (3): S78-S-79; Cao et al., Int J Radiat Oncol Biol Phys. 2012 82 (3): e351-358; Dahlstrom et al., Cancer. 2015 121(19):3455-3464).

SUMMARY

The present disclosure provides methods and compositions of DNA oligonucleotide primer and probe combinations, structurally modified with locked nucleic acids, quenchers, and dyes, effective to detect tumor-derived viral, e.g., HPV and EBV, DNA and, especially, to distinguish viral DNA derived from tumors from viral DNA derived from infectious viral particles.

The DNA amplification methods and structurally modified primer/probe compositions disclosed herein quantitatively detect tumor-derived viral DNA in a sample. The disclosed methods and compositions distinguish between viral DNA derived from tumors and viral DNA derived from non-tumor sources, e.g., from infectious viral particles. In particular, disclosed herein are methods and compositions of detecting or monitoring a human papilloma virus (HPV)-associated malignancy or Epstein-Barr virus (EBV)-associated malignancy in a subject, wherein the methods involve detecting a presence or absence of at least one circulating tumor-derived HPV or EBV DNA of a particular size range in a sample from the subject. Compositions and kits for conducting these methods are also provided.

In one aspect, the disclosure provides compositions for detecting tumor-derived Human Papilloma Virus type 16 (HPV16), HPV18, HPV31, HPV33, HPV35, or HPV45 in a sample from a subject, wherein a composition includes at least (or consists of) a triad, e.g., three, or can include four, five, six, seven, eight, nine, ten, or more, of modified oligonucleotide primer/probe sets selected from: primer/probe sets numbered 1 to 18 as shown in Table 14 for HPV16, primer/probe sets numbered 1 to 18 as shown in Table 15 for HPV18, primer/probe sets numbered 1 to 17 as shown in Table 16 for HPV31, primer/probe sets numbered 1 to 15 as shown in Table 17 for HPV33, primer/probe sets numbered 1 to 16 as shown in Table 18, for HPV35 or primer/probe sets numbered 1 to 17 as shown in Table 19, for HPV45; wherein a first primer/probe set of the triad is configured to produce a first amplicon signal, wherein a second primer/probe set of the triad is configured to produce a second amplicon signal, wherein a third primer/probe set of the triad is configured to produce a third amplicon signal, and wherein the primer/probe set of the triad with the smallest set number corresponds to the first primer/probe set and the primer/probe set of the triad with the largest set number corresponds to the third primer/probe set.

For example, if one selects three primer/probe sets numbered 3, 5, and 7 from a table, e.g., Table 14, then set 3 is the "first primer/probe set," set 5 is the "second primer/probe set," and 7 is the "third primer/probe set." The smallest set number always corresponds to the first set and the largest set number always corresponds to the third set, and so the middle number always corresponds to the second set.

In these compositions, the triad of modified oligonucleotide primer/probe sets can be selected from primer/probe sets numbered 1 to 18 as shown in Table 14 for HPV16, or primer/probe sets numbered 1 to 18 as shown in Table 15 for HPV18, or primer/probe sets numbered 1 to 17 as shown in Table 16 for HPV31, or primer/probe sets numbered 1 to 15 as shown in Table 17 for HPV33, or primer/probe sets numbered 1 to 16 as shown in Table 18 for HPV35, or primer/probe sets numbered 1 to 17 as shown in Table 19 for HPV45.

In some embodiments, the disclosure provides compositions for detecting tumor-derived Human Papilloma Virus type 16 (HPV16) in a sample from a subject, including a triad of modified oligonucleotide primer/probe sets selected from primer/probe sets numbered 1 to 18 as shown in Table 14 for HPV16, wherein a first primer/probe set of the triad is configured to produce a first amplicon signal, wherein a second primer/probe set of the triad is configured to produce a second amplicon signal, wherein a third primer/probe set of the triad is configured to produce a third amplicon signal, and wherein the primer/probe set of the triad with the smallest set number corresponds to the first primer/probe set and the primer/probe set of the triad with the largest set number corresponds to the third primer/probe set.

In another aspect, the disclosure provides compositions for detecting tumor-derived Epstein-Barr virus (EBV) in a sample from a subject, including a triad of modified oligonucleotide primer/probe sets selected from primer/probe sets numbered 1 to 28 as shown in Table 20 for EBV, wherein a first primer/probe set of the triad is configured to produce a first amplicon signal, wherein a second primer/probe set of the triad is configured to produce a second amplicon signal, wherein a third primer/probe set of the triad is configured to produce a third amplicon signal, and wherein the primer/probe set of the triad with the smallest set number corresponds to the first primer/probe set and the primer/probe set of the triad with the largest set number corresponds to the third primer/probe set.

In these compositions, the triad can contain three (or four or more) primer/probe sets of which no two primer/probe sets are consecutive, or the triad can contain three (or four or more) non-consecutive primer/probe sets.

In certain embodiments, the primer/probe sets are numbered 3, 5, and 7 or 4, 7, and 10, as shown in Table 14 for HPV16, or 4, 7, and 10 as shown in Table 15 for HPV18, or 4, 7, and 10 as shown in Table 16 for HPV31, or 4, 7, and 10 as shown in Table 17 for HPV33, or 4, 7, and 10 as shown in Table 18, for HPV35, or 4, 7, and 10 as shown in Table 19, for HPV45. In some embodiments, the primer/probe sets are numbered 4, 5, and 6 as shown in Table 20 for EPV.

In various embodiments, the compositions described herein can further include one or more reporter moieties, such as reporter dyes, e.g., FAM, HEX, VIC, Cy5TM, or Cy5.5. For example, the detection probe 5 of Table 14 can be conjugated to reporter moiety HEX and detection probes 3 and 7 of Table 14 can be conjugated to reporter moiety FAM. In another example, detection probe 7 of Table 14 can be conjugated to reporter moiety FAM and detection probes 4 and 10 of Table 14 can be conjugated to reporter moiety HEX.

In certain embodiments, the composition includes primer/probe sets numbered 1, 3, and 5, or sets numbered 1, 3, and 8, or probe sets numbered 4, 6, and 9, or sets numbered 14, 16, and 18, or sets numbered 1, 2, and 5, or sets numbered 10, 12, and 13, as shown in Table 14 for HPV16.

In another aspect, the disclosure provides methods for detecting tumor-derived Human Papilloma Virus type 16 (HPV16), HPV18, HPV31, HPV33, HPV35, or HPV45 in a sample from a subject, the methods including providing triads of any of the modified oligonucleotide primer/probe sets of any of the compositions described herein as recited in Tables 14, 15, 16, 17, 18, and 19; fractionating a plurality of HPV DNA fragments from the sample into droplets at a concentration wherein only 0 or 1 molecule of the DNA fragments is present in each droplet; amplifying HPV DNA in each droplet with the triad of primer/probe sets to produce amplicon signals; and detecting in each droplet any amplicon signals; wherein detection within a droplet of the second amplicon, but not the first or third amplicon, indicates that the HPV DNA fragment fractionated into the droplet is a tumor-derived HPV DNA fragment.

In these methods, the triad can contain three primer/probe sets from Table 14 and the method detects tumor-derived HPV16, or the triad can contain three primer/probe sets from Table 15 and the method detects tumor-derived HPV18, or the triad can contain three primer/probe sets from Table 16 and the method detects tumor-derived HPV31, or the triad can contain three primer/probe sets from Table 17 and the method detects tumor-derived HPV33, or the triad can contain three primer/probe sets from Table 18 and the method detects tumor-derived HPV35, or the triad can contain three primer/probe sets from Table 19 and the method detects tumor-derived HPV45.

In another aspect, the disclosure provides methods for detecting tumor-derived Human Papilloma Virus type 16 (HPV16) in a sample from a subject, the method including providing a triad of modified oligonucleotide primer/probe sets of any of the composition described herein as recited in Table 14; fractionating a plurality of HPV DNA fragments from the sample into droplets at a concentration wherein only 0 or 1 molecule of the DNA fragments is present in each droplet; amplifying HPV DNA in each droplet with the triad of primer/probe sets to produce amplicon signals; and detecting in each droplet any amplicon signals; wherein detection within a droplet of the second amplicon, but not the first or third amplicon, indicates that the HPV DNA fragment fractionated into the droplet is a tumor-derived HPV DNA fragment.

In another aspect, the disclosure provides methods for detecting tumor-derived Epstein-Barr virus (EBV) in a sample from a subject, the methods including providing triads of any of the modified oligonucleotide primer/probe sets of any of the compositions described herein as recited in Table 20; fractionating a plurality of EBV DNA fragments from the sample into droplets at a concentration wherein only 0 or 1 molecule of the DNA fragments is present in each droplet; amplifying EBV DNA in each droplet with the triad of primer/probe sets to produce amplicon signals; and detecting in each droplet any amplicon signals; wherein detection within a droplet of the second amplicon, but not the first or third amplicon, indicates that the EBV DNA fragment fractionated into the droplet is a tumor-derived EBV DNA fragment.

In all of the methods described herein, the DNA fragments can be fractionated into micro-droplets by emulsification, and/or the DNA can be amplified using a PCR based method.

In all of the methods described herein, the sample can be a blood, saliva, gargle, or urine sample, e.g., a blood sample.

In other aspects, the disclosure provides methods for detecting tumor-derived HPV16, HPV18, HPV31, HPV33, HPV35, or HPV45, in a sample from a subject utilizing a composition of oligonucleotides of primers and probes including any triad of primer/probe sets from Table 14, 15, 16, 17, 18, or 19, respectively, wherein a first primer/probe set, consisting of two primers and one probe, is configured to produce a first amplicon signal, wherein a second primer/probe set, consisting of two primers and one probe, is configured to produce a second amplicon signal, wherein a third primer/probe set, consisting of two primers and one probe, is configured to produce a third amplicon signal; fractionating DNA fragments from a sample from the subject into droplets at a concentration wherein only 0 or 1 DNA fragments are present in each droplet; amplifying the DNA in each droplet with the series of primer/probe sets to produce the amplicon signals; and detecting in each droplet the number of amplicon signals, wherein detection of the second amplicon but not the first or third amplicon is an indication that the subject has tumor-derived HPV16, HPV18, HPV31, HPV33, HPV35, or HPV45.

Also disclosed are methods for detecting tumor-derived EBV in a sample from a subject utilizing a composition consisting of non-consecutive triad of primer/probe sets from Table 20, wherein a first primer/probe set, consisting of two primers and one probe, is configured to produce a first amplicon signal, wherein a second primer/probe set, consisting of two primers and one probe, is configured to produce a second amplicon signal, wherein a third primer/probe set, consisting of two primers and one probe, is configured to produce a third amplicon signal; fractionating DNA fragments from a sample from the subject into droplets at a concentration wherein only 0 or 1 DNA fragments are present in each droplet; amplifying the DNA in each droplet with the series of primer/probe sets to produce the amplicon signals; and detecting in each droplet the number of amplicon signals, wherein detection of the second amplicon but not the first or third amplicon is an indication that the subject has tumor-derived EBV.

Methods for DNA fragmentation into droplets for digital PCR are known, and include fractionation into micro-droplets by emulsification. In some embodiments, the DNA is fractionated based on size prior to performing emulsification into micro-droplets. This can be done, for example, to isolate a range of DNA fragments for quantification by size.

The DNA fragments can be amplified using any known method, such as a PCR method or a non-PCR method.

In some embodiments, the subject has never been diagnosed with or suffered from an HPV-associated or EBV-associated malignancy. In other embodiments, the subject has previously undergone treatment for an HPV-associated or EBV-associated malignancy.

The disclosed methods can also be used to monitor treatment. Therefore, also disclosed herein is a method of monitoring HPV-associated or EBV-associated cancer or malignancy in a subject, that involves quantifying tumor-derived cell-free HPV or EBV viral DNA in blood samples collected at two or more time points during treatment of a subject being treated for the HPV-associated or EBV-associated malignancy using the disclosed methods. In some of these embodiments, the presence of the tumor-derived cell-free HPV or EBV viral DNA in samples collected at later points in time can be indicative that the subject being treated for an HPV-associated cancer or malignancy will have an increased likelihood for recurrence of the HPV-associated or EBV-associated malignancy. Likewise, in some of these embodiments, the rapid clearance of or absence of said tumor-derived cell-free HPV or EBV viral DNA in samples collected at later points in time can be indicative that the subject being treated for the HPV-associated or EBV-associated malignancy will have a decreased likelihood for recurrence the HPV-associated or EBV-associated malignancy. In these cases, the method can also further involve treating the subject with a reduction in radiation therapy and/or chemotherapy if the subject exhibits a rapid clearance of or an absence of the tumor-derived cell-free DNA sequences of HPV or EBV in samples collected at later points during the course of treatment.

According to aspects of the disclosed method, longitudinal analysis of tumor-derived virus nucleic acids in the blood with the disclosed method may be utilized for early detection of virus-positive cancers in individuals who do not present any symptoms related to their malignancy or in whom such symptoms have not yet been identified by clinicians. As demonstrated herein, the disclosed method allows previously unachievable levels of sensitivity and specificity for detecting circulating tumor-derived viral nucleic acids that is applicable to patients with HPV+ or EBV+ cancers.

In some embodiments, the disclosed methods can be applied to determine the likelihood of initial diagnosis or recurrence of a virus-associated cancer comprising detecting the presence or absence of at least one circulating tumor nucleic acid marker for the relevant virus in blood samples collected from a subject at a single time point or longitudinally over time.

In some embodiments, the disclosed methods can be applied for selecting treatments for oropharyngeal squamous cell carcinoma (OPSCC) or other virus-associated cancer comprising detecting the presence or absence of at least one circulating tumor-derived human papilloma virus (HPV) DNA in samples collected prior to starting treatment and/or at various points in time during treatment from a subject diagnosed with OPSCC or being treated for OPSCC, wherein the presence and/or quantity of said circulating tumor-derived HPV DNA in samples collected at later points in time is indicative that the subject being treated for OPSCC will have an increased likelihood for OPSCC recurrence. Alternatively, rapid clearance of or absence of said circulating tumor-derived HPV DNA in samples collected at later points in time is indicative that the subject being treated for OPSCC will have a decreased likelihood for OPSCC recurrence, and treating the subject with a reduction in radiation therapy and/or chemotherapy if the subject exhibits a rapid clearance of or an absence for said circulating tumor nucleic acid marker for HPV at a specific point in time after initiating cancer therapy.

Also disclosed herein are methods of determining a treatment regimen for human papilloma virus (HPV)-associated cancer or malignancy comprising detecting the presence or absence of at least one circulating tumor-derived HPV DNA in samples collected at different points in time during treatment from a subject diagnosed with HPV-associated cancer or being treated for said HPV-associated malignancy, wherein the absence of or the rapid clearance of said circulating tumor-derived HPV DNA in samples collected at later points in time during treatment is indicative that the subject can be treated with a reduction in radiation therapy and/or chemotherapy.

Also disclosed herein are methods of detecting, monitoring and/or treating a HPV-associated or EBV-associated malignancy in a subject, the method comprising detecting a presence or absence of at least one circulating tumor-derived HPV or EBV DNA in samples collected from the subject at various points in time during a course of treatment, wherein the presence of the circulating tumor-derived HPV or EBV DNA in samples collected at later points in time during the course of treatment is indicative that the subject has an HPV-associated or EBV-associated malignancy or an increased likelihood for an HPV-associated or EBV-associated malignancy recurrence, and the rapid clearance of or absence of circulating tumor-derived HPV or EBV DNA in samples collected at later points in time during the course of treatment is indicative that the subject does not have an HPV-associated or EBV-associated malignancy or has a decreased likelihood for an HPV-associated or EBV-associated malignancy.

Also disclosed herein are methods for monitoring and/or treating a HPV-associated or EBV-associated malignancy in a subject comprising detecting levels of a circulating tumor-derived HPV or EBV DNA in samples collected at various points in time from the subject diagnosed with or being treated for the HPV-associated or EBV-associated malignancy; determining a circulating tumor-derived HPV or EBV DNA profile for the subject; and adjusting a treatment regimen for the HPV-associated or EBV-associated malignancy according to the circulating tumor-derived HPV or EBV DNA profile, wherein a subject with a favorable circulating tumor-derived HPV or EBV DNA profile is treated with a de-intensified treatment regimen.

Also disclosed herein are kits including components and compositions as described herein for detecting, monitoring, and/or treating malignancies in a subject as described herein, and instructions for the use thereof. For example, the kits can contain primer/probe sets set forth in Tables 14 to 20, and instructions for the use thereof.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A) Dual fragment HPV16 assay to detect tumor viral DNA. Shown are the digital PCR fluorescence detection plots for simultaneous detection of two distinct fragments of the HPV16 genome. Examples are shown for the single positive controls, dual fragment positive control, intact HPV genome control, and two patient plasma DNA samples. Gates used to quantify single- and double-positive droplets are shown, as described in the methods. FIG. 1B) Analysis of 12 plasma DNA samples from patients with HPV+ oropharyngeal cancer using this assay uniformly demonstrates the presence of tumor-derived viral DNA-indicated by abundance of both fragments in single positive droplets and very rare co-occupancy of both targets in the same droplet (in contrast to the intact genome control).

FIG. 3A) Schematic of timepoints when blood was sampled in a cohort of oropharyngeal cancer patients prior to, during, and after receiving chemoradiotherapy (CRT). FIG. 3B) Two patterns of plasma ctHPV16 profile observed after initiating CRT. In some patients (red lines), ctHPVDNA levels are highest pre-treatment and diminish after initiating therapy. In other cases (blue lines), ctHPVDNA levels increase soon after starting treatment, possibly due to a spike in cancer cell death. In all cases, ctHPVDNA levels are markedly reduced at the end of CRT, indicating that ctHPVDNA levels are correlated with the volume of active cancer in patients. FIG. 3C) A subset of patients have rapid clearance kinetics of ctHPVDNA during CRT, with >95% of ctHPVDNA cleared by week 4 of CRT. FIG. 3D) Another subset of patients has delayed kinetics of ctHPVDNA clearance after CRT, which may be correlated with poor or delayed response to CRT.

FIG. 4A) There was a strong correlation between the HPVDNA dPCR assay described in Example 1, when applied to the tumor biopsy specimen, and tumor HPV copy number assessed by NGS. This validates both the HPVDNA assay and NGS using orthogonal assays on the same samples. FIG. 4B) There is a statistically significant correlation between tumor HPV copy number per cellular genome and pre-treatment ctHPVDNA in the blood, normalized to tumor volume ("ctHPVDNA density"). This indicates that the level of ctHPVDNA detected in blood is correlated with HPV copy number in the associated tumor. FIG. 4C) A bioinformatics analysis pipeline was developed to distinguish HPV+ HPV cancers that have evidence of HPV integration into the human genome versus those cancers that have purely episomal HPV, using the tumor NGS data. FIG. 4D) A circos plot is shown demonstrated the observed rearrangements in a cancer with episomal HPV (left) and integrated HPV (right). The example with integrated HPV shown here has an integration site that maps to a region on chromosome 8 (see the dark black lines). FIG. 4E) Higher tumor HPV copy number correlates with a greater likelihood of non-integrated (episomal only) HPV. FIG. 4F) Higher ctHPVDNA levels in blood also correlate with a higher likelihood of non-integrated (episomal only) HPV in the associated cancer. Thus, ctHPVDNA can also provide information on the status of the HPV genome in the associated cancer—i.e., if it is integrated versus episomal.

FIG. 5A) A schematic for stratifying patients based on their ctHPVDNA profile. Patients with abundant pre-treatment ctHPV16DNA that is rapidly cleared (>95% by day 28) are classified as having a favorable ctHPVDNA profile. All other patients are classified as having an unfavorable ctHPVDNA profile. FIG. 5B) Favorable ctHPVDNA profile is observed in ~30% of patients with clinically favorable (<T4 and <=10 pack-year smoking history) and in ~30% of patients with clinically unfavorable (T4 or >10 pack-year smoking history) disease.

FIG. 6A) Proportion of patients in each subgroup who had a positive post-treatment neck dissection (i.e., regionally persistent disease), regional recurrence, and distant metastasis. Patients who had unfavorable clinical risk factors and an unfavorable ctHPVDNA profile had the highest risk of adverse disease events. FIG. 6B) Kaplan-Meier analysis of regional disease (persistent or recurrent) free survival stratified by clinical risk and ctHPVDNA profiles. Patients with a Favorable ctHPV16DNA Profile had 100% regional disease control, regardless of smoking history (5 patients were heavy smokers). In contrast, clinical higher risk patients with an Unfavorable ctHPVDNA Profile had significantly reduced regional disease control. P, two-tailed logrank test for a trend.

DETAILED DESCRIPTION

Figure 1A:
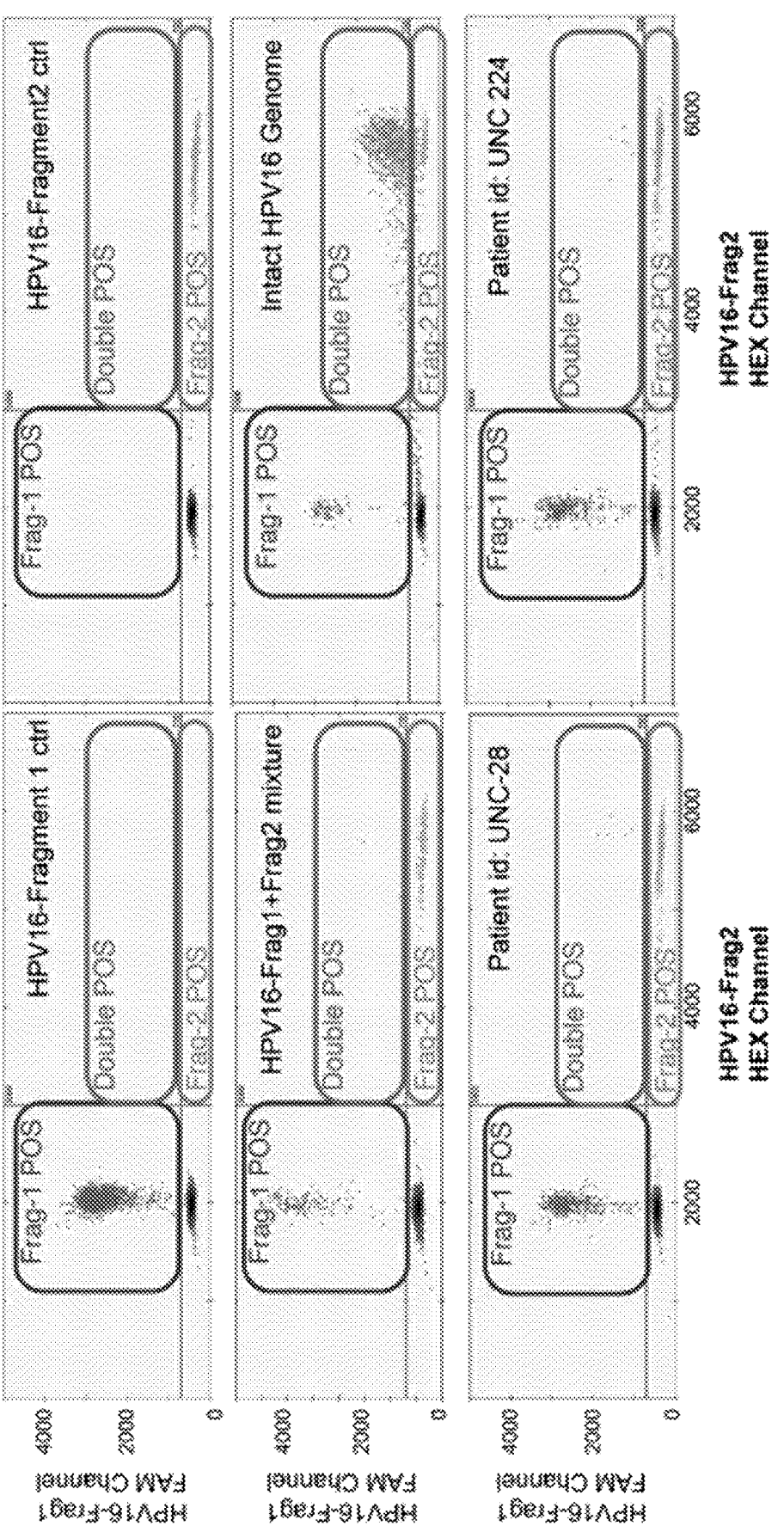
FIGS. 1A and 1B.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, useful methods and materials are now described.

All publications and patents cited in this specification are herein incorporated by reference in their entireties, as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The examples are put forth so as to provide those of ordinary skill in the art with a complete disclosure and description of how to perform the methods and how to make and use the compositions and probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

As used herein "human papilloma virus" or "HPV" refers to small, non-enveloped, double-stranded DNA viruses that infect the cutaneous and/or mucosal epithelium. As understood by those skilled in the art, over 100 HPV genotypes are known to exist. Sexually transmitted, mucosotropic HPVs are further subcategorized as high risk (e.g. HPV16 and HPV18) or low risk (HPV6 and HPV11).

As used herein, HPV-associated malignancies include those of the head and neck (larynx, oral cavity, oropharynx, tonsils, and esophagus), respiratory tissue, breast, skin, cervix, vulva, penis and anus. Malignancy and cancer are used interchangeably.

As used herein, "detecting" or "detection" means testing, screening, or otherwise determining the presence and/or absence of at least one tumor nucleic acid marker for HPV in a sample. Such detecting or detection can be carried out by methods described herein, including those known in the art as applicable to this technology, for example, nucleic acid amplification, hybridization-based detection, microarray, and next generation sequencing.

Also as used herein, the terms "treat," "treating" or "treatment" may refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, delay of the onset of the disease, disorder, or illness, and/or change in clinical parameters of the condition, disorder, disease or illness, etc., as would be well known in the art.

As used herein, the term "monitoring" refers to assessing the therapeutic efficacy of a treatment for patients with a cancer. As used herein, the term "surveillance" refers to the detection of a virus-associated malignancy in subjects, who may or may not have a clinically diagnosed or symptomatic cancer.

As used herein, a subject has an "increased likelihood" of some clinical feature or outcome (e.g., recurrence or progression) if the probability of the subject having the feature or outcome exceeds some reference probability or value. The reference probability may be the probability of the feature or outcome across the general relevant subject or patient population. For example, if the probability of recurrence in the general oropharyngeal cancer population is X % and a particular patient has been determined by the methods to have a probability of recurrence of Y %, and if Y>X, then the patient has an "increased likelihood" of recurrence. Alternatively, a threshold or reference value may be determined and a particular patient's probability of recurrence may be compared to that threshold or reference.

As used herein, "sample" refers to a biological sample containing a tumor nucleic acid marker for HPV. The sample may be tissue, cells, or any fluid taken from the human body, e.g., blood, plasma, urine, saliva, etc. In particular embodiments, the sample is a blood-based sample. Accordingly, the sample may be whole blood or components thereof such as serum or plasma.

Also disclosed herein are methods for detection, treatment, and surveillance of human papilloma virus-associated malignancies and kits for accomplishing the same.

Also disclosed herein are methods for quantifying viral nucleic acids in the circulatory system that are specifically derived from tumors, and for distinguishing these tumor-derived viral nucleic acids from other sources of circulating viral nucleic acids.

Disclosed herein are DNA amplification methods for quantifying DNA fragments of a target DNA in a sample by size. This can be used, for example, to detect tumor-derived viral DNA in blood sample and distinguish it from larger viral DNA from non-tumor sources. In particular, disclosed herein are methods of detecting, monitoring, or treating a human papilloma virus (HPV)-associated malignancy in a subject that involves detecting a presence or absence of at least one circulating tumor-derived HPV DNA in a sample from the subject. Kits for accomplishing the same are also provided.

The disclosed method can be performed within thousands of micro-droplets (also referred to herein as droplets) generated through, for example, emulsification and/or water-in-oil droplet partitioning, such as is described in Hindson et al., Anal Chem. 2011 Nov. 15; 83(22):8604-8610, Pinheiro et al., Anal Chem. 2012 Jan. 17; 84(2):1003-1011, and Kanagal-Shamanna, Methods Mol Biol. 2016; 1392:33-42, or any other method known to those versed in the art to separate a sample into discrete and/or volumetrically defined partitions for analysis of tumor derived versus non-tumor derived DNA present in the partitions/sample. In the case of micro-droplets, the size of the droplets can be micro-, nano-, pico-, or femto-scale.

As disclosed herein, the micro-droplets are generated such that they each contain at most a single targeted viral nucleic acid. In embodiments where only two distinct regions of the viral nucleic acid are detected, a micro-droplet containing the targeted viral nucleic acid will be either single-positive, i.e., positive for one of the detection signals, or double-positive, i.e., positive for both of the detection signals. As disclosed herein, the relative numbers of the single-positive and double-positive micro-droplets and double-positive droplets provide quantitative information making it possible to quantitatively determine the relative amounts of tumor-derived and non-tumor derived viral DNA in the sample.

In embodiments where the PCR is used to detect two physically distinct regions, included is a forward and reverse primer pair corresponding to each detected region. In some embodiments, the detection may be performed using digital PCR, droplet digital PCR, emulsion PCR or micro-droplet PCR according to procedures that would be appreciated by one of skill in the art. As disclosed herein, micro-droplets containing tumor-derived circulating viral nucleic acids have fewer positively detected viral nucleic acid regions relative to micro-droplets containing non-tumor-derived circulating viral nucleic acids. In the simplest case where only 2 different regions in the viral nucleic acid are targeted for detection, the disclosed method identifies micro-droplets containing non-tumor-derived circulating viral DNA as those that are positive for both of the detection signals employed for the different targeted regions (double-positive); by contrast, in this simplest case, micro-droplets containing tumor-derived circulating viral nucleic acid are positive for only one detection signal but not both signals simultaneously.

To take an illustrative example, if the target nucleic acid regions for detection comprise fragments of ~70-100 bp, two or more target regions separated by 100 bp would never be present on the same viral DNA molecule if the molecule was derived from circulating tumor DNA. Under this scenario, the simultaneous detection of both target fragments within the same micro-droplet must be due to co-occupancy within the same micro-droplet of two distinct target fragment molecules, each containing one of the regions targeted for detection. Thus, if the analyzed samples contain non tumor-derived viral DNA, there will be a higher frequency of micro-droplets that test positive for two or more target fragments than would be expected based on the frequencies of each target region analyzed individually.

For example, one quantitative measurement of the proportion of non-tumor-derived viral DNA fragments in the sample is [fraction(droplets double-positive for both detection signals)–fraction(droplets positive only for detection signal 1)*fraction(droplets positive only for detection signal 2)]. It follows that the fraction of tumor-derived viral DNA in the sample is [1–[fraction(droplets double-positive for both detection signals)–fraction(droplets positive only for detection signal 1)*fraction(droplets positive only for detection signal 2)]]. The corresponding quantitative measure of tumor-derived viral DNA would be [#(droplets positive only for detection signal 1)+#(droplets positive only for detection signal 2)]*[proportion of tumor-derived viral DNA fragments]=[#(droplets positive only for detection signal 1)+# (droplets positive only for detection signal 2)] [1–fraction (droplets positive for both detection signals)+fraction (droplets positive only for detection signal 1)*fraction (droplets positive only for detection signal 2)]. These formulae are provided as illustrative examples of how the raw detection signal data can be converted into measurements of tumor-derived and non-tumor-derived viral DNA in the sample, with the understanding there are other formulae that could be utilized for the same purpose.

The disclosed methods can also be applied in cases where 3 or more regions, each with its own detection signal, are detected in each micro-droplet or other parallelized micro-reaction chamber. In this context, the mathematical formula for quantification of tumor-derived and non-tumor derived viral DNA can be generalized on the basis of the reasoning provided above for 2 amplified regions.

While the examples above considered detected viral DNA regions of size ~70-100 bp separated by at least about 50 bp, about 60 bp, about 70 bp, about 80 bp, about 90 bp or about 100 bp, it should be understood that both the size of the detected DNA fragments and their distance may be varied and are not fixed in relation to the disclosed methods.

Returning to the embodiment in which two different regions are targeted for detection, double-positive micro-droplets may on occasion arise from the co-incidence of two smaller fragments of viral nucleic acid within a single micro-droplet, each fragment containing just a single region targeted for detection, as opposed to the desired measurement of one larger fragment encompassing both of the regions targeted for detection. In some embodiments, this possibility can be ruled out, or the extent to which it is occurring quantified, by comparing the relative frequencies of double-positive and single-positive droplets, and confirming that the frequency of double-positive droplets is approximated by the product of the frequencies of the single-positive droplets, and reduces in prevalence by the square of the dilution factor when re-analyzed at a lower concentration.

In some embodiments, nucleic acids isolated from blood samples are emulsified into micro-droplets such that the vast majority of micro-droplets contain either one or none of the viral nucleic acids that are being targeted for detection. Experimental methods for determining the correct micro-droplet volume and blood sample dilution factors are provided herein. Subsequent to emulsification, nucleic acid detection methods, which may include PCR-based methods, are employed to detect two or more regions of the targeted viral nucleic acid that are physically separated from one another. In some embodiments, each viral region being targeted detection is associated with a unique detection signal, for example a unique fluorescent color.

Also disclosed herein are methods of detecting ctHPVDNA in HPV-OPSCC patients. The methods generally involve detecting the presence of tumor-derived viral DNA using a nucleic acid amplification, such as polymerase chain reaction (PCR), in an emulsified context in which least two distinct regions are amplified to distinguish between tumor-derived viral DNA, which is fragmented, and non-tumor-derived intact virions, whose DNA is not fragmented. Also disclosed herein are nucleic acid probes and nucleic acid primers, as well as kits comprising same, for use in a said method.

Also disclosed herein are methods for identifying the prognosis of individuals with HPV-associated OPSCC that can be successfully treated by de-intensified chemo-radio-therapy (CRT), methods for identifying tumor-specific bio-markers that are predictive of HPV-associated OPSCC relapse or recurrence after treatment, and methods of identifying the prognosis of individuals with HPV-associated OPSCC who are at risk for relapse or recurrence after treatment.

Subjects suitable to be treated by the disclosed methods include, but are not limited to mammalian subjects. Mammals include, but are not limited to, canines, felines, bovines, caprines, equines, ovines, porcines, rodents (e.g., rats and mice), lagomorphs, primates, humans and the like, and mammals in utero. Any mammalian subject in need of being treated or desiring treatment is suitable. Human subjects of any gender (for example, male, female or transgender) and at any stage of development (i.e., neonate, infant, juvenile, adolescent, adult, elderly) may be treated. Subjects may be of any race or ethnicity, including, but not limited to, Caucasian, African-American, African, Asian, Hispanic, Indian, etc., and combinations thereof. It should be further noted that subject and patient are used interchangeably.

In particular embodiments, the subject has never been diagnosed with or suffered from a virus-associated malignancy. In other embodiments, the subject may be diagnosed with, afflicted with, suffering from or at risk for a virus-associated malignancy. In some embodiments, the subject has previously undergone treatment for a virus-associated malignancy. In other embodiments, the subject may be in remission from a virus-associated malignancy. In some embodiments, the subject is a smoker. In some embodiments, the subject is a non-smoker.

Detection of ctHPVDNA

Methods for determining the level of biomarker nucleic acid, for example, a ctHPVDNA, such as ctHPV16DNA, in a sample may involve the process of nucleic acid amplification, e.g., by PCR, ligase chain reaction (LCR), transcription-based amplification systems, (TAS) self-sustained sequence replication (3SR), nucleic acid sequence-based amplification (NASBA), strand displacement amplification (SDA) and branched DNA (bDNA) amplification, Q-Beta replicase, rolling circle replication, rolling circle amplification, or any other nucleic acid amplification method, followed by detection of the amplified molecules using any technique as would be appreciated by one of skill in the art.

In some embodiments, the nucleic acid detection method may be carried out in micro-droplets or other micro-reaction chamber so that the detection method can be run in a highly parallelized manner. In some embodiments, micro-droplets or micro-reaction chambers may contain either 0 or 1 copies of the viral DNA region targeted for detection.

In embodiments involving emulsion PCR, a target nucleic acid or polynucleotide sequence is typically dispersed into micro-droplets. In some embodiments, it is essential that the target nucleic acids be emulsified at a concentration where each micro-droplet (or droplet) contains either one or zero copies of the target molecule. In the case of plasma or serum DNA isolated from patient blood samples, the appropriate dilution level can be recognized by assessing the abundance of a control genomic region and assuring that the frequency of positive micro-droplets remain less than 10% (<10%). The control genomic region detects human (i.e., non-viral) DNA and serves as a quality control for the sample (since many negative samples will not have any positive signal in the assay), and will also be used to establish that the concentration of DNA fragments is appropriate (not to low and not too high).

Within each micro-droplet, the principles of conventional PCR also apply, where the target molecule is amplified by reaction with at least one oligonucleotide primer or pair of oligonucleotide primers. The primer(s) hybridize to a complementary region of the target nucleic acid and a DNA polymerase extends the primer(s) to amplify the target sequence. Under conditions sufficient to provide polymerase-based nucleic acid amplification products, a nucleic acid fragment of one size dominates the reaction products (the target polynucleotide sequence which is the amplification product). The amplification cycle is repeated to increase the concentration of the single target nucleic acid or polynucleotide sequence within each micro-droplet. The reaction can be performed in any thermocycler commonly used for PCR.

Methods for setting up a PCR reaction are well known to those skilled in the art. Any known DNA polymerase, nucleoside triphosphate, buffers, additives/reaction enhancers and conditions for amplification (cycles of denaturation, annealing and polymerization) as would be appreciated by one of skill in the art may be used in the PCR reaction.

In some embodiments, the reaction includes a sequence-specific, hydrolysis probe that is conjugated to both a fluorescent molecule and a fluorescence-quenching molecule to the reaction mixture to enable the detection of successful amplification of the target molecule within each droplet. The chemical composition of specific probes may vary, but follow an established method for detecting synthesis-based nucleic acid amplification by those skilled in the art.

The preparation of an emulsion of the PCR reaction can be achieved in a variety of ways that are appreciated by those versed in the art. One effective methodology utilizes a fabricated microfluidic chip that mixes the aqueous PCR reaction with a lipid solution at controlled pressure to generate micro-droplets of uniform size. The disclosed method is applicable to any method for achieving a partitioned PCR reaction mixture that allows the simultaneous detection of two or more viral nucleic acid target molecules.

Following preparation of a PCR reaction mixture that has been appropriately emulsified or partitioned into droplets, the reaction mixture is subjected to primer extension reaction conditions ("conditions sufficient to provide polymerase-based nucleic acid amplification products"), i.e., conditions that permit for polymerase mediated primer extension by addition of nucleotides to the end of the primer molecule using the template strand as a template. Cycles of denaturation, annealing and polymerization may be performed according to any conditions (e.g., number of cycles, temperatures and duration in time) that would be appreciated by one of skill in the art.

Cycles of denaturation, annealing and polymerization may be performed using an automated device, typically known as a thermal cycler. Thermal cyclers that may be employed are described elsewhere herein as well as in U.S. Pat. Nos. 5,612,473; 5,602,756; 5,538,871; and 5,475,610.

In other embodiments, non-PCR based applications may be used to detect a target nucleic acid sequence, for example, where such target may be immobilized on a solid support. Methods of immobilizing a nucleic acid sequence on a solid support are known in the art and are described in Ausubel et al. Current Protocols in Molecular Biology, John Wiley and Sons, Inc. and in protocols provided by the manufacturers, e.g. for membranes: Pall Corporation, Schleicher & Schuell, for magnetic beads: Dynal, for culture plates: Costar, Nalgenunc, and for other supports.

Other nucleic acid amplification procedures will be appreciated by one of skill in the art, such as, but not limited to, LCR, TAS, 3SR, NASBA, SDA, bDNA, and isothermal amplification. The disclosed method is not limited to the use of amplification by PCR, but rather includes the use of any nucleic acid amplification methods or any other procedures which may be useful in amplification of the sequences for the detection and/or quantification of the presence of or expression of one or more of the particular nucleic acid sequences described herein.

Variations on the exact amounts of the various reagents and on the conditions for the PCR or other suitable amplification procedure (e.g., buffer conditions, cycling times, etc.) that lead to similar amplification or detection/quantification results are known to one of skill in the art and are considered to be equivalents.

Detection of the presence of target molecules in a sample/micro-droplet is not particularly limited, and may be accomplished by any technique appreciated by one of skill in the art. In some embodiments, detection may include hybridization of the target molecule with a target-specific probe, such as a nucleic acid probe, linked to a fluorescent marker. In other embodiments, the marker may be a non-fluorescent marker. The nature of the marker, fluorescent or non-fluorescent, is not particularly limited and may be any marker or label as would be appreciated by of skill in the art.

The detection and distinguishing of partitions (droplets) that contain a target molecule from partitions that contain zero target molecules is a critical step in digital PCR. This can be achieved using a variety of established techniques. In some embodiments, micro-droplets are analyzed individually using a microfluidic channel and a fluorescence detector. Alternatively, advanced microscopy techniques may be implemented to count positive and negative droplets. The disclosed method may be embodied with any nucleic acid detection method.

While some methods disclosed herein have been implementing using digital PCR, the disclosed methods can in principle be utilized with any nucleic acid detection method that is capable of detecting single nucleic acids and distinguishing the size of the detected fragments. For example, such methods may include, hybridization of non-amplified target molecules with a fluorescent or a non-fluorescent probe, and the like. In any such embodiments, the disclosed methods can be applied to distinguish tumor-derived viral nucleic acids in circulation from other non-malignant sources of circulating viral nucleic acid and intact virions. Particular aspects of the disclosed methods are the simultaneous detection in a partitioned reaction of at least two fragments of DNA separated by a defined distance in the viral genome, where the presence of both targets in separate partitions is indicative of tumor viral nucleic acid in a bodily fluid, such as the blood, wherein an increased frequency of co-occupancy of both fragments in the same partition is indicative of non-malignant viral nucleic acids.

The present invention is more particularly described in the following examples that are intended as illustrative only since numerous modifications and variations therein will be apparent and understood to those skilled in the art. Examples of how the application of this specific and sensitive method for detecting tumor viral nucleic acids in a bodily fluid, such as blood, can be used to predict patient prognosis during cancer treatment, and to identify patients who are at the highest risk of disease recurrence among a cohort of patients who are clinically asymptomatic and thought to be in disease remission are provided below.

A number of embodiments of the invention have been described. The disclosure is further described in the following examples, which do not limit the scope of the invention described in the claims.

EXAMPLES

Example 1: Digital PCR Assay to Detect HPV Viral DNA in Circulating Cell-Free DNA Provided here is an embodiment of the disclosed methods that uses digital emulsion PCR to detect tumor-derived viral HPV DNA in the circulating cell-free DNA isolated from blood. The methodological details described in this example, for example the nucleic acid amplification and detection methods used, are included solely to establish that the invention has been reduced to practice. The methodological details provided in this example related only to this particular embodiment are not to be construed as limiting the invention, as described in the claims and summary sections of this document.

Materials

Reagents: Cell-Free DNA BCT tubes, RUO (Streck catalog No. #218962); QIAamp™ Circulating Nucleic Acid Kit, Catalog #55114; dPCR Supermax® Bio-Rad catalog no #186-3024; Eppendorf™ 96-Well Twin.tec™ PCR Plates; Fisher scientific catalog No. #E951020362; Pipet tips (Bio-Rad catalog No. #186-4121 or #186-4120); Cartridge (Bio-Rad catalog No. #186-4109 or #186-4108); Sealing foil (Bio-Rad catalog No. #181-4040); Optional: VacConnec-tors® (Qiagen Cat No./ID: 19407).

This extra connector is useful in case something goes wrong with connectors available in QIAamp Circulating Nucleic Acid Kit, Catalog #55114; Bovine Serum Albumin (BSA); Qubit™ dsDNA HS Assay Kit (Thermo Fisher Scientific Catalog number: #Q32851); Qubit™ Assay Tubes (Thermo Fisher Scientific Catalog number: #Q32856); Falcon® 15 ml Conical Centrifuge Tubes (Corning Catalog No. #352096); Falcon™ 50 ml Conical Centrifuge Tubes (Corning Catalog No. #352098); Disposable sterile 5 ml, 10 ml and 25 ml Serological Pipets (any good brand); Sterile PCR tubes (Any good brand); Sterile filter tips for capacity 2 µl, 10 µl, 200 µl and 1200 µl (any good brand); primers and probes.

Instruments: Microcentrifuge (suitable for 1.5 ml Eppendorf tubes, e.g. Eppendorf 5424 Microcentrifuge); Centrifuge (Suitable for 15 ml falcon tubes, e.g. Eppendorf Centrifuge 5810 R); Qubit Fluorimeter (Thermo Fisher Scientific Catalog No. #Q33226); Deep 96 well thermocycler (Bio-Rad's C1000 Touch™ Thermal Cycler with 96-Deep Well Reaction Module #1851197); Heating block for drying 1.5 ml Eppendorf tubes (Denville Scientific catalog No. #10540); Water bath (should have sufficient space for incubating twenty-four 50 ml Conical Centrifuge Tubes as 24 samples can be processed at one time); Automated droplet generator (Bio-Rad catalog No. #186-4101); Bio-Rad QX200™ Droplet Reader Catalog No. #1864003; Portable Pipet-Aid® XP Pipette Controller (Drummond Scientific, Catalog No. 4-000-101); Pipette (capacity: 2 µl, 10 µl, 20 µl, 200 µl and 1000 µl; any good brand); 8-channel pipette (any good brand, e.g. Eppendorf Catalog No. #3125000010).

Methods

Blood Collection: Blood is collected in Cell-Free DNA BCT tubes, RUO (Streck catalog No. #218962).

Plasma Extraction: Collected blood from step I should ideally be processed on the same day to extract plasma. Same tube can be centrifuged at 2000×g for 10 min at room temperature (RT). Supernatant is transferred to new Falcon™ 15 mL Conical Centrifuge Tubes. Care should be taken to avoid taking middle whitish layer below plasma. Centrifuge the tube again for 10 min at 2000×g at RT. Supernatant is then transferred to a new Falcon™ 15 ml Conical Centrifuge Tubes. The plasma is at −80° C. freezer till further use. NOTE: sometimes 10 min. centrifuge does not lead to clear separation of plasma layer. In such situation, sample should be centrifuged for another 10 min before taking out the plasma. Or, alternatively centrifugation at first step can be done for 15-20 min. Record the sample if plasma looks red. Sometimes extra processing of the sample is required during PCR step because of the hemolysis. Blood should be discarded in 10% bleach or autoclaved or according to any other institution/company approved protocol.

Plasma cell free DNA (cfDNA) Extraction: The stored plasma samples are thawed at 37° C. in a water bath for about 5 min. A Qiagen kit (QIAamp Circulating Nucleic Acid Kit, Catalog #55114) is used to extract DNA using manufacturer's protocol with the following modifications: Standard vacuum available in laboratory can be used in the protocol; The cfDNA is eluted in 2 steps—first with 100 µl elution buffer and then 75 µl elution buffer if plasma volume is more than 3 ml. Elution can be done in lower volume if the collected plasma volume is less to avoid excessive dilution of the cfDNA; and it was observed that incubation of the column for 3 min. after adding elution buffer (as suggested in the protocol) does not lead to the complete extraction of cfDNA. Generally, a 30 min to 1 h incubation at RT generally follows both elution steps. The cfDNA is quantified on a Qubit fluorimeter. (Note: Generally, 2 µl of the eluate is sufficient to be used for quantification purpose). The eluted cfDNA is stored at −20° C. freezer until further use. Note: The cfDNA recovered at first elution is used for all experiments and calculations. The cfDNA recovered in the second elution step is used only if cfDNA at first elution is exhausted. If a more concentrated cfDNA is required for any purpose like NGS, then the sample can be concentrated using speed vacuum.

dPCR: The dPCR involve three steps—Droplet generation; PCR; and droplet reading.

Droplet Generation: Prepare 25 µl reaction for each sample customized as per the following composition (Reagents: dPCR Supermax® Bio-Rad catalog no #186-3024; any nuclease free PCR grade water can be used; other reagents like forward primer, reverse primer and probe are designed by user)

TABLE 1

| | Reaction Mixtures | | | |
| --- | --- | --- | --- | --- |
| Component | Working stock | Final Conc. | 1× (sample) | 1× No template control (NTC) |
| Primers Mixture (4) | 22.5 µM each | 0.9 µM each | 1 µl | 1 µl |
| Probes Mixture (2) | 6.25 µM each | 0.125 µM each | 0.5 µl | 0.5 µl |
| Albumin | 10% | 0.4% | 1 µl | 1 µl |
| Betaine | 5M | 0.4 µM | 2 µl | 2 µl |
| Trehalose | 1.25M | 0.16M | 3.2 µl | 3.2 µl |
| dPCR Supermix | 2× | 1× | 12.5 µl | 12.5 µl |

TABLE 1-continued

Reaction Mixtures

| Component | Working stock | Final Conc. | 1× (sample) | 1× No template control (NTC) |
|---|---|---|---|---|
| DNA sample | 1×/Diluted | N/A | 4.3 μl | — |
| PCR grade Water | Adjustable | N/A | — | 4.3 μl |
| Total | | | 25 μl | 25 μl |

The primer and probe sequences for the ctHPVDNA assay described here are as follows:

TABLE 2

Primers and Probes

| Variant | Primers/Probes |
|---|---|
| HPV16 Fragment 1 | 283_HPV-16_F1 For: TGACTCTACGCTTCGGTTG (SEQ ID NO: 1) |
| | 284_ HPV-16_F1 Rev: GCCCATTAACAGGTCTTCC (SEQ ID NO: 2) |
| | 420_HPV-16_F1 Probe_FAM-ZEN_v2: CGTACAAAGCACACACGTAGACATTCGTAC (SEQ ID NO: 3) |
| HPV16 Fragment 2 | 424_ HPV16_F2_For: GGTTTGTAACATCCCAGGC (SEQ ID NO: 4) |
| | 425_ HPV16_F2_Rev: GTGTATTTTTTAAGGGGATCTTCTT (SEQ ID NO: 5) |
| | 421_HPV16_F2_HEX_LNA: CACCT(+C)(+C)A(+G)CACC (SEQ ID NO: 6) |

"(+N)" denotes LNA™ base

The Primers mixture working stock is assembled by combining 22.5 μL each of the four primers (100 μM concentration) into a tube and adding 10 μL nuclease-free water to achieve a final concentration of 22.5 μM for each primer.

The Probe mixture working stock is assembled by combining 6.25 μL of each probe (100 μM concentration) into a tube and adding 87.5 μL nuclease-free water to achieve a final concentration of 6.25 μL for each probe.

About 22-23 μl of the above reaction mixture is loaded on a 96 well plate (Eppendorf™ 96-Well Twin.tec™ PCR Plates, Fisher scientific catalog No. #E951020362) using Multichannel Pipetors (Note: Instrument uses only 20 μl from each well. An extra volume is added to avoid any pipetting error) Droplets are generated using automated droplet generator (Bio-Rad catalog No. #186-4101) following manufacturer's protocol. Reagents required at this step are pipet tips (Bio-Rad catalog No. #186-4121 or #186-4120) and cartridges (Bio-Rad catalog No #186-4109 or #186-4108). The sample plate is sealed with sealing foil (Bio-Rad catalog No. #181-4040) following manufacturer's protocol. Note: The volume of cfDNA+water should be 4.3 μl. Generally, there is no issue by using 4.3 μl of cfDNA sample in the reaction but sometimes the allele copy number is too high and it results in streaking of the positive droplet across the axis and many dual positive droplets. In such cases, the run should be repeated by using less sample and remaining volume can be adjusted with water. Dilution gives better quantification of allele frequency in such cases. A linear relationship across 5 orders of magnitude has been observed in HPV16 copy number ranging from 5 copies to 50,000 copies per 20 μl reaction. Care should be taken to seal the plate properly. If the plate is not sealed properly then it will lead to sample evaporation during PCR step.

PCR: The PCR thermocycling was performed using the protocol as described below.

TABLE 3

PCR conditions

| Cycling step | Temperature, ° C. | Time | Ramp Rate | Number of Cycles |
|---|---|---|---|---|
| Enzyme activation | 95 | 10 sec | 2° C./sec | 1 |
| Denaturation | 94 | 30 sec | | 40 |
| Annealing | 60 | 1 min | | 40 |
| Extension | 68 | 1 min | | 40 |
| Enzyme deactivation | 98 | 10 min | | 1 |
| Hold (optional) | 4 | Infinite | | 1 |

Use a heated lid set to 105° C. and set the sample volume to 40 μl

All wells should be observed visually after PCR and before reading the plate on droplet reader. The copy numbers observed during droplet reading may not be real if there is any well where sample is evaporated because of improper sealing. It is good to leave the plate in the thermocycler for about 15-20 min after PCR is done. It allows the temperature of the plate to come down at more controlled way and it avoids droplet malformation. Sometimes malformation of the droplets because of the static current can be avoided by touching hand with other metallic surface before taking out the plate from thermocycler. It should be made a routine practice for better reproducibility of the results. The PCR plate can be stored overnight after PCR and reading can be done next day morning if time is limited. However, finishing everything in one day is best practice.

Droplet Reading: The droplet reader (Bio-Rad QX200™ Droplet Reader Catalog No. #1864003) is used to read signal in droplets following the manufacturer's protocol. Note: Discarding Oil waste: The composition of droplet reader oil is proprietary of Bio-Rad. A typical waste profile contains fluorinated oils (95%), water (5%), bleach (<0.5%), proteins, nucleic acids, and fluorescent dye (<0.1%). A proper disposal should be planned accordingly.

Data Analysis: The copy number calculations should be done following the manufacturer's guidelines. An example of the dPCR ctHPVDNA assay readout is shown in FIG. 1A. The following parameters were set for calculation of FAM-single positive, HEX-single positive, and FAM+HEX double positive droplets. In the FAM channel, a cutoff of 700 is used to separate the negative from positive droplets. Similarly in the HEX channel, a cutoff of 3000 is used to separate the negative from positive droplets. The FAM+ HEX double positive droplets are those with >700 fluorescence intensity in the FAM channel and >3000 fluorescence intensity in the HEX channel. The double negative droplets have FAM fluorescence <700 and HEX fluorescence <3000.

Poisson statistics is used to calculate the copies of each fragment in the reaction individually, using the following formula:

$$\#copies = \#total\ droplets * \ln(\#total\ droplets / \#signal\ negative\ droplets).$$

This is calculated first for fragment 1 (FAM positive) and for fragment 2 (HEX positive).

Extensive control assays have been run to determine the level of experimental noise. Based on these controls, the following criteria were used to determine the number of copies of the target fragment (s) in the assay reaction.

TABLE 4

| Control Criteria | |
| --- | --- |
| HPV16 copies/20 μl reaction | Considered as |
| 0 | Zero |
| Below 3 | False positive and should be considered as zero |
| 3-5 | Assay should be repeated to confirm the value |
| Above 5 | Considered as positive for HPV16 |
| Any positive value in follow up patient when previous HPV16 values are negative | Assay should be repeated to confirm the value |

Figure 1B:
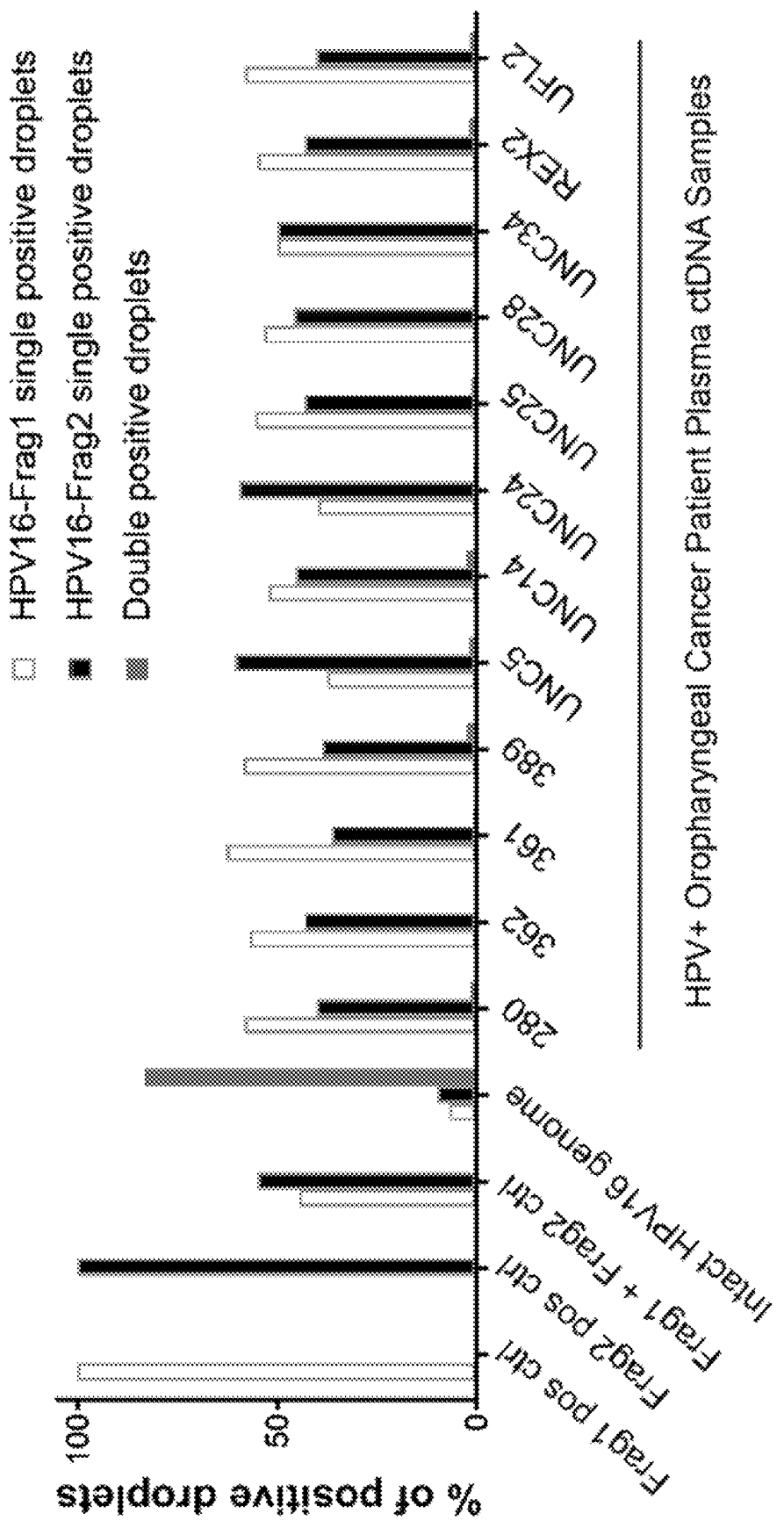

These copy number values can be used to calculate the frequency of a droplet possessing the target fragment: Pr (frag)=(#positive droplets/#total droplets). The frequency of double-positive droplets that are expected if the sample consists of fragmented, circulating tumor viral DNA is estimated as: Pr (double positive)=Pr (frag1)*Pr (frag2). In contrast, if the Pr (dual positive)>2*Pr (frag1)*Pf (frag2), then the sample was considered to contain non-fragmented viral DNA that is not tumor-derived. If Pr (double positive) >Pr (frag1) or Pr (double positive)>Pr (frag2) it was interpret that the sample is negative for circulating tumor-derived viral nucleic acids. If Pr (frag1) AND Pr (frag2)>2*Pr (double positive), then the sample was considered positive for circulating tumor-derived viral nucleic acids, although there is evidence for coexistent non-tumor derived viral nucleic acids. Raw data for this assay applied to experimental controls and plasma DNA from a cohort of 12 patients with HPV+ oropharyngeal cancer is shown in FIG. 1A-1B.

For the HPV16 F1 assay, cutoff of 700 was set on y-axis (FAM channel). Any droplets above 700 are considered as positive droplets for HPV16. For the HPV16 F2 assay, a cutoff of 3000 was set on x-axis (Hex channel). Any droplet above 3000 was considered as positive droplet for HPV16 F2. Occasionally, the patterns of the dPCR readout look unusual. This can be because of a bad sample (unanalyzable cfDNA) or a bad dPCR run. Such sample should be repeated to fix the problem. Data from such samples cannot be used for interpretation. If sample quality is not improved with any available strategies then sample should be categorized as unanalyzable DNA or bad sample. Some strategies to improve the sample quality are as below. The presence of Heparin in the blood sample can interfere with the dPCR reaction. Treating the sample with Bacteroides Heparinase I (New England Biolabs cat no. #P0735S) using manufacturer's protocol improves the quality of sample. Excessive hemolysis sometimes interferes with the dPCR. An improvement has been observed in the assay readout by adding 0.4% bovine serum albumin Some of the representative dot plots from bad samples are provided as separate file with suggested solutions.

Using an endogenous genomic sequence as a positive control for the dPCR reaction is essential for validating sample quality. dPCR-based detection of a target sequence in the ESR1 gene was utilized as a positive control for sample quality. The assay is described below:

TABLE 5

| Variant | Primers and Probes |
| --- | --- |
| Genomic Control (ESR1 locus) | 132_CtrlESR1_F2: ATCTGTACAGCATGAAGTGCAAGA (SEQ ID NO: 7) |
| | 133_CtrlESR1_R2: CTAGTGGGCGCATGTAGGC (SEQ ID NO: 8) |
| | 094_CtrlESR1_LNA2- TET_probe_WT: T(+C)(+T(+A)T(+G)(+A)(+C)CTG (SEQ ID NO: 9) |

"(+N)" denotes LNA™ base

TABLE 6

| Setting PCR Reaction | | | | |
| --- | --- | --- | --- | --- |
| Component | Working stock | Final conc. | 1× (sample) | 1× (NTC) |
| Forward primer | 22.5 μM | 0.9 μM | 1 μl | 1 μl |
| Reverse primer | 22.5 μM | 0.9 μM | 1 μl | 1 μl |
| Probe | 6.25 μM | 0.25 μM | 1 μl | 1 μl |
| BSA | 10% | 0.4% | 1 μl | 1 μl |
| dPCR Supermix | 2× | 1× | 12.5 μl | 12.5 μl |
| DNA sample | Neat/diluted | N/A | 8.5 μl | — |
| PCR grade Water | Adjustable | N/A | — | 8.5 μl |
| Total | | | 25 μl | 25 μl |

TABLE 7

| PCR Conditions | | | | |
| --- | --- | --- | --- | --- |
| Cycling step | Temp, ° C. | Time | Ramp Rate | Number of Cycles |
| Enzyme activation | 95 | 10 sec | 2° C./sec | 1 |
| Denaturation | 94 | 30 sec | | 40 |
| Annealing/Extension | 60 | 1 m in | | 40 |
| Enzyme deactivation | 98 | 10 min | | 1 |
| Hold (optional) | 4 | Infinite | | 1 |

Use a heated lid set to 105° C. and set the sample volume to 40 μl

Work Flow for the Analysis of Plasma DNA Samples:
1) Test samples using ESR1 genomic control dPCR assay, to evaluate amplifiable DNA and sample concentration.
2) Test the samples for the dual fragment HPV16 assay (HPV16ZENv2)
4) If sample is negative for HPV16 then perform the HPV multiplexed assay (HPVmultiplexed_v1)
5) Perform the duplex assay to know specific HPV variant Example 2: Multiplexed dPCR Assay to Detect 5 Distinct HPV Sub-Strains (HPVmultiplexed_v1)

The disclosed methods were applied to sub-strains of a given virus. While the embodiment here relates to sub-strains of the HPV virus, the method can be readily applied to other viral sub-strains using established techniques known to those versed in the field. Variants included in the described embodiment of the method are HPV16, HPV18, HPV31, HPV33 and HPV35

HPV16 probe was tagged with FAM-Zen while others with HEX (LNA version).

TABLE 8

| Primers and Probes | |
|---|---|
| Variant | Primers and Probes |
| HPV16 | 283_ HPV-16_For:<br>TGACTCTACGCTTCGGTTG<br>(SEQ ID NO: 1) |
| | 284_ HPV-16_Rev:<br>GCCCATTAACAGGTCTTCC<br>(SEQ ID NO: 2) |
| | 420 HPV-16_Probe_FAM-ZEN_v2:<br>CGTACAAAGCACACACGTAGACATTCGTAC<br>(SEQ ID NO: 3) |
| HPV18 | 401_HPV18_For:<br>TGAAGCCAGAATTGAGCTAG<br>(SEQ ID NO: 10) |
| | 422_ HPV18_Rev_v2:<br>AGGACAGGGTGTTCAGAA<br>(SEQ ID NO: 11) |
| | 403_HPV18_LNA_H EX-Probe:<br>CA(+G)A(+C)(+G)AC(+C)TTCG<br>(SEQ ID NO: 12) |
| HPV31 | 404_HPV31_For:<br>AGCACACAAGTAGATATTCGC<br>(SEQ ID NO: 13) |
| | 405_HPV31_Rev:<br>TAGTAGAACAGTTGGGGCA<br>(SEQ ID NO: 14) |
| | 406_HPV31_LNA_HEX-Probe:<br>TAA(+C)(+A)G(+C)T(+C)(+T)TG(+C)<br>(SEQ ID NO: 15) |
| HPV33 | 407_HPV33_For:<br>TAACACCACAGTTCGTTTATGT<br>(SEQ ID NO: 16) |
| | 423_ HPV33_Rev_v2:<br>ACAATATTCACTGTGCCCATA<br>(SEQ ID NO: 17) |
| | 418_HPV33_LNA_HEX-Probe_v2:<br>TG(+A)C(+C)(+T)A(+C)G(+A)(+A)CC<br>(SEQ ID NO: 18) |
| HPV35 | 410_HPV35_For:<br>TGAGGCGACACTACGTC<br>(SEQ ID NO: 19) |
| | 411_HPV35_Rev:<br>GTGCCCATTAATAAATCTTCCAA<br>(SEQ ID NO: 20) |
| | 419_HPV35_LNA_HEX-Probe_v2:<br>AG(+A)G(+C)(+A)CA(+C)(+A)CAT<br>(SEQ ID NO: 21) |

"(+N)" denotes LNA™ base

Reaction Mixture

Primer mixture: Mix equal volume of 10 primers each at 100 μM (each primer diluted 1:10 in the mixture). Probe mixture: Mix 6.25 μl of each of five probes in a tube and add 68.75 μl water (final concentration will be 6.25 μM each in 100 μl volume)

TABLE 9

| Reaction Mixtures | | | | |
|---|---|---|---|---|
| Component | Working stock | Final Conc. | 1× (sample) | 1× (NTC) |
| Primers Mixture | 10 μM each | 0.9 μM each | 2.25 μl | 2.25 μl |
| Probes Mixture | 6.25 μM each | 0.125 μM each | 0.5 μl | 0.5 μl |
| Albumin | 10% | 0.4% | 1 μl | 1 μl |
| Betaine | 5M | 0.4 μM | 2 μl | 2 μl |
| Trehalose | 1.25M | 0.16M | 3.2 μl | 3.2 μl |
| dPCR Supermix | 2× | 1× | 12.5 μl | 12.5 μl |
| DNA sample | Neat/Diluted | N/A | 3.55 μl | — |
| PCR grade Water | Adjustable | N/A | — | 3.55 μl |
| Total | | | 25 μl | 25 μl |

TABLE 10

| PCR conditions | | | | |
|---|---|---|---|---|
| Cycling step | Temperature, ° C. | Time | Ramp Rate | Number of Cycles |
| Enzyme activation | 95 | 10 sec | 2° C./sec | 1 |
| Dentaturation | 94 | 30 sec | | 40 |
| Annealing | 60 | 1 min | | 40 |
| Extension | 68 | 1 min | | 40 |
| Enzyme deactivation | 98 | 10 min | | 1 |
| Hold (optional) | 4 | Infinite | | 1 |

Use a heated lid set to 105° C. and set the sample volume to 40 μl

Note: An LNA™-FAM probe was also designed to amplify common region in all known HPV16 variants with same primers (No. 283 & 285). This was not used in the multiplexed assay.

413_HPV16_LNA_FAM-CommonProbe:
(SEQ ID NO: 22)
CA(+C)A(+C)(+G)(+T)A(+G)(+A)CAT

Example 3: Duplex dPCR Assay to Detect Specific HPV Variants (HPV_18&33_v1 and HPV_31&35_v1)

This assay was designed to know the identity of specific HPV variants in patient samples.

TABLE 11

| Primers and Probes | | |
|---|---|---|
| | Variant | Primers Probe |
| Set 1 | HPV18 &<br>HPV33 | 401_HPV18_For:<br>TGAAGCCAGAATTGAGCTAG<br>(SEQ ID NO: 10) |
| | | 422_ HPV18_Rev_v2:<br>AGGACAGGGTGTTCAGAA<br>(SEQ ID NO: 11) |
| | | 407_HPV33_For:<br>TAACACCACAGTTCGTTTATGT<br>(SEQ ID NO: 16) |
| | | 423_ HPV33_Rev_v2:<br>ACAATATTCACTGTGCCCATA<br>(SEQ ID NO: 17) |

TABLE 11-continued

| Primers and Probes | | |
| --- | --- | --- |
| Variant | Primers | Probe |
| | | 403_HPV18_LNA_HEX-Probe: CA(+G)A(+C)(+G)AC+CTTCG (SEQ ID NO: 12) |
| | | 426_HPV33_LNA_FAM-Probe: TG(+A)C(+C)(+T)A(+C)G(+A) (+A)CC (SEQ ID NO: 18) |
| Set 2 | HPV31 & HPV35 | 404_HPV31_For: AGCACACAAGTAGATATTCGC (SEQ ID NO: 13) |
| | | 405_HPV31_Rev: TAGTAGAACAGTTGGGGCA (SEQ ID NO: 14) |
| | | 410_HPV35_For: TGAGGCGACACTACGTC (SEQ ID NO: 19) |
| | | 411_HPV35_Rev: GTGCCCATTAATAAATCTTCCAA (SEQ ID NO: 20) |
| | | 406_HPV31_LNA_HEX-Probe: TAA(+C)(+A)G(+C)T(+C)(+T)TG(+C) (SEQ ID NO: 15) 427_HPV35_LNA_FAM-Probe: AG(+A)G(+C)(+A(CA(+C)(+A)CAT (SEQ ID NO: 21) |

"(+N)" denotes LNA™ base

Reaction Mixture

Primer mixture: Mix 22.5 μl of each of the four primers and add 10 μl water (22.5 μM each primer in the mixture). Probe mixture: Mix 6.25 μl of both probes in a tube and add 87.5 μl water (final concentration will be 6.25 μM each in 100 μl volume).

TABLE 12

| Reaction Conditions | | | | |
| --- | --- | --- | --- | --- |
| Component | Working stock | Final Conc. | 1× (sample) | 1× (NTC) |
| Primers Mixture | 22.5 μM each | 0.9 μM each | 1 μl | 1 μl |
| Probes Mixture | 6.25 μM each | 0.125 μM each | 0.5 μl | 0.5 μl |
| Albumin | 10% | 0.4% | 1 μl | 1 μl |
| Betaine | 5M | 0.4 μM | 2 μl | 2 μl |
| Trehalose | 1.25M | 0.16M | 3.2 μl | 3.2 μl |
| dPCR Supermix | 2× | 1× | 12.5 μl | 12.5 μl |
| DNA sample | Neat/Diluted | N/A | 4.3 μl | — |
| PCR grade Water | Adjustable | N/A | — | 4.3 μl |
| Total | | | 25 μl | 25 μl |

TABLE 13

| PCR conditions | | | | |
| --- | --- | --- | --- | --- |
| Cycling step | Temperature, ° C. | Time | Ramp Rate | Number of Cycles |
| Enzyme activation | 95 | 10 sec | 2° C./sec | 1 |
| Dentaturation | 94 | 30 sec | | 40 |
| Annealing | 60 | 1 m in | | 40 |
| Extension | 68 | 1 min | | 40 |

TABLE 13-continued

| PCR conditions | | | | |
| --- | --- | --- | --- | --- |
| Cycling step | Temperature, ° C. | Time | Ramp Rate | Number of Cycles |
| Enzyme deactivation | 98 | 10 min | | 1 |
| Hold (optional) | 4 | Infinite | | 1 |

Use a heated lid set to 105° C. and set the sample volume to 40 μl

Figure 2:
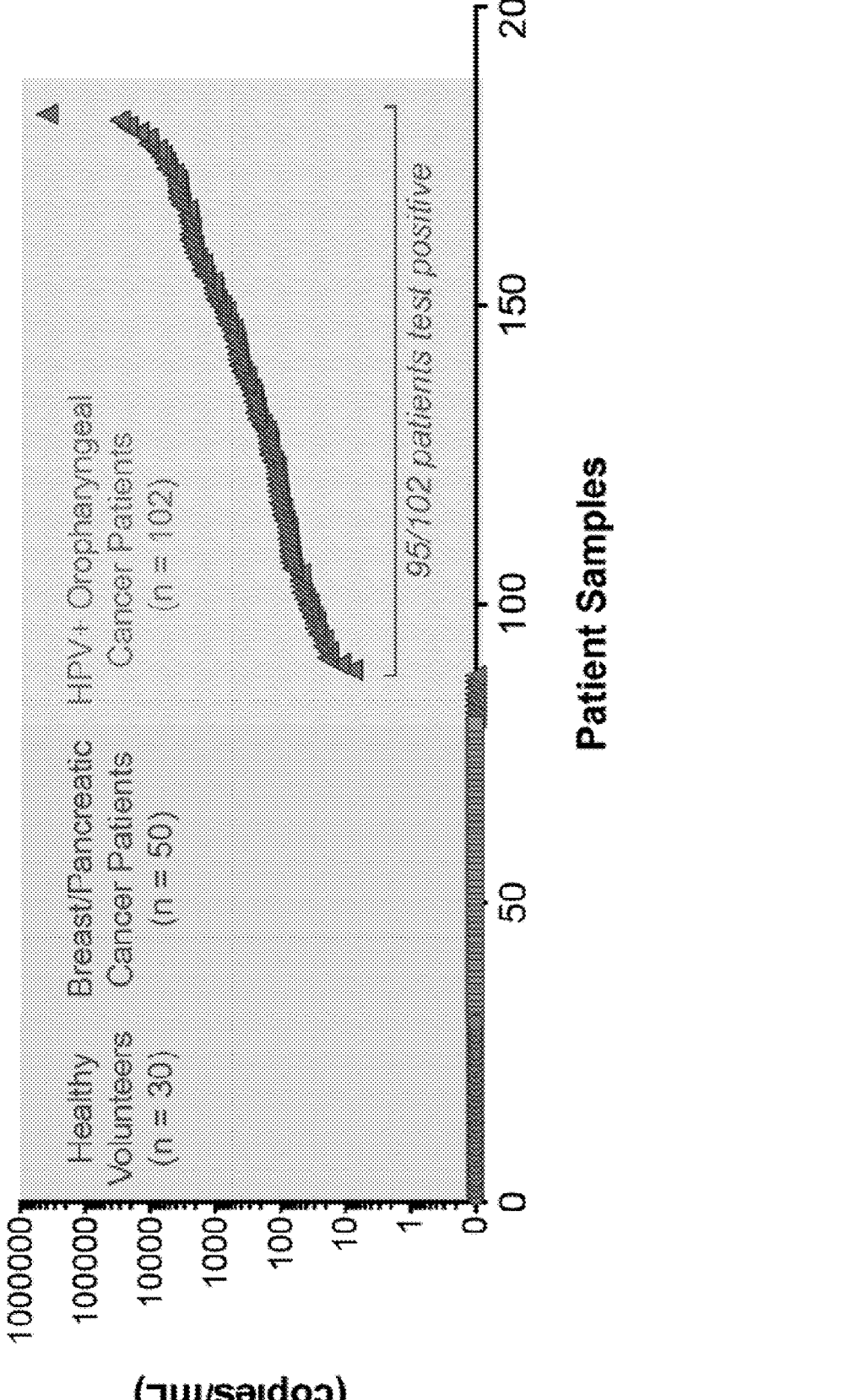
FIG. 2: Analysis of a large cohort of patient blood samples using the HPV blood assay described in Example 1. There was no HPV tumor viral DNA detected in 30 healthy volunteers and 50 patients with HPV negative cancers (breast and pancreatic). In contrast, 95/102 patients with a diagnosis of HPV positive oropharyngeal cancer have pre-treatment circulating tumor HPV DNA in plasma using the blood test described here. The observed number of copies of HPVDNA detected by the assay is also indicated, highlighting the dynamic range of the test. Based on this data, estimates for assay specificity and sensitivity are 100% and 93%, respectively, at the time of initial diagnosis.

Example 4: Application to Patient Blood Samples in Prospective Clinical Trials Blood samples were analyzed from healthy volunteers, non-virus associated cancer, and HPV+ cancer. Circulating tumor HPV DNA copy numbers, as measured using the assay technology described in Example 1, are shown in FIG. 2. These data indicate that the ctHPVDNA blood test has 100% specificity and 93% sensitivity for identifying patients with HPV+ cancer.

Blood samples were analyzed from patients enrolled in two prospective phase II clinical trials. The disclosed method for specifically detecting tumor-derived viral HPV DNA in the blood was integrated into the design of both of these clinical trials. The findings from these longitudinal clinical studies illustrate the applicability and utility of the disclosed method both for personalizing patient therapy and for cancer surveillance.

Summary of patient cohort and clinical trial design. Two prospective phase II clinical trials were completed that evaluated the efficacy of a de-intensified chemo-radiation therapy regimen in low risk OPSCC. In LCCC 1120 (NCT01530997) 45 patients were treated with de-intensified CRT. Eligible patients had HPV-positive and/or p16-positive OPSCC, T0-T3, N0-N2c, M0, and <10 pack years of smoking. Patients received 60 Gy of Intensity Modulated Radiotherapy (IMRT) with concurrent weekly intravenous cisplatin (30 mg/m²). All patients had biopsy of the primary site and underwent a selective neck dissection to encompass nodal level(s) that were positive pre-treatment, within 4 to 14 weeks after CRT. The primary endpoint of LCCC 1120 was the rate of pCR, which was 86% (37/43) and the 3-year cancer control and overall survival was 100% and 95%, respectively. In addition to excellent cancer control, patient had less toxicity and reported excellent quality of life and lower symptom burden as compared to standard of care CRT (70Gy). In a second-generation phase 2 study (LCCC 1413, NCT02281955) a 12-week post-treatment PET/CT was used to guide the use of biopsy/neck dissection (i.e. post CRT surgical evaluation was not mandatory, but guided by imaging). Of the 113 patients enrolled, 82 patients have had a minimum of 1-year follow-up and the 2-year actuarial cancer control and overall survival in these 82 patients is 90% and 95% respectively (again excellent results). Patients continue to report good recovery of quality of life at 1 year, and thus supports the concept that dose de-escalation can improve the therapeutic ratio. A third generation phase 2 study (LCCC 1612, NCT03077243) is currently being conducted, and has enrolled 53 of an expected 120 patients. Blood samples from 113 patients were prospectively analyzed to detect tumor-derived plasma viral HPV DNA.

Levels of tumor-derived viral HPV DNA in the blood, as quantified by the disclosed method, correlate significantly with HPV viral DNA in primary tumors. In 63 patients with HPV-OPSCC, serial levels of tumor-derived viral HPV DNA (pre- and weekly during-RT) were prospectively quantified in patient blood samples using the disclosed method (FIG. 3A). 49 patients had detectable tumor-derived viral HPV DNA in the circulation prior to treatment. In all 49 patients, the levels of circulating HPV DNA had dropped significantly by week 6 (FIG. 3B) following the initiating of chemo-radiation therapy, diminishing to undetectable levels in a majority (90%, n=44/49) of patients by the end of the therapeutic regimen. Across patients, the peak levels of tumor-derived viral HPV DNA in the blood, ranged from 10 copies/mL to ~30,000 copies/mL. Moreover, distinct clearance kinetics of tumor-derived viral HPV DNA was observed in the blood during CRT treatment. In one group there was rapid clearance kinetics (FIG. 3C), with >95% of the peak tumor-derived viral HPV DNA in the blood being cleared by day 28 of therapy. In a second group there was delayed clearance of tumor viral HPV DNA in the blood (FIG. 3D), which may be associated with poor or delayed response to therapy.

The disclosed method was further validated by correlating levels of tumor-derived viral HPV DNA in the blood with analysis of matched primary tumors in a cohort of 20 patients (FIG. 4). Normalized HPV DNA copies in tumor biopsy material correlates strongly with HPV DNA copies as measured by next-generation sequencing (FIG. 4A). Moreover, the quantity of tumor-derived viral HPV DNA in blood correlates significantly with HPV DNA copy number in the matched tumor biopsy, after normalizing to the overall tumor burden in the patient (FIG. 4B). Using next-generation sequencing, cancers with integration of HPV into the cancer cell genome were identified (FIG. 4C-4D). Higher copy number of HPV DNA in tumor biopsy material correlated with a high likelihood of episomal (non-integrated) HPV DNA in the matched primary tumor (FIG. 4E). Similarly, higher copy numbers of tumor-derived viral HPV DNA in the blood correlated with a higher likelihood of episomal (non-integrated) HPV DNA in the matched primary tumor (FIG. 4F). These findings validate the disclosed methods by establishing that the quantification of viral DNA in the blood using the disclosed methods correlates significantly with measurements of viral DNA in matched tumor tissue. These observations also demonstrate the disclosed method can monitor the presence and clearance of tumor-derived HPV viral DNA in longitudinal analysis of patient blood samples.

Figure 5A:
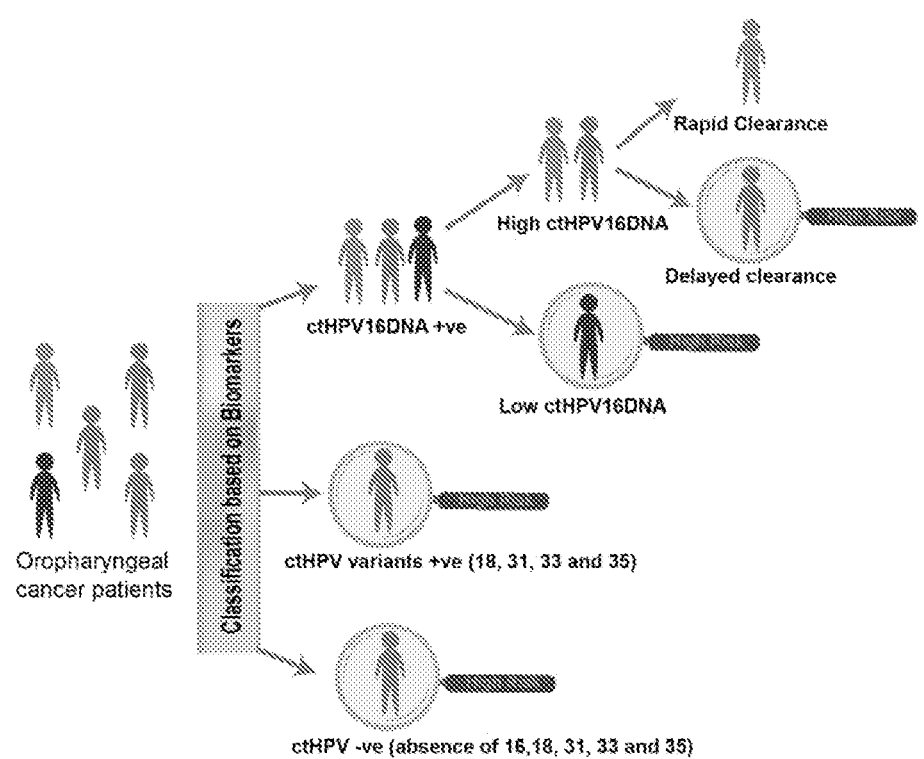
FIG. 5A-B.
Figure 5B:
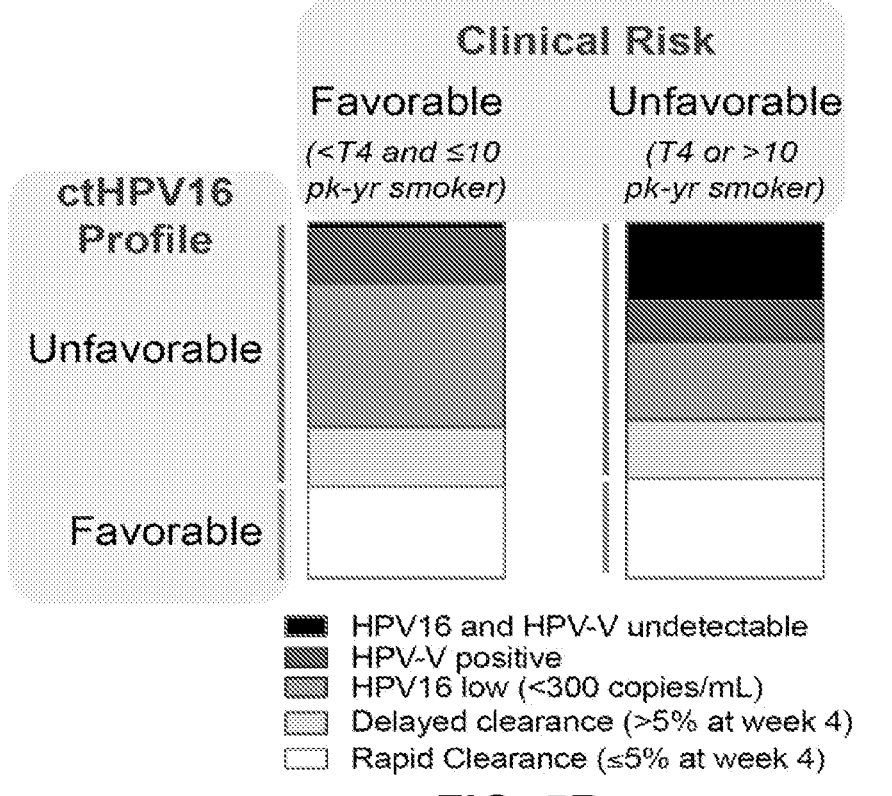
Figure 6A:
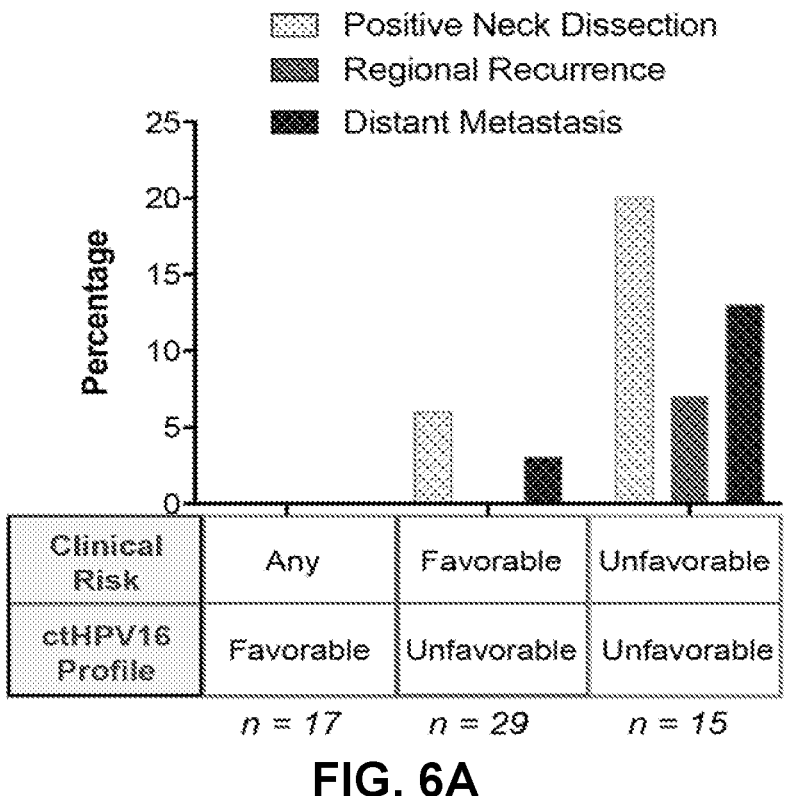
FIG. 6A-B.
Figure 6B:
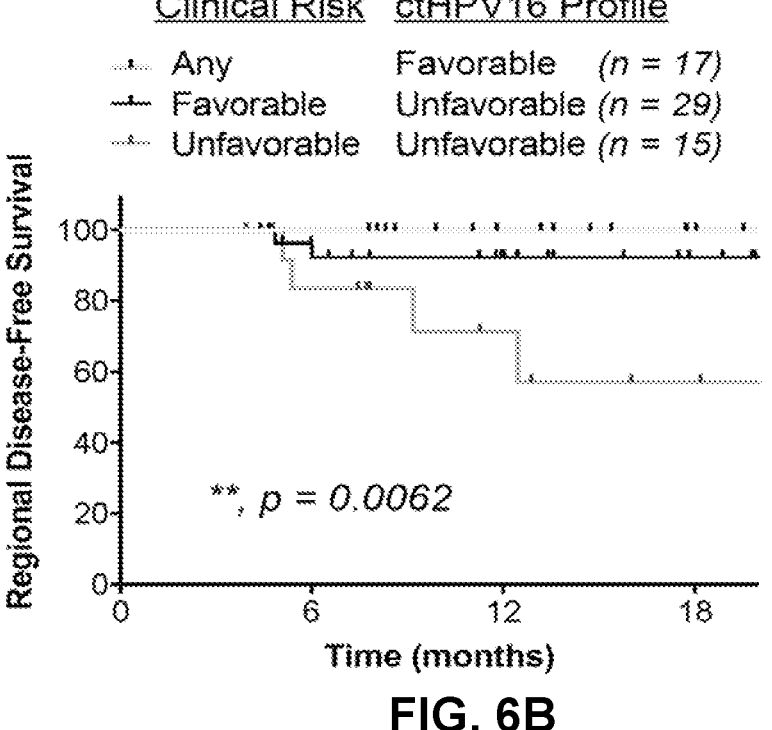

Predict clinical risk in cancer patients. The disclosed method was applied to monitor tumor-derived viral HPV DNA in the blood before and during therapy in 63 patients enrolled in the clinical trial described above. A Favorable Profile was defined as having abundant ctHPV16DNA peak levels of tumor-derived viral HPV DNA in the blood (>200 copies/mL) and rapid clearance kinetics (2% of the peak value by week 4) (FIG. 5A). 18 out of 63 evaluable patients (29%) had a Favorable Profile (FIG. 5B), and none of these 18 patients have recurred (regardless of smoking status) (FIG. 6A-B). An Unfavorable Profile was defined as (i) undetectable pre-treatment tumor-derived viral HPV DNA in the blood, (ii) low peak values of tumor-derived viral HPV DNA in the blood (200 copies/mL), or (iii) >2% of the peak value by week 4 (40Gy) (FIG. 5A-B). Remarkably, patients with a Favorable Profile exhibited 100% disease control in non-smokers (60Gy) and heavy smokers (60-70Gy). In contrast, heavy smokers (>10 pack year) with an Unfavorable Profile had a very poor regional disease control rate of 45% at 12 months after completing therapy (FIG. 6A-B). These observations demonstrate the clinical utility of applying the disclosed method to quantify tumor-derived viral DNA in the blood as a biomarker to predict clinical risk among virus-associated cancer patients. Moreover, these findings indicate that a real-time assessment of circulating tumor-derived viral DNA can be utilized to personalize the intensity of therapy for patients based on their inferred risk.

Figure 7:
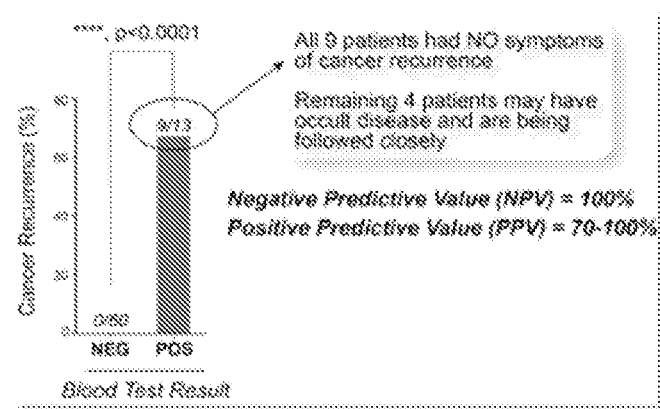
FIG. 7: The ctHPVDNA test described here was applied to a cohort of 73 patients who had completed treatment for HPV+ Oropharyngeal cancer. These patients had no evidence of disease and were clinically asymptomatic. They were monitored with the ctHPVDNA blood test at each follow up visit. 60 out of 73 patients had undetectable ctHPVDNA at all follow up visits, and none of these patients developed disease recurrence during the follow up period. In contrast, 13 out of 73 patients developed a positive ctHPVDNA blood test during the clinical follow up period. 9 out of these 13 patients have also developed clinically evident disease recurrence. The ctHPVDNA blood test was positive up to 6 months prior to identification of recurrent disease on a diagnostic radiology scan. The remaining 4 patients who have a positive blood test are being closely monitored for possible disease recurrence.

Early detection of HPV-positive cancer recurrence in healthy patients that are asymptomatic and considered disease-free using existing clinical procedures. The typical surveillance schedule after chemo-radiation therapy is clinical examinations (physical examination and fiber optic nasopharyngolaryngoscopy) every 2 to 6 months for the first 5 years. Most head and neck oncologist also obtain PET/CT every 6 to 12 months. There are currently no available surveillance blood tests for patients with HPV-associated OPSCC. The availability of highly sensitive blood-based surveillance test would aide in early detection of cancer recurrence (prior to clinical or radiographic findings) and improve the value of cancer surveillance in this population by reducing the frequency of office visits and the use of expensive radiological imaging studies. To date 73 patients have been prospectively surveilled with HPV-associated OPSCC (FIG. 7). Blood samples were obtained with each follow-up visit regardless of clinical findings. Plasma ctHPV16DNA has become detectable in follow up after treatment in 13 patients (median copies/ml and range) of which 9 have had clinical/radiographic evidence of cancer recurrence. These patients with detectable ctHPV16DNA after treatment were asymptomatic and had radiographic examinations confirming very early, low volume cancer recurrences. An illustrative case example is presented in FIG. 8. Here, the patient had already completed curative-intent therapy and was completely asymptomatic with no evidence of disease. However, he developed a positive result for tumor-derived viral HPV DNA in the blood in June 2017. Soon thereafter, he was examined by an oncologist and determined to have no evidence of disease. Three months later, he had another follow up visit and the oncologist did not identify any evidence for disease recurrence on physical exam. However, the patient reported some neck/shoulder pain, which was believed to be musculoskeletal in nature. A neck/shoulder MRI was ordered, and on this exam-4 months after the initially positive blood test—an isolated abnormally enlarged lymph node was identified in the neck. This abnormal mass was subsequently biopsied and proven to be recurrent HPV+ oropharyngeal cancer.

There are 4 patients in the study who have detectable HPV DNA in the blood using the disclosed methods, yet have no clinical/radiographic evidence of disease and are being closely followed for recurrence. No cancer recurrences have been detected in patients with undetectable ctHPV16DNA. In summary the negative predictive value and positive predictive value of the plasma ctHPV16DNA assay in detecting cancer recurrence is 100% and 70%, respectively. These observations suggest that plasma ctHPVDNA is exquisitely specific and sensitive for the early detection of HPV-associated cancer. Application of the disclosed method as part of clinical care may improve the effectiveness and reducing the cost of cancer surveillance for patients with HPV-associated oropharyngeal cancer.

Figure 8:
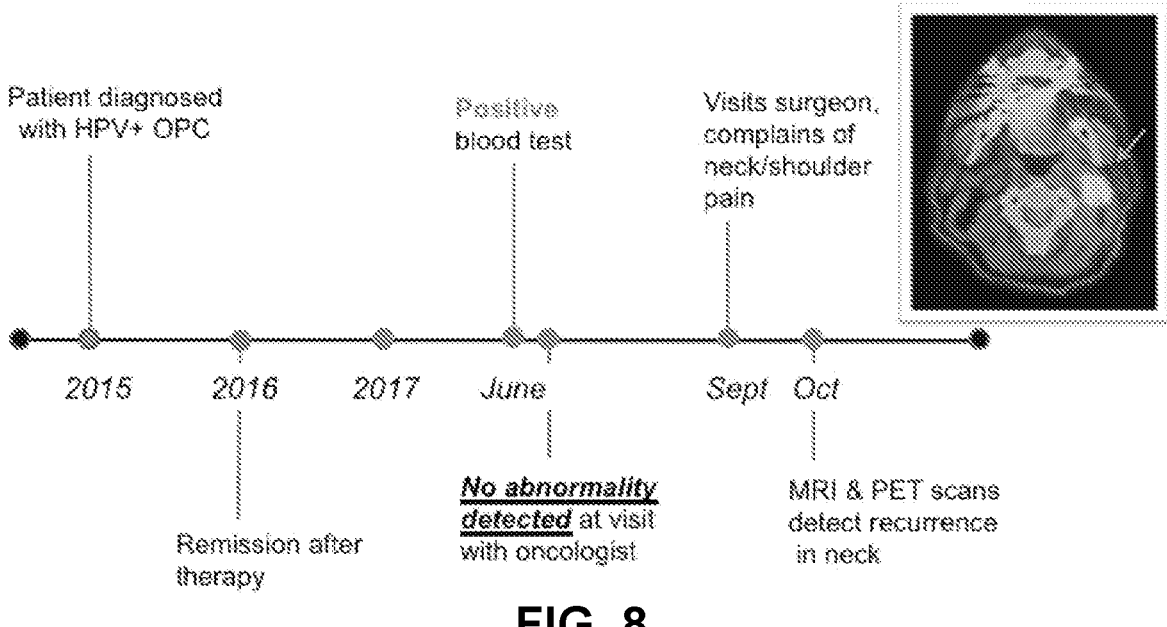
FIG. 8: Case example from the ctHPVDNA surveillance study. This patient was clinically asymptomatic and believed to be cancer-free. In June 2017 he developed a positive ctHPVDNA blood test. Soon thereafter, he was examined by an oncologist and was found to have no evidence of disease. Three months later, he was again examined by a clinician who did not identify any evidence for disease recurrence. However, the patient reported some neck/shoulder pain, which was believed to be musculoskeletal in nature. A neck/shoulder MRI was ordered, and on this exam-4 months after the blood test was positive—an isolated abnormally enlarged lymph node was identified that was subsequently biopsied and consistent with recurrent HPV+ oropharyngeal cancer.

Example 5: Plasma Circulating Tumor HPV16DNA
as a Biomarker for Treatment of HPV-Associated
OPSCC The RTOG 0129 study demonstrated that exposures influence clinical risk in oropharyngeal cancer. HPV-positive patients tend to do well, and HPV-negative patients with extensive smoking history do poorly. Most studies, including RTOG 0129, also demonstrate an intermediate prognosis for HPV+ cancers that develop in heavy smokers. This is shown in FIG. 8.

Genetic biomarkers can improve clinical risk stratification. For example, a subset of tumors in HPV+ non-smokers may be exceptionally sensitive to therapy, whereas, there may be smokers with HPV+ cancers that have more HPV-like biology, and others that may have more tobacco-like biology. Biomarkers may be able to identify these subgroups better than clinical parameters alone.

Plasma ctHPVDNA is detected in a majority of HPV-OPSCC patients. As such, ctHPV DNA can be a biomarker of tumor burden, and as importantly, response kinetics. Plasma circulating tumor HPV DNA can also inform decisions regarding who is appropriate for de-escalated therapy of HPV-associated OPSSC.

A digital PCR assay has been developed for HPV16 DNA that is: highly specific, in that the assay does not cross-detect HPV-18, -31, -33, or 35, and has very low background signal; linear over 5 orders of magnitude in copy number (5-50,000 copies); precise and has exceptional reproducibility; and ultra-sensitive and can detect as few as 6 copies of HPV16 with ~80% sensitivity. This is shown in FIGS. 1A and 1B. FIG. 1A shows an example readout of this assay where positive droplets indicate the presence of individual HPV16 DNA molecules, that are well separated from the negative droplets in a reaction. FIG. 1B shows the 95% confidence interval of a linear regression, demonstrating incredible linearity and precision, with assay variability only becoming an issue in the 10 target copy range. This assay can detect as few as 6 target molecules of HPV16 DNA using an assay threshold that gives no false positives.

A study population including 64 patients with biopsy-proven HPV-positive OPSCC that overexpressed p16 (IHC) and/or were HPV ISH positive. All patients received definitive chemo-radiation (no induction chemo). 54 patients (84%) enrolled in a prospective CRT de-intensification trial (60Gy IMRT+weekly Cisplatin 30 mg/m$^2$). Of these, 46 patients were clinically favorable (<T4 and ≤10 pack-years tobacco), and 18 were clinically unfavorable (T4 or >10 pack-years tobacco). No patients had N3 or M1 disease. Research bloods were collected pre-treatment, weekly during CRT, and at post-treatment clinic visits (~450 blood samples analyzed).

Figure 3A:
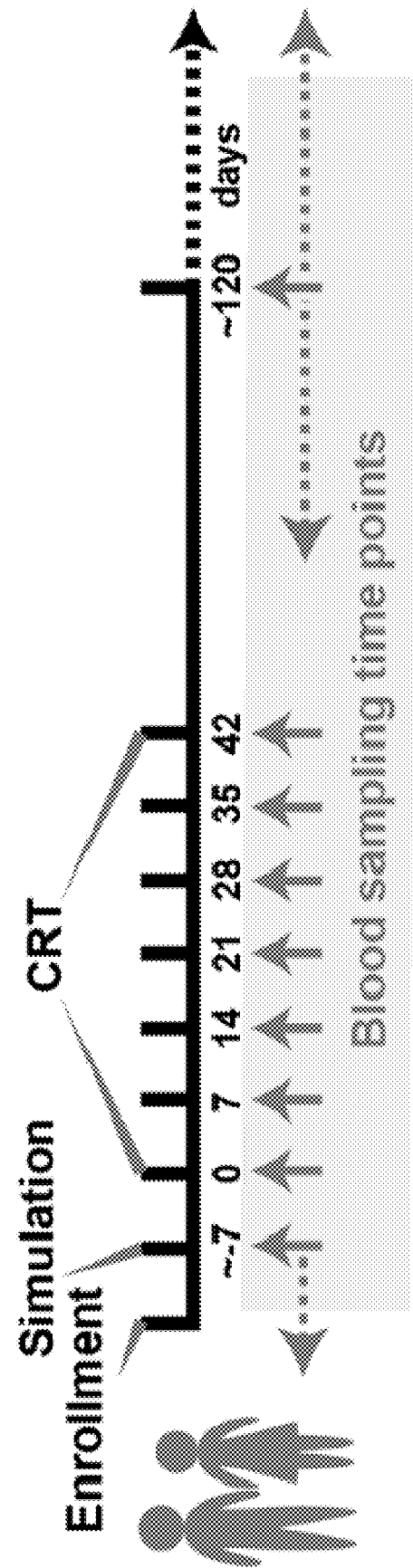
FIGS. 3A-3D.
Figure 3B:
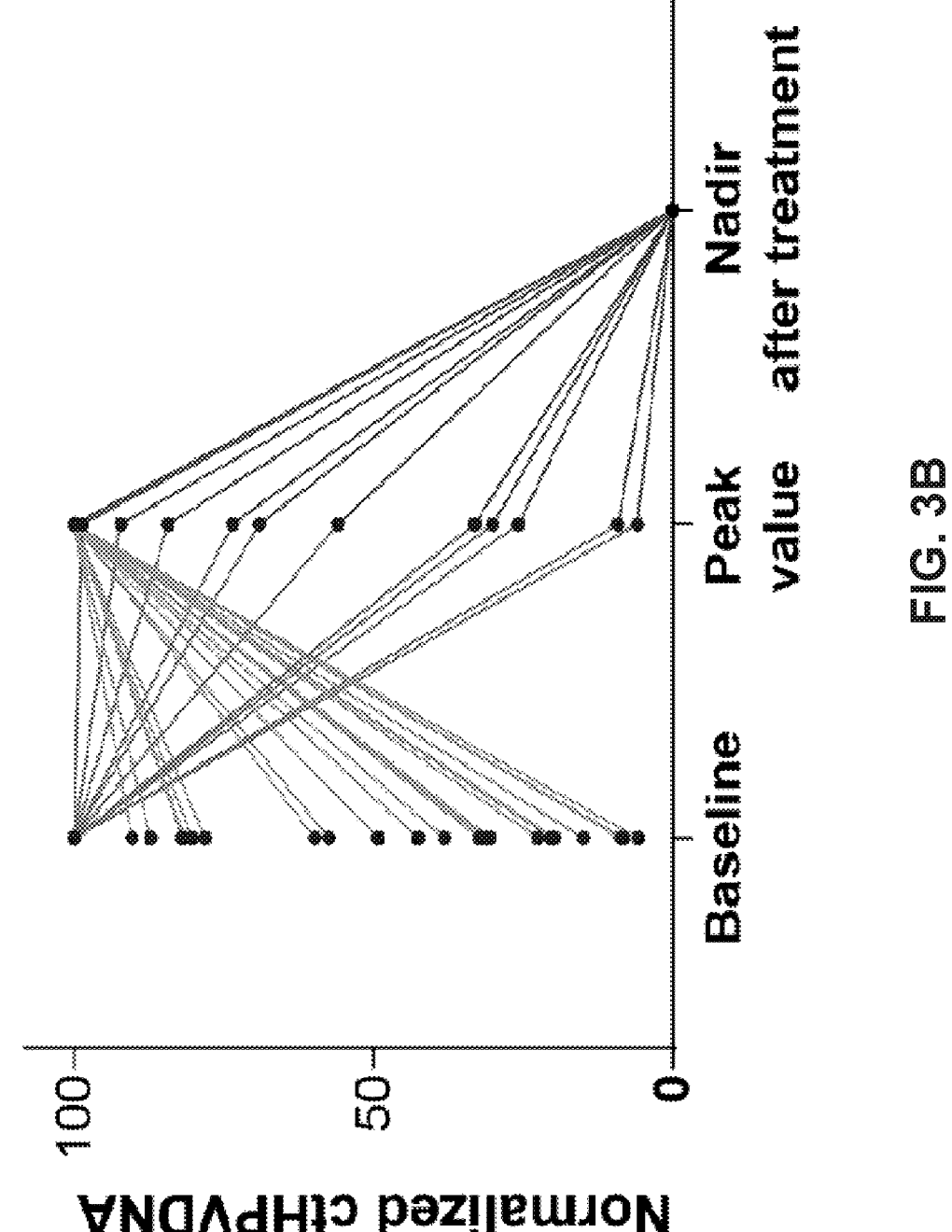

Plasma ctHPV16DNA levels were measured during chemo-radiotherapy. Plasma ctHPV16DNA is responsive to CRT and in most cases is "cleared" after treatment. Its potential as a biomarker of treatment efficacy, and correlation of peak-ctHPV16DNA levels with smoking status, disease burden, and tumor HPV copy number was evaluated. This regimen is shown in FIG. 10, and normalized levels of ctHPV16DNA is depicted in FIG. 3A.

Plasma ctHPV16 DNA was detected in 77% of the patients, and FIG. 11 indicates the peak value for each patient. As shown in FIG. 11, broad range of values was observed, with as few as 10 copies per mL to as high as 30,000 copies per mL being observed. There were also 23% of patients who did not have any detectable HPV16 DNA in plasma. Furthermore, any significant correlation between the amount of HPV16 in plasma and smoking status was not seen.

Figure 3C:
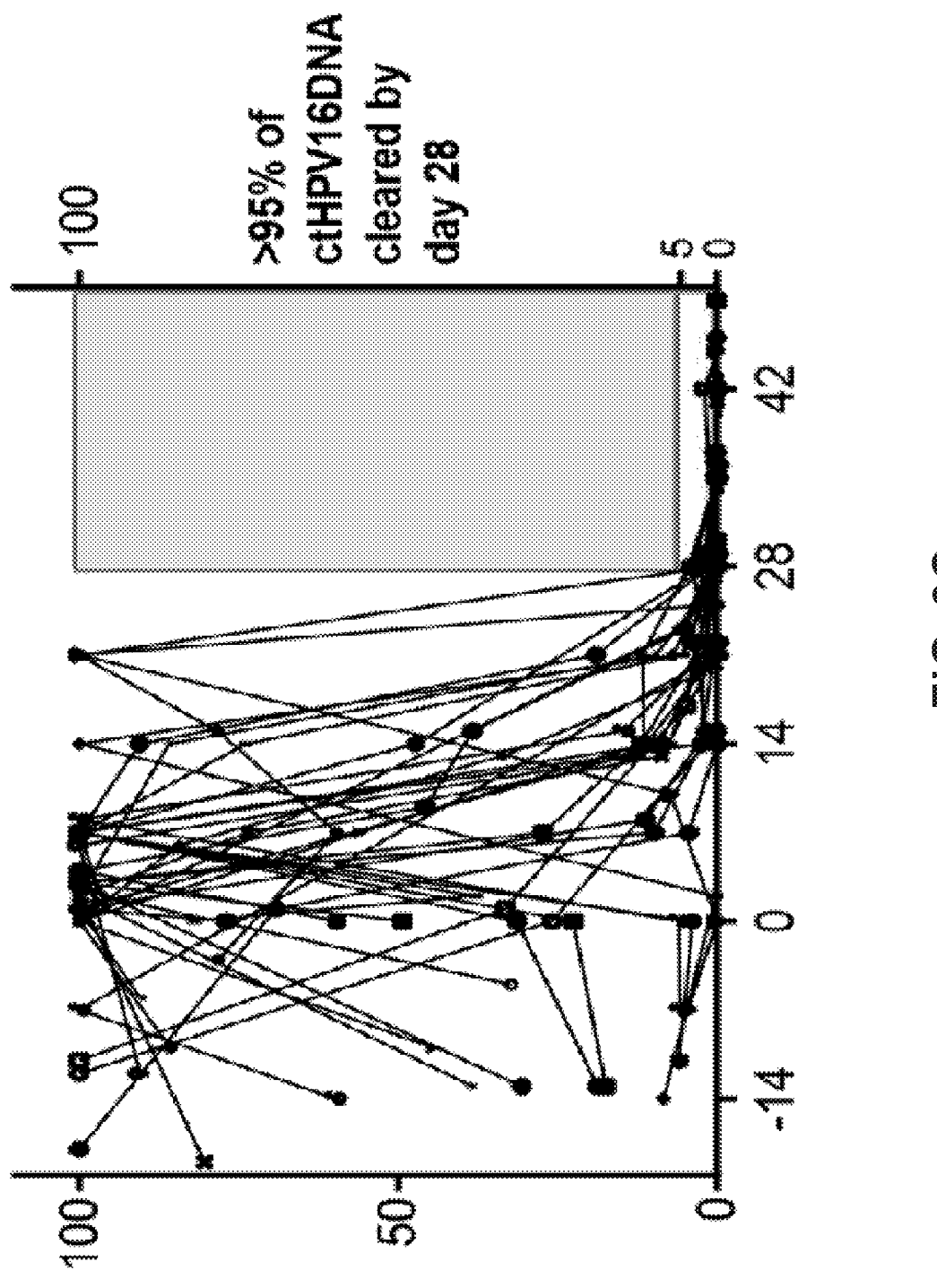
Figure 3D:
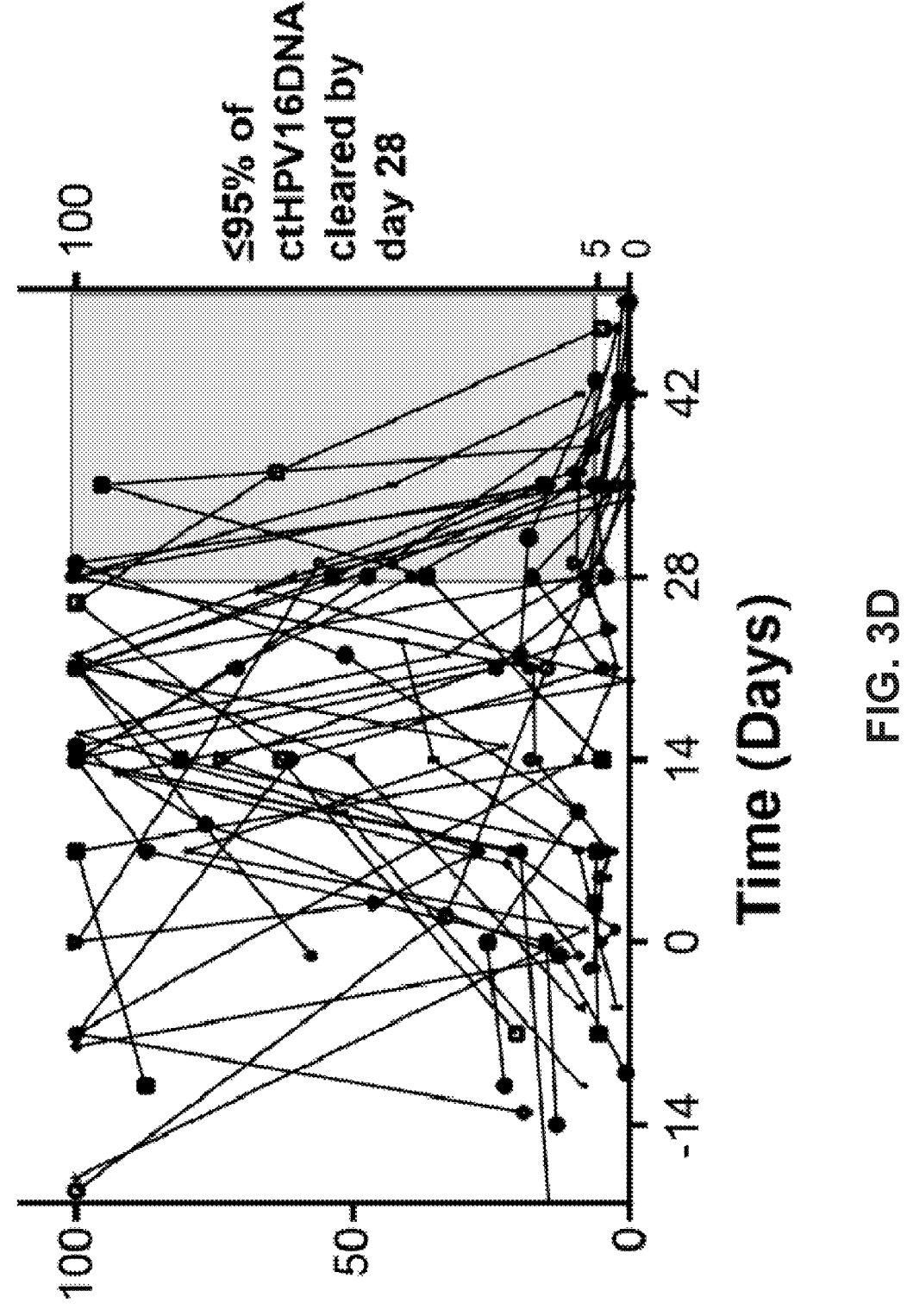
Figure 4A:
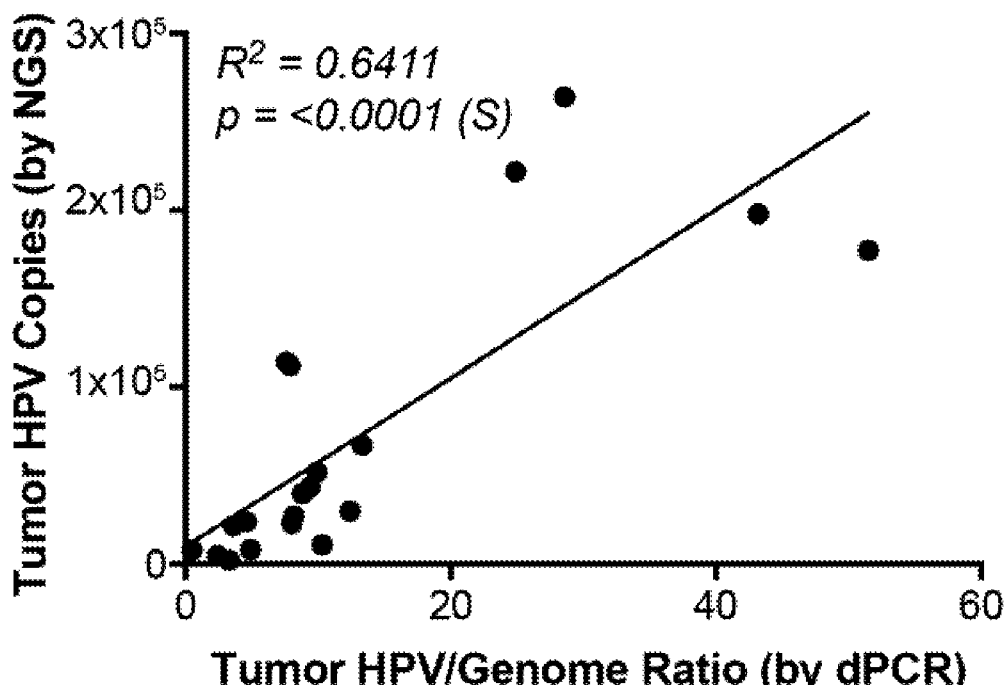
FIG. 4A-F: A subset of 20 patients with HPV+ OPC had next generation sequencing (NGS) analysis of their primary tumor as well as ctHPVDNA analyses of their blood to investigate potential correlation between these assays.
Figure 4B:
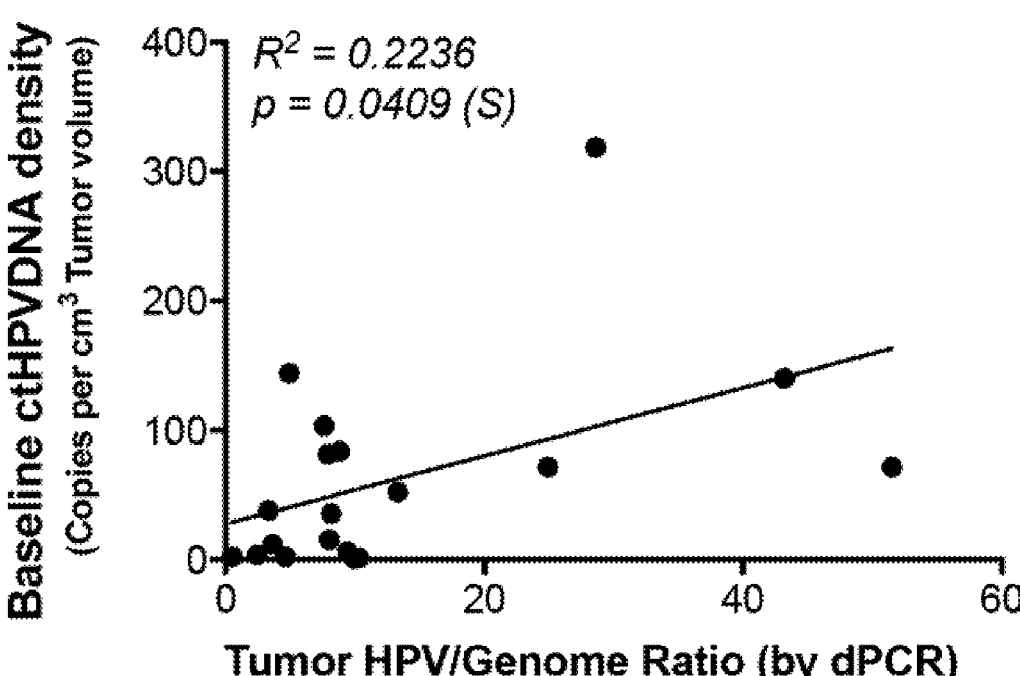
Figure 4C:
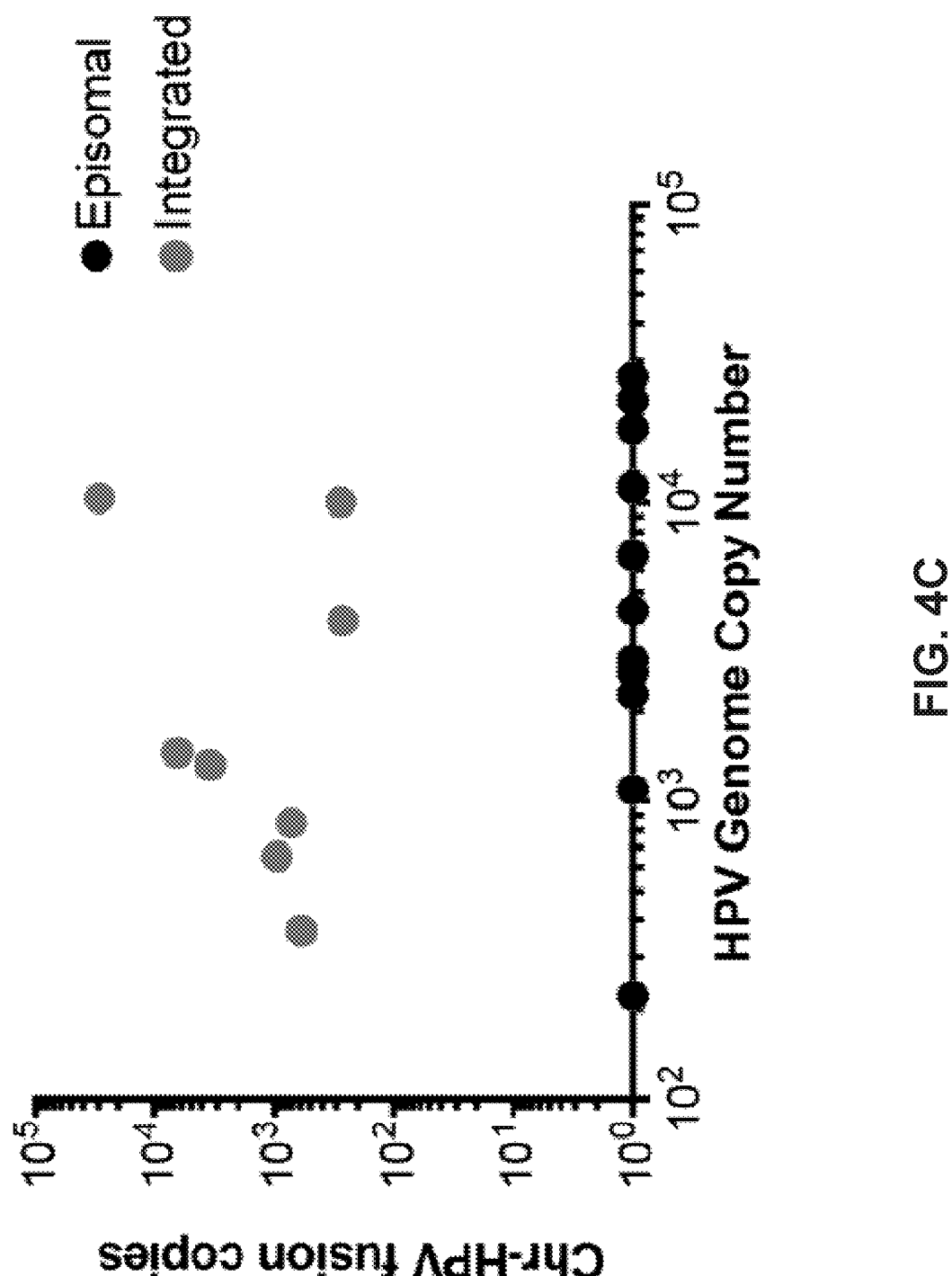
Figure 4D:
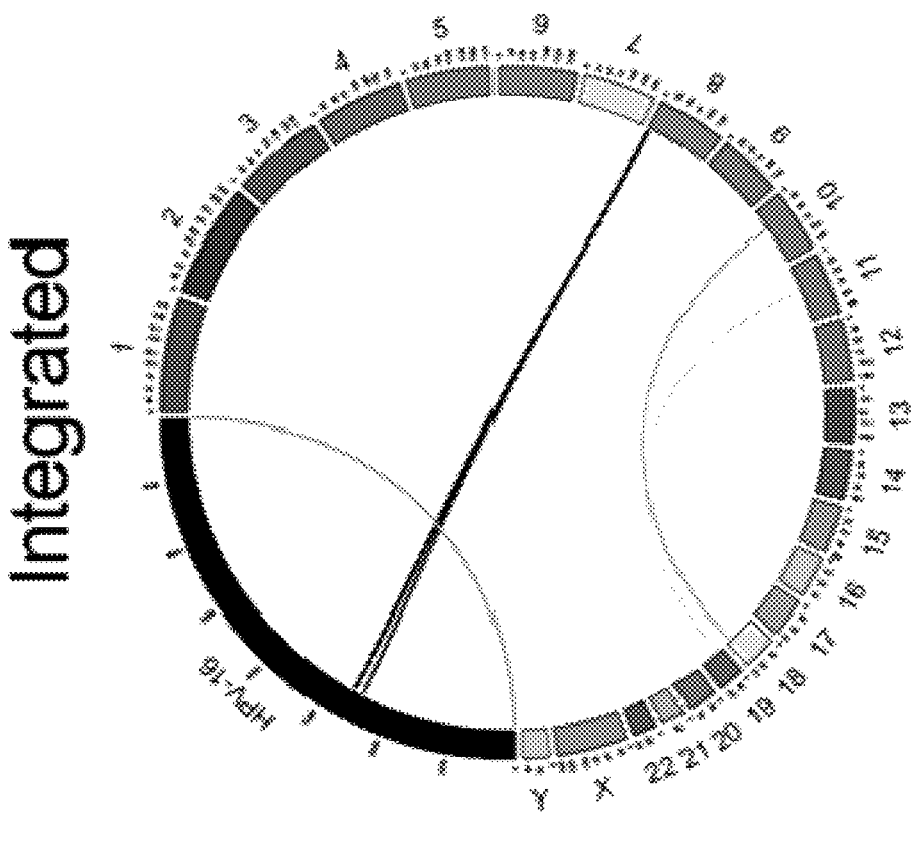
Figure 4D:
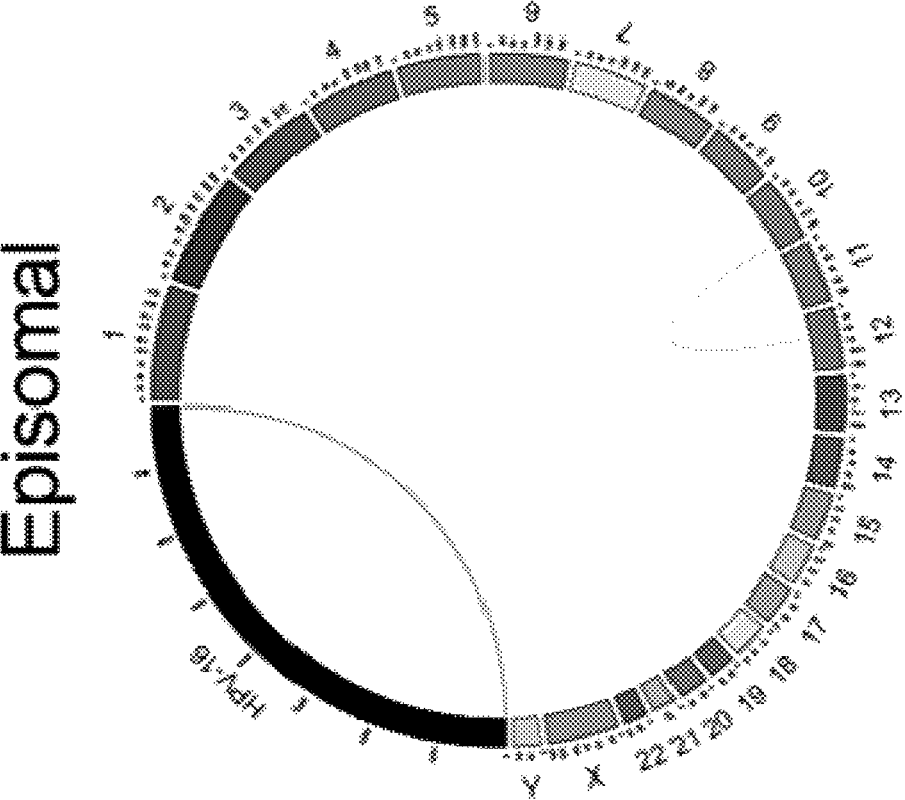
Figures 4E, 4F:
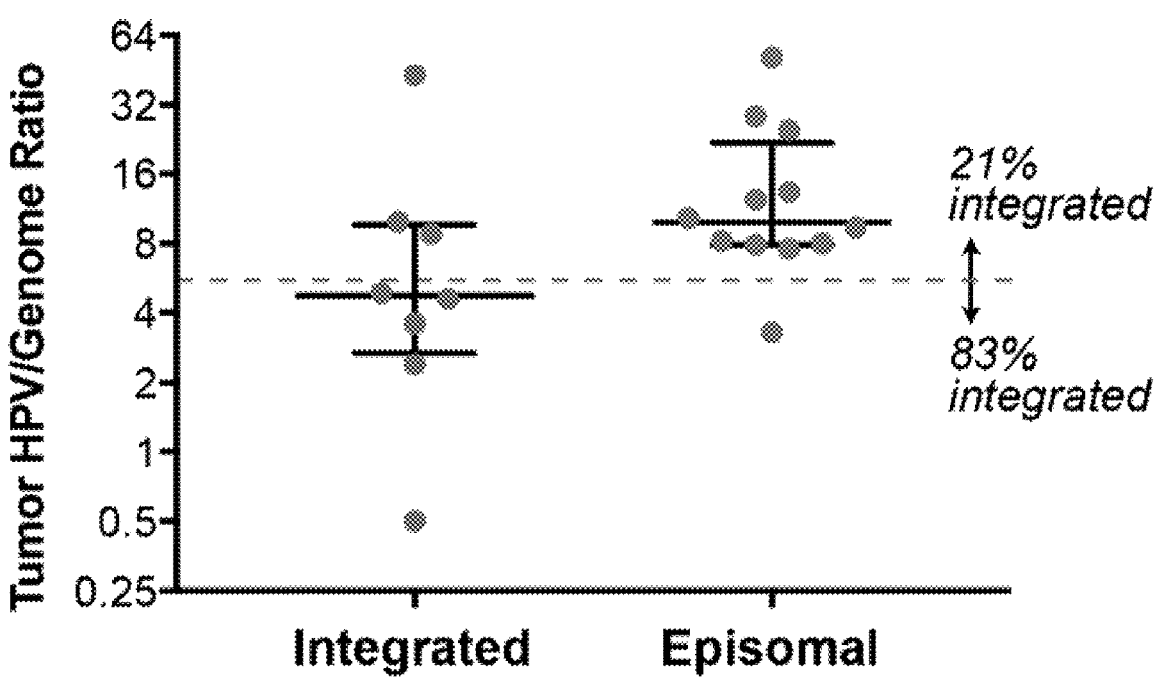

However, plasma ctHPV16 levels did not exhibit significant correlation with disease burden, as shown in FIG. 3C. Many different ways for a correlation between disease burden and peak HPV16 DNA values were looked into, one could not be found. However, by analyzing a 25 patient subset in whom tumor sequencing and plasma HPV16 DNA had been matched, a modest but statistically significant correlation between plasma circulating tumor HPV16 and copy number of HPV16 in the tumor was identified, shown in FIG. 3D. Thus, the number of HPV16 copies in plasma for a particular patient may reflect HPV copy number in their tumor, and have prognostic implications beyond disease stage and smoking history.

Attention was next turned to the HPV16 negative patients, and digital PCR assays were developed for the 4 most common alternative HPV strains. This analysis is shown in FIG. 12. Indeed among the non-heavy smokers, all of the HPV16 negative patients had detectable HPV 18/31/33 or 35 in their plasma. Among patients who were heavy smokers a significantly different pattern was observed. Slightly fewer patients were HPV16 positive. But among the HPV16 negative patients, only about ⅓rd had variant HPVs detectable, with the remainder negative for all 5 HPV strains. Perhaps even more concerning, 2 out of these four patients had a positive neck dissection post-treatment, and one patient also tested positive for a p53 mutation in the tumor. Among non-smokers no increased disease events with alternative HPV strains were observed, however, among smokers there were only 2 patients here but one of them developed regional recurrence soon after completing CRT. Thus, there seems to be an interactive effect of HPV16 negativity and smoking status.

Variable clearance kinetics among patients who were high expressers of HPV16 was also observed. As shown in FIG. 13, some patients had exponential clearance of HPV16 DNA and others had a more complex kinetic pattern with delayed clearance from plasma. This was quantified by measuring how much plasma HPV DNA was present at week 4 relative to the peak HPV value. For the top patient, this value is 0%, and for the bottom it is 39%. The median value of 5% was used to stratify patients as having either rapid clearance or delayed clearance kinetics.

Putting this all together, plasma circulating tumor HPV16 based risk groups were defined. This is depicted in FIG. 14. The favorable risk patients had abundant HPV16 and rapid clearance kinetics. All other patients had unfavorable circulating tumor HPV16 profiles either due to delayed kinetics, low copy number, due to being positive for variant HPVs, or due to undetectable HPV. For both non-smokers and smokers approximately 30% of patients had a favorable circulating tumor HPV16 profile, and 70% were unfavorable. Again noted here is the 20% subset of smokers in whom the 5 most common HPV strains were not detected.

As shown in FIG. 4, patients with a favorable circulating tumor HPV16 profile did not have any regional disease events-regardless of smoking status. However, in cases of patients having an unfavorable circulating tumor HPV profile, smoking status had a major impact. Non-heavy smokers still did well, with 90% regional disease control. However, heavy smokers or the minority presenting with T4 disease had dismal regional disease control when they also had unfavorable plasma circulating tumor HPV16 profiles.

In summary, plasma ctHPV16 DNA reveals genetic heterogeneity among HPV-associated OPSCC patients 4/18 (22%) patients with >10 pack-years tobacco or T4 disease and p16+ OPSCC were negative for HPV-16/18/31/33/35. Approximately 30% of HPV-associated OPSCC have a favorable ctHPV16 Profile (i.e., ≥200 copies/mL and rapid clearance kinetics) unfavorable ctHPV16 profiles (i.e., low/undetectable or delayed clearance) are strongly associated with regional disease failure in heavy smokers. Assessment of ctHPV16 profiles can help guide treatment intensity in non-smokers and smokers being treated for HPV-associated OPSCC.

Example 6: Application to Cancer Surveillance in a Longitudinal Clinical Study of Patients that do not Exhibit any Clinical Evidence of Cancer Following Therapy A prospective study was conducted of 73 patients who previously were diagnosed with an HPV+ malignancy but were deemed to have "no evidence of disease" after curative intent therapy. The HPV blood test was applied to these patients during a routine follow-up. None of the patients who tested negative in the HPV blood test developed a new HPV+ cancer or recurrence of the prior HPV+ cancer. In contrast, 9 out of 13 patients who tested positive in the HPV blood test were diagnosed with an HPV+ cancer.

FIG. 7 depicts results of HPV blood tests. Negative samples can be clearly distinguished from positive samples. FIG. 8 shows a case summary for a patient who tested positive according to the HPV blood test, but who exhibited no abnormality or evidence of disease at a follow-up visit with the oncologist, and who had a recurrence of disease several months after the follow-up.

A summary of the clinical results is shown in FIG. 7. These results show the predictive effectiveness of the HPV blood test. Of the 73 patients in the study, 60 tested negative according to the HPV blood test, and of which none exhibited a recurrence of disease. In contrast, of the 13 patients that tested positive according to the HPV blood test, 9 had a recurrence of disease, while the remaining 4 are being monitored closely for recurrence.

Example 7: Modified Oligonucleotide Compositions and Methods for Detection of Tumor-Derived HPV16

Provided in Table 14 below are primers and probes for detection of tumor-derived HPV16, where the "+" signifies a locked nucleic acid. Tumor derived HPV16 DNA can be detected and distinguished from non-tumor sources using any three primer/probe sets from Table 14 within a single multiplex digital PCR reaction, where the central probe has a detection color distinct from both of the other (boundary) probes. The two boundary probes may or may not have the same color. The DNA of the primer/probe sets is modified to include quenchers, dye moieties and locked nucleic acids. In this example, droplets that are positive for the central probe's detection label and negative for the boundary/distal probes detection label contain tumor derived viral DNA.

Figure 9:
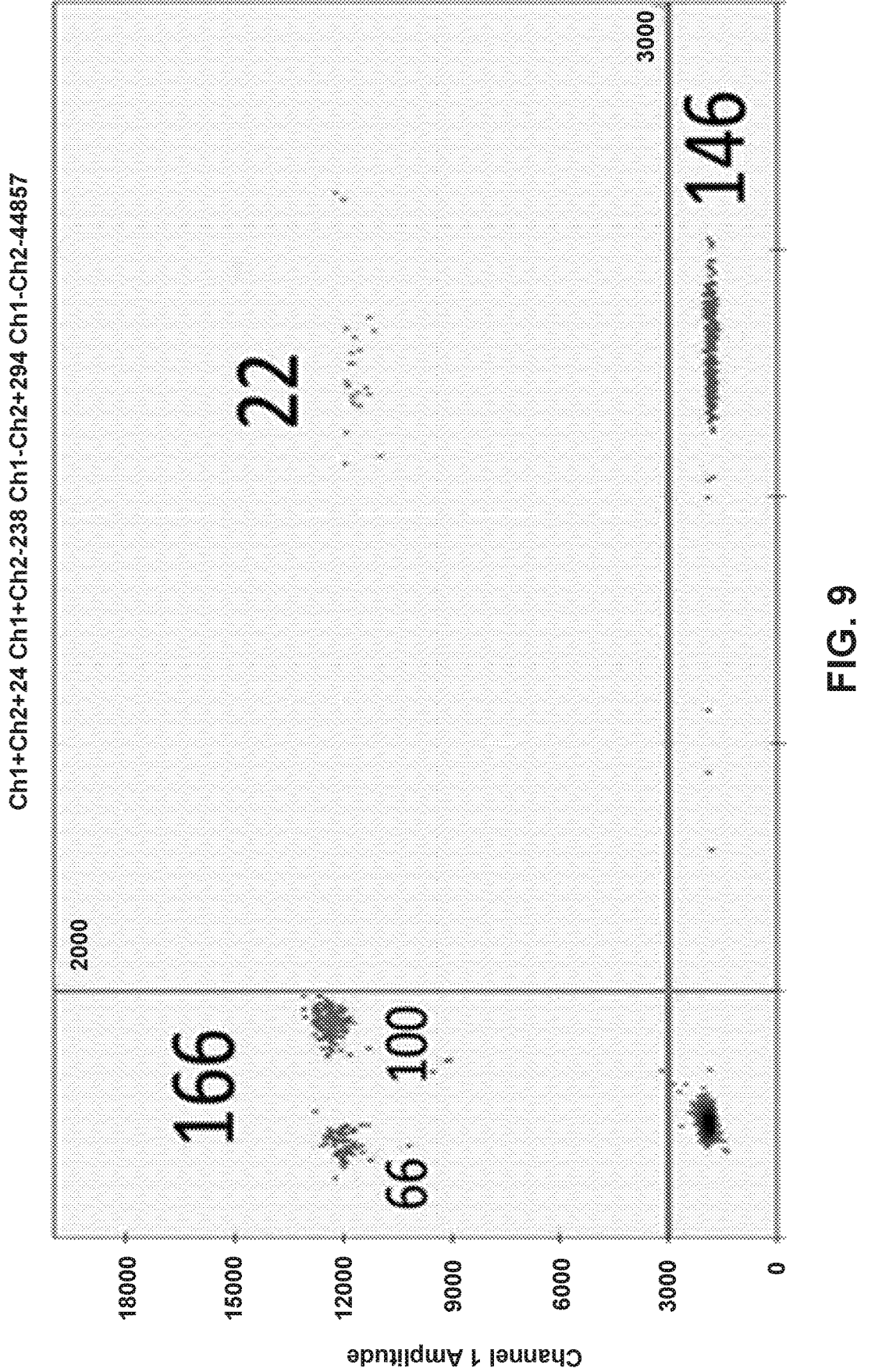
FIG. 9: Representative embodiment of method to detect tumor-derived HPV viral DNA assay using the triad primer/probe sets presented in Tables 14, 15, 16, 17, 18, 19, and 20. Shown are the digital PCR fluorescence detection plots for a multiplexed digital PCR reaction to detect tumor-derived HPV16 DNA in a patient blood sample that includes modified primer probe sets 3, 5 and 7 from Table 14, where detection probe 5 is conjugated to HEX and detection probes 3 and 7 are conjugated to FAM.

FIG. 9 depicts the results of a multiplexed digital PCR reaction to detect tumor-derived HPV16 DNA in a patient blood sample that includes modified primer probe sets 3, 5 and 7 from Table 14, where detection probe 5 is conjugated to HEX and detection probes 3 and 7 are conjugated to FAM.

As another example, modified primer probe sets 4, 7, and 10 from Table 14 could be used for the multiplexed digital PCR reaction to detect tumor-derived HPV16 DNA, where detection probe 7 is conjugated to FAM and detection probes 4 and 10 are conjugated to HEX. Alternatively, detection 7 could be conjugated to FAM, probe 4 conjugated to HEX, and probe 10 conjugated to a different detection moiety.

In some embodiments, the primer/probe sets may be selected so that no two sets are consecutive in Table 14. For illustration, examples of triads in this embodiment with no consecutive primer probe sets include $\{1, 3, 5\}, \{1, 3, 8\}, \{4, 6, 9\}, \ldots \{14, 16, 18\}$. Examples of triads with a consecutive primer probe set include $\{1, 2, 5\}$ and $\{10, 12, 13\}$.

For the purposes of this application, digital PCR refers to any method that will be understood to those versed in the art where PCR reactions are partitioned into many sub-reactions for analysis. The partition could be droplets or microwells or any other partition used for digital PCR.

It is to be understood that HEX and FAM are used solely for clarity and illustrative purposes in all the examples.

TABLE 14

| | | | | Primers and Probes for HPV16 | |
|---|---|---|---|---|---|
| Set | Amplicon (size) (Assay) | Detail | Named as | Sequence | $T_M{}^1$ |
| 1 | 1A (70 bp) | Forward primer | 1A_Primer1 | 5'TGC ACC AAA AGA GA+A CT3' (SEQ ID NO: 23) | 60.4 |
| | | Reverse primer | 1A_Primer2 | 5'GTG CAT AAC TGT GGT +AAC T3' (SEQ ID NO: 24) | 60.5 |
| | | TaqMan ® probe | 1A_Probe | 5'/Dye/CT+G +TG+G GTC +CT+GA/ Quencher/3' (SEQ ID NO: 25) | 68.2 |
| 2 | 2A (78 bp) (E6) | Forward primer | 2A_Primer1 | 5'AGA GOT GCA AAC AAC TAT ACA3' (SEQ ID NO: 26) | 62 |
| | | Reverse primer | 2A_Primer2 | 5'TAT ACC TCA CGT CGC AGT3' (SEQ ID NO: 27) | 62.2 |
| | | TaqMan ® probe | 2A_Probe | 5'/Dye/AGA ATG TGT /Quencher-2/GTA CTG CAA GCA ACA GTT/ Quencher-1/3' (SEQ ID NO: 28) | 67.5 |
| 3 | 3A (75 bp) | Forward primer | 3A_Primer1 | 5' CGT GAG GTA TAT GAC TTT GCTT3' (SEQ ID NO: 29) | 62.4 |

TABLE 14-continued

| | Amplicon (size) | | | | |
|---|---|---|---|---|---|
| Set | (Assay) | Detail | Named as | Sequence | $T_M{}^1$ |
| | | Reverse primer | 3A_Primer2 | 5' TCA CAT ACA GCA TAT GGA TTCC 3' (SEQ ID NO: 30) | 62.1 |
| | | TaqMan® probe | 3A_Probe | 5'/Dye/CG+G +GAT +TTA +T+G+CA/ Quencher/3' (SEQ ID NO: 31) | 69.4 |
| 4 | 4A (75 bp) | Forward primer | 4A_Primer1 | 5'GTT TTA TTC TAA AAT TAG TGA+G+TA T3' (SEQ ID NO: 32) | 60.2 |
| | | Reverse primer | 4A_Primer2 | 5'TTG TAT TGC TGT TCT A+AT GTT3' (SEQ ID NO: 33) | 59.9 |
| | | TaqMan® probe | 4A_Probe | 5'/Dye/AGT T+T+G +TA+T+G+GA/ Quencher/3' (SEQ ID NO: 34) | 67.1 |
| 5 | 5A (75 bp) | Forward primer | 5A_Primer1 | 5' CAA ACC GTT GTG TGA TTT GT 3' (SEQ ID NO: 35) | 61.9 |
| | | Reverse primer | 5A_Primer2 | 5' GAT GTC TTT GCT TTT CTT CAGG 3' (SEQ ID NO: 36) | 62 |
| | | TaqMan® probe | 5A_Probe | 5'/Dye/AAG C+C+A +CTG+T+GT/ Quencher/3' (SEQ ID NO: 37) | 68.1 |
| 6 | 6A (75 bp) | Forward primer | 6A_Primer1 | 5'TCT GGA CAA AAA GCA A+AG3' (SEQ ID NO: 38) | 60.6 |
| | | Reverse primer | 6A_Primer2 | 5'GA+T GAT CTG CAA CAA GAC3' (SEQ ID NO: 39) | 60.3 |
| | | TaqMan® probe | 6A_Probe | 5'/Dye/TCC AC+C G+A+C CCCT/ Quencher/3' (SEQ ID NO: 40) | 68 |
| 7 | 7A (76 bp) | Forward primer | 7A_Primer1 | 5' TGC ATG AAT ATA TGT TAG ATT TGC A 3' (SEQ ID NO: 41) | 61.9 |
| | | Reverse primer | 7A_Primer2 | 5' TCC TCT GAG CTG TCA TTT AATT 3' (SEQ ID NO: 42) | 61.9 |
| | | TaqMan® probe | 7A_Probe | 5'/Dye/A+C+A A+C+T +GAT CT+CT/ Quencher/3' (SEQ ID NO: 43) | 68.2 |
| 8 | 8A (74bp) | Forward primer | 8A_Primer1 | 5'TGA +AAT AGA TGG TCC AGC3' (SEQ ID NO: 44) | 60 |
| | | Reverse primer | 8A_Primer2 | 5'TGC AAC AAA AGG TTA CA+A TA3' (SEQ ID NO: 45) | 60 |
| | | TaqMan® probe | 8A_Probe | 5'/Dye/CAG +A+GC C+C+A T+T+AC/ Quencher/3' (SEQ ID NO: 46) | 68.1 |
| 9 | 9A (73 bp) (E7) | Forward primer | 9A_Primer1 | 5'TGA CTC TAC GCT TCG GTT G3' (SEQ ID NO: 47) | 63.6 |
| | | Reverse primer | 9A_Primer2 | 5'GCC CAT TAA CAG GTC TTC C3' (SEQ ID NO: 48) | 62.3 |
| | | TaqMan® probe | 9A_Probe_v1 | 5'/Dye/TACAAAGCA/Quencher-2/CAC ACG TAG ACA TTC GTA CTT/ Quencher-1/3' (SEQ ID NO: 49) | 68 |

TABLE 14-continued

| | Primers and Probes for HPV16 | | | | |
|---|---|---|---|---|---|
| Set | Amplicon (size) (Assay) | Detail | Named as | Sequence | $T_M{}^1$ |
| | | | 9A_Probe_v2 | 5'/Dye/CGT ACA AAG/Quencher-2/CAC ACA CGT AGA CAT TCG TAC/Quencher-1/3' (SEQ ID NO: 50) | 68.3 |
| | | | 9A_Probe_v3 | 5'/Dye/CA+CA+C+G+TA+G+ACAT/Quencher/3' (SEQ ID NO: 51) | 67.7 |
| 10 | 1B (79 bp) | Forward primer | 1 B_Primer1 | 5'ACT GCA ATG T+TT CAG G+A3' (SEQ ID NO: 52) | 60.2 |
| | | Reverse primer | 1 B_Primer2 | 5'CAT +GTA +TAG +TTG TTT +GC3' (SEQ ID NO: 53) | 60.1 |
| | | TaqMan ® probe | 1 B_Probe | 5'/Dye/CGA CCC AGA/Quencher-2/AAG TTA CCA CAG TTA TGC A/Quencher-1/3' (SEQ ID NO: 54) | 68.3 |
| 11 | 2B (75 bp) | Forward primer | 2B_Primer1 | 5'TTA GAA TGT GTG TAC TGC +AA3' (SEQ ID NO: 55) | 60.2 |
| | | Reverse primer | 2B_Primer2 | 5'CAT AAA TCC +CGA AAA GCA3' (SEQ ID NO: 56) | 60.2 |
| | | TaqMan ® probe | 2B_probe | 5'/Dye/GCA ACA GTT/Quencher-2/ACT GCG ACG TGA GGTAT/Quencher-1/3' (SEQ ID NO: 57) | 68.3 |
| 12 | 3B (75 bp) | Forward primer | 3B_Primer1 | 5'CAT A+GT ATA T+AG AG+A TGGGA3' (SEQ ID NO: 58) | 60.1 |
| | | Reverse primer | 3B_Primer2 | 5'TC+T ATA C+TC A+CT AAT TT+TAG3' (SEQ ID NO: 59) | 60.3 |
| | | TaqMan ® probe | 3B_Probe | 5'/Dye/A+T+C A+C+A TA+C+AGC/Quencher/3' (SEQ ID NO: 60) | 66.6 |
| 13 | 4B (73 bp) | Forward primer | 4B_Primer1 | 5'CAT TAT TGT TAT A+G+T T+T+TGTA3' (SEQ ID NO: 61) | 59.9 |
| | | Reverse primer | 4B_Primer2 | 5'TAA TTA ACA AAT CAC A+CAACG3' (SEQ ID NO: 62) | 59.9 |
| | | TaqMan ® probe | 4B_Probe | 5'/Dye/TA+T +G+G+A A+CA A+CAT/Quencher/3' (SEQ ID NO: 63) | 67.6 |
| 14 | 5B (70 bp) | Forward primer | 5B_Primer1 | 5'TG+T ATT AA+C T+GT C+AA AAG3' (SEQ ID NO: 64) | 60.2 |
| | | Reverse primer | 5B_Primer2 | 5'GGA +ATC TTT GCT TTT +TGT3' (SEQ ID NO: 65) | 60.1 |
| | | TaqMan ® probe | 5B_Probe | 5'/Dye/TG+T +GT+C +CT+G AAGA/Quencher/3' (SEQ ID NO: 66) | 68 |
| 15 | 6B (80 bp) | Forward primer | 6B_Primer1 | 5'ATA ATA TAA GGG GTC G+GT G3' (SEQ ID NO: 67) | 60.1 |
| | | Reverse primer | 6B_Primer2 | 5'AGC TGG GTT TCT CTA CG3' (SEQ ID NO: 68) | 60.4 |
| | | TaqMan ® probe | 6B_Probe_v1 | 5'/Dye/CGG TCG ATG / Quencher-2/TAT GTC TTG TTG CAG ATC ATC/ | 68.4 |

TABLE 14-continued

| Primers and Probes for HPV16 | | | | | |
| --- | --- | --- | --- | --- | --- |
| Amplicon (size) Set (Assay) | Detail | Named as | Sequence | | $T_M{}^1$ |
| | | | Quencher-1/3' (SEQ ID NO: 69) | | |
| | | 6B_Probe_v2 | 5'/Dye/CCG GTC GAT / Quencher-2/GTA TGT CTT GTT GCA GAT/ Quencher-1/3' (SEQ ID NO: 70) | | 68.3 |
| 16 7B (72 bp) | Forward primer | 7B_Primer1 | 5'TGC ATG GAG ATA CAC CT3' (SEQ ID NO: 71) | | 59.7 |
| | Reverse primer | 7B_Primer2 | 5'ACA GTA G+AG ATC AGT TGT3' (SEQ ID NO: 72) | | 59.9 |
| | TaqMan ® probe | 7B_Probe | 5'/Dye/CC+A G+A+G A+C+AA+CT/ Quencher/3' (SEQ ID NO: 73) | | 68.4 |
| 17 8B (92 bp) | Forward primer | 8B_Primer1 | 5'TAT GAG CAA TTA A+A+T G+ACA3' (SEQ ID NO: 74) | | 60 |
| | Reverse primer | 8B_Primer2 | 5'ATT GT+A ATG GGC TCT GTC3' (SEQ ID NO: 75) | | 59.9 |
| | TaqMan ® probe | 8B_Probe | 5'/Dye/ATT T+C+A TC+C +T+C+CT/ Quencher/3' (SEQ ID NO: 76) | | 68.1 |
| 18 9B (92 bp) | Forward primer | 9B_Primer1 | 5'TAC +AAA GCA CAC ACG TAG3' (SEQ ID NO: 77) | | 60 |
| | Reverse primer | 9B_Primer2 | 5'TT+A TGG TTT CTG AGA ACA GAT3' (SEQ ID NO: 78) | | 60.4 |
| | TaqMan ® probe | 9B_Probe | 5'/Dye/TGG AAG ACC /Quencher-2/TGT TAA TGG GCA CACT/ Quencher-1/3' (SEQ ID NO: 79) | | 68.1 |

[1]"Dye" stands for a fluorescent reporter dye.
Any reporter dyes such as FAM ™, HEX ™, VIC ®, Cy5 ™, and Cy5.5 ™ that is compatible with the detection channels for the instrument can be used.
A quencher compatible with the respective dye was used at 3' end of the probe (Quencher-1).
A second quencher (Quencher-2) such as ZEN was sometimes placed internally between 9th and 10th nucleotide base from the reporter dye to enhance the overall dye quenching.
Note that quenchers are linked to both the preceding and following nucleic acid.
[2]These estimates of melting temperature (TM) were calculated using IDT'S oligo analyzer tools with following settings:
(a) For primers:
Target type = DNA,
Oligo concentration = 0.9 µM,
Nat concentration = 50 mM,
$Mg^{++}$ concentration = 3 mM, and
dNTPs concentration = 0.8 mM.
(b) for Probe:
Target type = DNA,
Oligo concentration = 0.25 µM,
Nat concentration = 50 mM,
$Mg^{++}$ concentration = 3 mM, and
dNTPs concentration = 0.8 mM.
[3]+ before a nucleic acid = Locked nucleic acid.

Example 8: Modified Oligonucleotide Compositions and Methods for Detection of Tumor-Derived HPV18

Provided in Table 15 below are primers and probes for detection of tumor-derived HPV18, where the "+" signifies a locked nucleic acid. Tumor derived HPV18 DNA can be detected and distinguished from non-tumor sources using any three primer/probe sets from Table 15 within a single multiplex digital PCR reaction, where the central probe has a detection color distinct from both of the other (boundary) probes. The two boundary probes may or may not have the same color. The DNA of the primer/probe sets is modified to include quenchers, dye moieties, and locked nucleic acids. In this example, droplets that are positive for the central probe's detection label and negative for the boundary/distal probes detection label contain tumor derived viral DNA.

For example, modified primer probe sets 4, 7, and 10 from Table 15 could be used for the multiplexed digital PCR reaction to detect tumor-derived HPV18 DNA, where detection probe 7 is conjugated to FAM and detection probes 4 and 10 are conjugated to HEX. Alternatively, detection 7 could be conjugated to FAM, probe 4 conjugated to HEX, and probe 10 conjugated to a different detection moiety.

In some embodiments, the primer/probe sets may be selected so that no two sets are consecutive in Table 15. For illustration, examples of triads in this embodiment with no consecutive primer probe sets include {1, 3, 5}, {1, 3, 8}, {4, 6, 9}, . . . {14, 16, 18}. Examples of triads with a consecutive primer probe set include {1, 2, 5} and {10, 12, 13}.

For the purposes of this application, digital PCR refers to any method that will be understood to those versed in the art where PCR reactions are partitioned into many sub-reactions for analysis. The partition could be droplets or microwells or any other partition used for digital PCR.

It is to be understood that HEX and FAM are used solely for clarity and illustrative purposes in all the examples.

TABLE 15

| | | | | | |
|---|---|---|---|---|---|
| | | | Primers and probes for HPV18 | | |
| Set | Amplicon (size) (Assay) | Detail | Named as | Sequence | $T_M^1$ |
| 1 | 1C (70 bp) (E6) | Forward primer | 1C_Primer1 | 5'CGC TTT GAG GAT CCA AC3' (SEQ ID NO: 80) | 60 |
| | | Reverse primer | 1 C_Primer2 | 5'GCA GTG AAG TGT TCA GTT3' (SEQ ID NO: 81) | 60 |
| | | TaqMan ® probe | 1 C_Probe | 5'/Dye/ACC CTA CAA/Quencher-2/GCT ACC TGA TCT GTG C/Quencher-1/3' (SEQ ID NO: 82) | 67.6 |
| 2 | 2C (76 bp) (E6) | Forward primer | 2C_Primer1 | 5'AAG ACA +TAG AAA TAA CCT +GT3' (SEQ ID NO: 83) | 60.2 |
| | | Reverse primer | 2C_Primer2 | 5'TTA A+A+T +G+CA AAT TCA AAT3' (SEQ ID NO: 84) | 60.3 |
| | | TaqMan ® probe | 2C_Probe | 5'/Dye/TGC AAG ACA /Quencher-2/GTA TTG GAA CTT ACA GAG GT/Quencher-1/3' (SEQ ID NO: 85) | 67.7 |
| 3 | 3C (80 bp) (E6) | Forward primer | 3C_Primer1 | 5'TTA T+TT GTG GTG TAT A+GA GA3' (SEQ ID NO: 86) | 59.8 |
| | | Reverse primer | 3C_Primer2 | 5'AAT T+CT +CTA ATT +CTA GAA TAA3' (SEQ ID NO: 87) | 59.8 |
| | | TaqMan probe | 3C_Probe | 5'/Dye/CA+T G+C+G +G+TA +TAC T/Quencher/3' (SEQ ID NO: 88) | 68.2 |
| 4 | 4C (72 bp) (E6) | Forward primer | 4C_Primer1 | 5'AAG AC+A TTA +TTC AGA C+TC T3' (SEQ ID NO: 89) | 60.2 |
| | | Reverse primer | 4C_Primer2 | 5'AAT AAA TTG +TAT AAC +C+CA3' (SEQ ID NO: 90) | 60.4 |
| | | TaqMan ® probe | 4C_Probe | 5'/Dye/TG+G +AGA +C+A+C +ATT/Quencher/3' (SEQ ID NO: 91) | 67.6 |
| 5 | 5C (71 bp) (E6) | Forward primer | 5C_Primer1 | 5'AGAAACCGTTGAATCCAG3' (SEQ ID NO: 92) | 59.5 |
| | | Reverse primer | 5C_Primer2 | 5'ATT TCA CAA CAT AGC TGG G3' (SEQ ID NO: 93) | 60.1 |
| | | TaqMan ® probe | 5C_Probe | 5'/Dye/AG+A CA+C +C+TT AA+T +GA/Quencher/3' (SEQ ID NO: 94) | 68.1 |
| 6 | 6C (80 bp) (E6) | Forward primer | 6C_Primer1 | 5'CCA GTG CCA TTC GTG C3' (SEQ ID NO: 95) | 60.8 |
| | | Reverse primer | 6C_Primer2 | 5'TTA TA+C TTG +TGT TTC TCT G3' (SEQ ID NO: 96) | 60.1 |
| | | TaqMan ® probe | 6C_Probe | 5'/Dye/CAC GAC AGG /Quencher-2/AAC GAC TCC AAC GAC/Quencher-1/3' (SEQ ID NO: 97) | 68.3 |
| 7 | 7C (72 bp) (E7) | Forward primer | 7C_Primer1 | 5'ATG GAC CTA AGG CAA CA3' (SEQ ID NO: 98) | 60.3 |

TABLE 15-continued

Primers and probes for HPV18

| Set | Amplicon (size) (Assay) | Detail | Named as | Sequence | $T_M{}^1$ |
|---|---|---|---|---|---|
| | | Reverse primer | 7C_Primer2 | 5'TG+A CAT AGA AGG TCA ACC3' (SEQ ID NO: 99) | 60.2 |
| | | TaqMan ® probe | 7C_Probe | 5'/Dye/TT+T A+G+A +G+CC +CC/Quencher/3' (SEQ ID NO: 100) | 68.2 |
| 8 | 8C (75 bp) (E7) | Forward primer | 8C_Primer1 | 5'CGA GCA A+TT AAG CGA CTC3' (SEQ ID NO: 101) | 60.2 |
| | | Reverse primer | 8C_Primer2 | 5'CGG GCT GGT AAA TGT TGA3' (SEQ ID NO: 102) | 60 |
| | | TaqMan ® probe | 8C_Probe | 5'/Dye/T+C+G +TTT T+CT T+C+C T/Quencher/3' (SEQ ID NO: 103) | 68.1 |
| 9 | 9C (75 bp) (E7) | Forward primer | 9C_Primer1 | 5'ACA ACG TCA CAC AAT GTT3' (SEQ ID NO: 104) | 60.1 |
| | | Reverse primer | 9C_Primer2 | 5'TCT GCT GAG CTT TCT ACT3' (SEQ ID NO: 105) | 60 |
| | | TaqMan ® probe | 9C_Probe | 5'/Dye/TGT ATG TGT/Quencher-2/TGT AAG TGT GAA GCC AGA AT/Quencher-1/3' (SEQ ID NO: 106) | 66.9 |
| 10 | 10C (74 bp) (E7) | Forward primer | 10C_Primer1 | 5'ACC TTC GAG CAT TCC A3' (SEQ ID NO: 107) | 60.2 |
| | | Reverse primer | 10C_Primer2 | 5'TTACTGCTGGGATGCA3' (SEQ ID NO: 108) | 60.2 |
| | | TaqMan ® probe | 10C_Probe | 5'/Dye/CTG AA+C +AC+C C+T+G T/Quencher/3' (SEQ ID NO: 109) | 68.2 |
| 11 | 1D (83 bp) (E6) | Forward primer | 1 D_Primer1 | 5'CCC TAC AAG CTA CCT GAT3' (SEQ ID NO: 110) | 60 |
| | | Reverse primer | 1 D_Primer2 | 5'CAA TAT A+CA +CAG +GT+T ATT T3' (SEQ ID NO: 111) | 60.1 |
| | | TaqMan ® probe | 1 D_Probe | 5'/Dye/CA+C +G+GA A+C+T GAA C/Quencher/3' (SEQ ID NO: 112) | 68.1 |
| 12 | 2D (92 bp) (E6) | Forward primer | 2D_Primer1 | 5'TAT TT+G +AAT TT+G +CAT +TTA3' (SEQ ID NO: 113) | 59.9 |
| | | Reverse primer | 2D_Primer2 | 5'AAT +CTA TA+C +ATT TAT +GGC3' (SEQ ID NO: 114) | 59.9 |
| | | TaqMan ® probe | 2D_Probe | 5'/Dye/AG+A C+AG +TA+T AC+C+GC/ Quencher/3' (SEQ ID NO: 115) | 67.9 |
| 13 | 3D (74 bp) (E6) | Forward primer | 3D_Primer1 | 5'CTA G+AA TTA +G+A+G AAT T+AA GA3' (SEQ ID NO: 116) | 60.1 |
| | | Reverse primer | 3D_Primer2 | 5'AGT GTT AGT TAG TTT +TTC AAT3' (SEQ ID NO: 117) | 60.1 |
| | | TaqMan ® probe | 3D_Probe | 5'/Dye/TC+A +G+A+C T+CT G+TG T/Quencher/3' (SEQ ID NO: 118) | 68.4 |
| 14 | 4D (75 bp) (E6) | Forward primer | 4D_Primer1 | 5'ATT A+AT AAG GTG CC+T GC3' (SEQ ID NO: 119) | 60.2 |
| | | Reverse primer | 4D_Primer2 | 5'TCG III I I c AIT A+AG GTG T3' (SEQ ID NO: 120) | 60 |
| | | TaqMan ® probe | 4D_Probe | 5'/Dye/TGA AT+C +C+AG C+A+G A/Quencher/3' (SEQ ID NO: 121) | 67.8 |
| 15 | 5D (98 bp) (E6) | Forward primer | 5D_Primer1 | 5'ATT TCA CAA CAT AGC TGG G3' (SEQ ID NO: 122) | 60.1 |

TABLE 15-continued

Primers and probes for HPV18

| Set | Amplicon (size) (Assay) | Detail | Named as | Sequence | $T_M^1$ |
|---|---|---|---|---|---|
| | | Reverse primer | 5D_Primer2 | 5'GTT TCT CTG CGT CGT TG3' (SEQ ID NO: 123) | 60.4 |
| | | TaqMan ® probe | 5D_Probe | 5'/Dye/AG+T G+C+C +A+TT C+GT G/Quencher/3' (SEQ ID NO: 124) | 68.3 |
| 16 | 6D (90 bp) (E7) | Forward primer | 6D_Primer1 | 5'ATT +GTA TTG CAT TTA GAG CC3' (SEQ ID NO: 125) | 59.8 |
| | | Reverse primer | 6D_Primer2 | 5'TTC ATC GTT TTC TTC +CTC3' (SEQ ID NO: 126) | 59.9 |
| | | TaqMan ® probe | 6D_Probe | 5'/Dye/CTA T+G+T +CA+C +G+AG C/Quencher/3' (SEQ ID NO: 127) | 68.2 |
| 17 | 7D (82 bp) (E7) | Forward primer | 7D_Primer1 | 5'ATA GAT G+GA GTT A+AT CAT CA3' (SEQ ID NO: 128) | 59.7 |
| | | Reverse primer | 7D_Primer2 | 5'AC+T TAC AAC ACA +TAC ACA3' (SEQ ID NO: 129) | 60 |
| | | TaqMan ® probe | 7D_Probe | 5'/Dye/CCG AAC CAC/Quencher-2/AAC GTC ACA CAA TGT T/Quencher-1/3' (SEQ ID NO: 130) | 67.8 |
| 18 | 8D (83 bp) (E7) | Forward primer | 8D_Primer1 | 5'TGA AGO CAG AAT TGA GOT AG3' (SEQ ID NO: 131) | 61.9 |
| | | Reverse primer | 8D_Primer2 | 5'AGG ACA GGG TGT TCA GAA3' (SEQ ID NO: 132) | 62.6 |
| | | TaqMan ® probe | 8D_Probe | 5'/Dye/CA+GA+C+GAC+CTTCG/Quencher/3' (SEQ ID NO: 133) | 65.9 |

[1]"Dye" stands for a fluorescent reporter dye.
Any reporter dyes such as FAM ™, HEX ™, VIC ®, Cy5 ™, and Cy5.5 ™ that is compatible with the detection channels for the instrument can be used.
A quencher compatible with the respective dye was used at 3' end of the probe (Quencher-1).
A second quencher (Quencher-2) such as ZEN was sometimes placed internally between $9^{th}$ and $10^{th}$ nucleotide base from the reporter dye to enhance the overall dye quenching.
[2]These estimates of melting temperature(TM) were calculated using IDT'S oligo analyzer tools with following settings:
(a) For primers:
Target type = DNA,
Oligo concentration = 0.9 µM,
Nat concentration = 50 mM,
$Mg^{++}$ concentration = 3 mM, and
dNTPs concentration = 0.8 mM.
(b) for Probe:
Target type = DNA,
Oligo concentration = 0.25 µM,
Nat concentration = 50 mM,
$Mg^{++}$ concentration = 3 mM, and
dNTPs concentration = 0.8 mM.
[3]+ = Locked nucleic acid Example 9: Modified Oligonucleotide Compositions and Methods for Detection of Tumor-Derived HPV31

Provided in Table 16 below are primers and probes for detection of tumor-derived HPV31, where the "+" signifies a locked nucleic acid. Tumor derived HPV31 DNA can be detected and distinguished from non-tumor sources using any three primer/probe sets from Table 16 within a single multiplex digital PCR reaction, where the central probe has a detection color distinct from both of the other (boundary) probes. The two boundary probes may or may not have the same color. The DNA of the primer/probe sets is modified to include quenchers, dye moieties and locked nucleic acids. In this example, droplets that are positive for the central probe's detection label and negative for the boundary/distal probes detection label contain tumor derived viral DNA.

For example, modified primer probe sets 4, 7, and 10 from Table 16 could be used for the multiplexed digital PCR reaction to detect tumor-derived HPV31 DNA, where detection probe 7 is conjugated to FAM and detection probes 4 and 10 are conjugated to HEX. Alternatively, detection 7 could be conjugated to FAM, probe 4 conjugated to HEX, and probe 10 conjugated to a different detection moiety.

In some embodiments, the primer/probe sets may be selected so that no two sets are consecutive in Table 16. For illustration, examples of triads in this embodiment with no consecutive primer probe sets include {1, 3, 5}, {1, 3, 8}, {4, 6, 9}, . . . {13, 15, 17}. Examples of triads with a consecutive primer probe set include {1, 2, 5} and {10, 12, 13}.

For the purposes of this application, digital PR refers to any method that will be understood to those versed in the art where PCR reactions are partitioned into many sub-reactions for analysis. The partition could be droplets or microwells or any other partition used for digital PCR.

It is to be understood that HEX and FAM are used solely for clarity and illustrative purposes in all the examples.

TABLE 16

| | | | | | |
|---|---|---|---|---|---|
| Set | Amplicon (size) (Assay) | Detail | Named as | Sequence | $T_M^1$ |
| 1 | 1E (75 bp) (E6) | Forward primer | 1 E_Primer1 | 5'ATG TTC AAA AA+T CCT GCA3' (SEQ ID NO: 134) | 60 |
| | | Reverse primer | 1E_Primer2 | 5'TTC ATC GTA GGG TAT +TTC 03' (SEQ ID NO: 135) | 60.2 |
| | | TaqMan ® probe | 1 E_Probe | 5'/Dye/AAC +T+AA G+C+T C+G+G C/Quencher/3' (SEQ ID NO: 136) | 68.3 |
| 2 | 2E (75 bp) (E6) | Forward primer | 2E_Primer1 | 5'CT+A AGA TTG A+AT TGT GT+C T3' (SEQ ID NO: 137) | 59.9 |
| | | Reverse primer | 2E_Primer2 | 5'TAA ATC +TGT AAA TGC AA+A ATC TA 3' (SEQ ID NO: 138) | 59.9 |
| | | TaqMan ® probe | 2E_Probe | 5'/Dye/AC+A GA+A A+CA +G+AG +GT/Quencher/3' (SEQ ID NO: 139) | 68.1 |
| 3 | 3E (75 bp) (E6) | Forward primer | 3E_Primer1 | 5'ACA ATA +GTA TAT AGG GAC GAC3' (SEQ ID NO: 140) | 59.9 |
| | | Reverse primer | 3E_Primer2 | 5'TTC ACT +TAC TTT TGA +ATA +AAA T3' (SEQ ID NO: 141) | 59.8 |
| | | TaqMan ® probe | 3E_Probe | 5'/Dye/AC+G +G+AG TG+T +GTA C/Quencher/3' (SEQ ID NO: 142) | 68.1 |
| 4 | 4E (81 bp) (E6) | Forward primer | 4E_Primer1 | 5'TTT A+GA TG+G TAT AGA TAT AGT GT3' (SEQ ID NO: 143) | 60 |
| | | Reverse primer | 4E_Primer2 | 5'CC+T AAT TAA +C+AA ATC ACA TA3' (SEQ ID NO: 144) | 60 |
| | | TaqMan ® probe | 4E_Probe | 5'/Dye/A+T+G +G+AA +C+AA CAT T/Quencher/3' (SEQ ID NO: 145) | 67.7 |
| 5 | 5E (74 bp) (E6) | Forward primer | 5E_Primer1 | 5'TGT AT+A ACG TGT +CAA AGA C (SEQ ID NO: 146) | 60 |
| | | Reverse primer | 5E_Primer2 | 5'TTG TGG AAT C+GT T+TC TTT3' (SEQ ID NO: 147) | 59.9 |
| | | TaqMan ® probe | 5E_Probe | 5'/Dye/TGT +G+TC +C+AG A+A+G A/Quencher/3' (SEQ ID NO: 148) | 68.4 |
| 6 | 6E (70 bp) (E6) | Forward primer | 6E_Primer1 | CAT AGG AGG AAG GTG GAC (SEQ ID NO: 149) | 60.5 |
| | | Reverse primer | 6E_Primer2 | 5'TTA CAC TT+G GGT +TTC AG3' (SEQ ID NO: 150) | 60.2 |
| | | TaqMan ® probe | 6E_Probe | 5'/Dye/CGT TGC ATA /Quencher-2/GCA TGT TGG AGA AGA CC/Quencher-1/3' (SEQ ID NO: 151) | 67.4 |
| 7 | 7E (75 bp) (E7) | Forward primer | 7E_Primer1 | 5'CAA GA+C TAT GTG TTA +GAT T3' (SEQ ID NO: 152) | 59.9 |
| | | Reverse primer | 7E_Primer2 | 5'TCA TCT GAG CTG TC+G G+GT AAT T3' (SEQ ID NO: 153) | 60.1 |
| | | TaqMan ® probe | 7E_Probe | 5'/Dye/AAC TGA +C+C+T C+C+A C/Quencher/3' (SEQ ID NO: 154) | 68.3 |
| 8 | 8E (89 bp) (E7) | Forward primer | 8E_Primer1 | 5'AGG ATG TCA TA+G ACA GTC3' (SEQ ID NO: 155) | 59.8 |

TABLE 16-continued

| | | | | | |
|---|---|---|---|---|---|
| | | | Primers and probes for HPV31 | | |
| Set | Amplicon (size) (Assay) | Detail | Named as | Sequence | $T_M{}^1$ |
| | | Reverse primer | 8E_Primer2 | 5'TG+T AGA CTT ACA CTG ACA A3' (SEQ ID NO: 156) | 60.3 |
| | | TaqMan ® probe | 8E_Probe | 5'/Dye/CTG +G+AC A+AG +C+AG A/Quencher/3' (SEQ ID NO: 157) | 68 |
| 9 | 9E (79 bp) (E7) | Forward primer | 9E_Primer1 | 5'AGC ACA CAA GTA GAT ATT CGC3' (SEQ ID NO: 158) | 62.4 |
| | | Reverse primer | 9E_Primer2 | 5'TAG TAG AAC AGT TGG GGC A3' (SEQ ID NO: 159) | 62.6 |
| | | TaqMan ® probe | 9E_Probe | 5'/Dye/TAA+C+AG+CT+C+TTG+C/Quencher/3' (SEQ ID NO: 160) | 65.3 |
| 10 | 1F (82 bp) (E6) | Forward primer | 1F_Primer1 | 5'AAA TTG CAT G+AA CTA +AGC3' (SEQ ID NO: 161) | 60.2 |
| | | Reverse primer | 1 F_Primer2 | 5'TT+A ACT GAC CTT TGC AGT3' (SEQ ID NO: 162) | 59.8 |
| | | TaqMan ® probe | 1F_Probe | 5'/Dye/CGG CAT TGG /Quencher-2/AAA TAC CCT ACG ATG AAC TAA/Quencher-1/3' (SEQ ID NO: 163) | 68.1 |
| 11 | 2F (90 bp) (E6) | Forward primer | 2F_Primer1 | 5'CAG AA+A CAG AGG TAT TA+G AT3' (SEQ ID NO: 164) | 60.1 |
| | | Reverse primer | 2F_Primer2 | 5'TTA +AAC ATT TTG TAC A+CA CT3' (SEQ ID NO: 165) | 59.8 |
| | | TaqMan ® probe | 2F_Probe | 5'/Dye/AC+G +A+CA +C+AC CAC A/Quencher/3' (SEQ ID NO: 166) | 68.1 |
| 12 | 3F (81 bp) (E6) | Forward primer | 3F_Primer1 | 5'ATT T+TA TTC AA+A AGT A+AG TGA3' (SEQ ID NO: 167) | 59.8 |
| | | Reverse primer | 3F_Primer2 | 5'CCT +TTG TTT GTC +AAT T+TT TC3' (SEQ ID NO: 168) | 60.1 |
| | | TaqMan ® probe | 3F_Probe | 5'/Dye/TAG +T+G+T GTA +T+G+G A/Quencher/3' (SEQ ID NO: 169) | 68.7 |
| 13 | 4F (75 bp) (E6) | Forward primer | 4F_Primer1 | 5'TAT ATG TGA TTT GTT A+AT TA+G GT3' (SEQ ID NO: 170) | 60 |
| | | Reverse primer | 4F_Primer2 | 5'TCC AA+A TGT C+TT TGT TTT TC3' (SEQ ID NO: 171) | 60.1 |
| | | TaqMan ® probe | 4F_Probe | 5'/Dye/CC+G TT+G T+G+T +C+CA G/Quencher/3' (SEQ ID NO: 172) | 68.1 |
| 14 | 5F (80 bp) (E6) | Forward primer | 5F_Primer1 | 5'TAA AAA G+AA ACG ATT +CCA C3' (SEQ ID NO: 173) | 60.1 |
| | | Reverse primer | 5F_Primer2 | 5'TT+T CAG TAC GAG GTC TTC3' (SEQ ID NO: 174) | |
| | | TaqMan ® probe | 5F_Probe | 5'/Dye/AAG GTG GAC/Quencher-2/AGG ACG TTG CA/Quencher-1/3' (SEQ ID NO: 175) | 66.5 |
| 15 | 6F (74 bp) (E7) | Forward primer | 6F_Primer1 | 5'TGG AGA AAC ACC TAC GT3' (SEQ ID NO: 176) | 59.8 |
| | | Reverse primer | 6F_Primer2 | 5'TAA TTG CTC AT+A ACA GTG GA3' (SEQ ID NO: 177) | 60 |
| | | TaqMan ® probe | 6F_Probe | 5'/Dye/AA+C +C+T+G AGG CAA C/Quencher/3' (SEQ ID NO: 178) | 68.3 |
| 16 | 7F (74 bp) (E7) | Forward primer | 7F_Primer1 | 5'AGA TGA GGA GGA TGT C+AT3' (SEQ ID NO: 179) | 60.3 |

TABLE 16-continued

| Set | Amplicon (size) (Assay) | Detail | Named as | Sequence | $T_M{}^1$ |
|---|---|---|---|---|---|
| | | Reverse primer | 7F_Primer2 | 5'AG+G TAA +CGA TAT T+GT AAT T3' (SEQ ID NO: 180) | 59.8 |
| | | TaqMan ® probe | 7F_Probe | 5'/Dye/CA+A +G+C+A G+AA C+CG/Quencher/3' (SEQ ID NO: 181) | 67.9 |
| 17 | 8F (90 bp) (E7) | Forward primer | 8F_Primer1 | 5'TGT CAG T+GT AAG TC+T ACA3' (SEQ ID NO: 182) | 60.2 |
| | | Reverse primer | 8F_Primer2 | 5'TCC AAA TGA GCC C+AT TAA3' (SEQ ID NO: 183) | 59.9 |
| | | TaqMan ® probe | 8F_Probe | 5'/Dye/TGT +A+C+A +GA+G CA+C A/Quencher/3' (SEQ ID NO: 184) | 68.2 |

[1]"Dye" stands for a fluorescent reporter dye.
Any reporter dyes such as FAM ™, HEX ™, VIC ®, Cy5 ™, and Cy5.5 ™ that is compatible with the detection channels for the instrument can be used.
A quencher compatible with the respective dye was used at 3' end of the probe (Quencher-1).
A second quencher (Quencher-2) such as ZEN was sometimes placed internally between [9th] and [10th] nucleotide base from the reporter dye to enhance the overall dye quenching.
[2] These estimates of melting temperature(TM) were calculated using IDT'S oligo analyzer tools with following settings:
(a) For primers:
Target type = DNA,
Oligo concentration = 0.9 µM,
Nat concentration = 50 mM,
$Mg^{++}$ concentration = 3 mM, and
dNTPs concentration = 0.8 mM.
(b) for Probe:
Target type = DNA,
Oligo concentration = 0.25 µM,
Nat concentration = 50 mM,
$Mg^{++}$ concentration = 3 mM, and
dNTPs concentration = 0.8 mM.
[3]+ = Locked nucleic acid

Example 10: Modified Oligonucleotide Compositions and Methods for Detection of Tumor-Derived HPV33

Provided in Table 17 below are primers and probes for detection of tumor-derived HPV33, where the "+" signifies a locked nucleic acid. Tumor derived HPV33 DNA can be detected and distinguished from non-tumor sources using any three primer/probe sets from Table 17 within a single multiplex digital PCR reaction, where the central probe has a detection color distinct from both of the other (boundary) probes. The two boundary probes may or may not have the same color. The DNA of the primer/probe sets is modified to include quenchers, dye moieties and locked nucleic acids. In this example, droplets that are positive for the central probe's detection label and negative for the boundary/distal probes detection label contain tumor derived viral DNA.

For example, modified primer probe sets 4, 7, and 10 from Table 17 could be used for the multiplexed digital PCR reaction to detect tumor-derived HPV33 DNA, where detection probe 7 is conjugated to FAM and detection probes 4 and 10 are conjugated to HEX. Alternatively, detection 7 could be conjugated to FAM, probe 4 conjugated to HEX, and probe 10 conjugated to a different detection moiety.

In some embodiments, the primer/probe sets may be selected so that no two sets are consecutive in Table 17. For illustration, examples of triads in this embodiment with no consecutive primer probe sets include {1, 3, 5}, {1, 3, 8}, {4, 6, 9}, . . . {11, 13, 15}. Examples of triads with a consecutive primer probe set include {1, 2, 5} and {10, 12, 13}.

For the purposes of this application, digital PCR refers to any method that will be understood to those versed in the art where PCR reactions are partitioned into many sub-reactions for analysis. The partition could be droplets or microwells or any other partition used for digital PCR.

It is to be understood that HEX and FAM are used solely for clarity and illustrative purposes in all the examples.

TABLE 17

| Set | Amplicon (size) (Assay) | Detail | Named as | Sequence | $T_M{}^1$ |
|---|---|---|---|---|---|
| 1 | 1G (75 bp) (E6 assay) | Forward primer | 1G_Primer1 | 5'TTC AAG ACA CTG AGG +AAA3' (SEQ ID NO: 185) | 59.9 |
| | | Reverse primer | 1 G_Primer2 | 5'AAT GTT GT+G TAT AGT T+GT CTC3' (SEQ ID NO: 186) | 60.2 |

TABLE 17-continued

| | Amplicon (size) | | | | |
|---|---|---|---|---|---|
| Set | (Assay) | Detail | Named as | Sequence | $T_M{}^1$ |
| | | TaqMan ® probe | 1G_Probe | 5'/Dye/AAC ATT GCA/Quencher-2/TGA TTT GTG CCA AGC ATT/Quencher-1/3' (SEQ ID NO: 187) | 67.6 |
| 2 | 2G (77 bp) (E6 assay) | Forward primer | 2G_Primer1 | 5'AAT GCA AAA AAC CTT +TGC3' (SEQ ID NO: 188) | 60.1 |
| | | Reverse primer | 2G_Primer2 | 5'TCC C+TC TCT +ATA TAC A+AC T3' (SEQ ID NO: 189) | 60.2 |
| | | TaqMan ® probe | 2G_Probe | 5'/Dye/CG+A TC+T +G+AG G+T+AT/ Quencher/3' (SEQ ID NO: 190) | 67.1 |
| 3 | 3G (83 bp) (E6 assay) | Forward primer | 3G_Primer1 | 5'AAT +CCA TTT G+GA ATA TG+T A3' (SEQ ID NO: 191) | 59.8 |
| | | Reverse primer | 3G_Primer2 | 5'CCA +TAT A+CA +GAA T+AA TTA TAA TG3' (SEQ ID NO: 192) | 60 |
| | | TaqMan ® probe | 3G_Probe | 5'/Dye/CT+G +T+GT TTG +C+GGT/ Quencher/3' (SEQ ID NO: 193) | 68.2 |
| 4 | 4G (75 bp) (E6 assay) | Forward primer | 4G_Primer1 | 5'TGA +A+AT ATT AAT TA+G +GTG T3' (SEQ ID NO: 194) | 60 |
| | | Reverse primer | 4G_Primer2 | 5'TTT AAA TCC ACA TGT +CGT T3' (SEQ ID NO: 195) | 59.9 |
| | | TaqMan ® probe | 4G_Probe | 5'/Dye/TG+T GTC +C+T+C +AA+GA/ Quencher/3' (SEQ ID NO: 196) | 68 |
| 5 | 5G (82 bp) (E6 assay) | Forward primer | 5G_Primer1 | 5'CAA A+CG +ATT T+CA TAA TA+T T3' (SEQ ID NO: 197) | 59.9 |
| | | Reverse primer | 5G_Primer2 | 5'CAG TGC AGT TTC TCT ACG3' (SEQ ID NO: 198) | 59.6 |
| | | TaqMan ® probe | 5G_Probe | 5'/Dye/ACA +CG+C CGC +ACAG/ Quencher/3' (SEQ ID NO: 199) | 68.1 |
| 6 | 6G (75 bp) (E6 assay) | Forward primer | 6G_Primer1 | 5'ACA CAA GCC AAC GTT AAA3' (SEQ ID NO: 200) | 60.1 |
| | | Reverse primer | 6G_Primer2 | 5'AAT TGC TCA TA+G CA+G TAT A3' (SEQ ID NO: 201) | 59.9 |
| | | TaqMan ® probe | 6G_Probe | 5'/Dye/ATC +C+T+G AA+C +CAAC/ Quencher/3' (SEQ ID NO: 202) | 67.8 |
| 7 | 7G (83 bp) (E7 assay) | Forward primer | 7G_Primer1 | 5'AAG TGA CAG CTC AGA TGA3' (SEQ ID NO: 203) | 60.3 |
| | | Reverse primer | 7G_Primer2 | 5'TTA CA+A TGT AGT AA+T CAG CT3' (SEQ ID NO: 204) | 60.1 |
| | | TaqMan ® probe | 7G_Probe | 5'/Dye/CG+G T+C+C AA+G CCTT/ Quencher/3' (SEQ ID NO: 205) | 67.8 |
| 8 | 8G (87 bp) (E7 assay) | Forward primer | 8G_Primer1 | 5'TAACACCACAGTTCGTTTATGT3' (SEQ ID NO: 206) | 62.4 |
| | | Reverse primer | 8G_Primer2 | 5'ACAATATTCACTGTGCCCATA3' (SEQ ID NO: 207) | 61.9 |

TABLE 17-continued

| | Amplicon (size) | | | | |
|---|---|---|---|---|---|
| Set | (Assay) | Detail | Named as | Sequence | $T_M{}^1$ |
| | | TaqMan ® probe | 8G_Probe_v1 | 5'/Dye/TG +AC+C +TA+CG+A+ACC/ Quencher/3' (SEQ ID NO: 208) | 66.4 |
| | | | 8G_Probe_v2 | 5'/Dye/CAG +TA+C +AG+C A+A+GT/ Quencher/3' (SEQ ID NO: 209) | 68.3 |
| 9 | 1H (81 bp) (E6 assay) | Forward primer 1 | H_Primer1 | 5'CAA GCA TTG GAG AC+A ACT A3' (SEQ ID NO: 210) | 60.3 |
| | | Reverse primer 1 | H_Primer2 | 5'TAT ACC TCA GAT CG+T TGC3' (SEQ ID NO: 211) | 60 |
| | | TaqMan ® probe 1 | H_Probe | 5'/Dye/TC+C A+C+G CAC +TG+TA/ Quencher/3' (SEQ ID NO: 212) | 68.6 |
| 10 | 2H (75 bp) (E6 assay) | Forward primer | 2H_Primer1 | 5'TGA TT+T TGC ATT TGC AGA3' (SEQ ID NO: 213) | 60.1 |
| | | Reverse primer | 2H_Primer2 | 5'CAA A+CA CA+G TTT A+CA TAT3' (SEQ ID NO: 214) | 60 |
| | | TaqMan ® probe | 2H_Probe | 5'/Dye/TT+C +C+CT +C+T+C TATA/ Quencher/3' (SEQ ID NO: 215) | 68 |
| 11 | 3H (79 bp) (E6 assay) | Forward primer | 3H_Primer1 | 5'GTT +C+TT AT+C TAA AAT TA+G TG3' (SEQ ID NO: 216) | 59.7 |
| | | Reverse primer | 3H_Primer2 | 5'TTT AAC TG+T TTG TTC +TAA TGT3' (SEQ ID NO: 217) | 60 |
| | | TaqMan ® probe | 3H_Probe_v1 | 5'/Dye/TT+C +C+AT ATA +C+A+GA/ Quencher/3' (SEQ ID NO: 218) | 65 |
| | | | 3H_Probe_v2 | 5'/Dye/T+CT G+TA TA+T +G+G+AA/ Quencher/3' (SEQ ID NO: 219) | 65 |
| 12 | 4H (80 bp) (E6 assay) | Forward primer | 4H_Primer1 | 5'AGG TGT ATT ATA T+GT CAA A+GA3' (SEQ ID NO: 220) | 59.9 |
| | | Reverse primer | 4H_Primer2 | 5'ATA TTA TGA AAT +C+G+T TTG TT3' (SEQ ID NO: 221) | 60.2 |
| | | TaqMan ® probe | 4H_Probe_v1 | 5'/Dye/TT+G T+GT +C+C+T CA+AG/ Quencher/3' (SEQ ID NO: 222) | 67.9 |
| | | | 4H_Probe_v2 | 5'/Dye/CG+A +CAT GT+G +G+ATT/ Quencher/3' (SEQ ID NO: 223) | 67 |
| 13 | 5H(74 bp) (E6 assay) | Forward primer | 5H_Primer1 | 5'AG+G +AAT ATG T+TT TA+G ATT3' (SEQ ID NO: 224) | 60.1 |
| | | Reverse primer | 5H_Primer2 | 5'ATC TGA GCT GTC ACT +TAA3' (SEQ ID NO: 225) | 60.2 |
| | | TaqMan ® probe | 5H_probe | 5'/Dye/TG+A +C+C+T A+TA +CTGC/ Quencher/3' (SEQ ID NO: 226) | 68.1 |
| 14 | 6H (77 bp) (E7 assay) | Forward primer | 6H_Primer1 | 5'GAG GAT GAA GGC TTG GA3' (SEQ ID NO: 227) | 60.6 |
| | | Reverse primer | 6H_Primer2 | 5'TGA CA+A CAG GTT A+CA AT3' (SEQ ID NO: 228) | 60.3 |

TABLE 17-continued

Primers and probes for HPV33

| Set | Amplicon (size) (Assay) | Detail | Named as | Sequence | $T_M{}^1$ |
|---|---|---|---|---|---|
| | | TaqMan ® probe | 6H_probe | 5'/Dye/CCA GAT GGA /Quencher-2/CAA GCA CAA CCA GC/Quencher-1/3' (SEQ ID NO: 229) | 67.7 |
| 15 | 7H (77 bp) (E7 assay) | Forward primer | 7H_Primer1 | 5'TGT CA+A CAG TAC AGC AA3' (SEQ ID NO: 230) | 60 |
| | | Reverse primer | 7H_Primer2 | 5'AGG TAG GGC ACA CAA TAT3' (SEQ ID NO: 231) | 60.2 |
| | | TaqMan ® probe | 7H_Probe | 5'/Dye/AC+C +ATA +C+A+G +CAAC/Quencher/3' (SEQ ID NO: 232) | 68.1 |

[1]"Dye" stands for a fluorescent reporter dye.
Any reporter dyes such as FAM ™, HEX ™, VIC ®, Cy5 ™, and Cy5.5 ™ that is compatible with the detection channels for the instrument can be used.
A quencher compatible with the respective dye was used at 3' end of the probe (Quencher-1).
A second quencher (Quencher-2) such as ZEN was sometimes placed internally between 9th and 10th nucleotide base from the reporter dye to enhance the overall dye quenching.
[2]These estimates of melting temperature(TM) were calculated using IDT'S oligo analyzer tools with following settings:
(a) For primers:
Target type = DNA,
Oligo concentration = 0.9 μM,
Nat concentration = 50 mM,
Mg++ concentration = 3 mM, and
dNTPs concentration = 0.8 mM.
(b) for Probe:
Target type = DNA,
Oligo concentration = 0.25 μM,
Nat concentration = 50 mM,
Mg++ concentration = 3 mM, and
dNTPs concentration = 0.8 mM.
[3]+ = Locked nucleic acid

Example 11: Modified Oligonucleotide Compositions and Methods for Detection of Tumor-Derived HPV35

Provided in Table 18 below are primers and probes for detection of tumor-derived HPV35, where the "+" signifies a locked nucleic acid. Tumor derived HPV35 DNA can be detected and distinguished from non-tumor sources using any three primer/probe sets from Table 18 within a single multiplex digital PCR reaction, where the central probe has a detection color distinct from both of the other (boundary) probes. The two boundary probes may or may not have the same color. The DNA of the primer/probe sets is modified to include quenchers, dye moieties and locked nucleic acids. In this example, droplets that are positive for the central probe's detection label and negative for the boundary/distal probes detection label contain tumor derived viral DNA.

For example, modified primer probe sets 4, 7, and 10 from Table 18 could be used for the multiplexed digital PCR reaction to detect tumor-derived HPV35 DNA, where detection probe 7 is conjugated to FAM and detection probes 4 and 10 are conjugated to HEX. Alternatively, detection 7 could be conjugated to FAM, probe 4 conjugated to HEX, and probe 10 conjugated to a different detection moiety.

In some embodiments, the primer/probe sets may be selected so that no two sets are consecutive in Table 18. For illustration, examples of triads in this embodiment with no consecutive primer probe sets include {1, 3, 5}, {1, 3, 8}, {4, 6, 9}, ... {12, 14, 16}. Examples of triads with a consecutive primer probe set include {1, 2, 5} and {10, 12, 13}.

For the purposes of this application, digital PCR refers to any method that will be understood to those versed in the art where PCR reactions are partitioned into many sub-reactions for analysis. The partition could be droplets or microwells or any other partition used for digital PCR.

It is to be understood that HEX and FAM are used solely for clarity and illustrative purposes in all the examples.

TABLE 18

Primers and probes for HPV35

| Set | Amplicon (size) (Assay) | Detail | Named as | Sequence | $T_M{}^1$ |
|---|---|---|---|---|---|
| 1 | 1I (78 bp) (E6 assay) | Forward primer | 1I_Primer1 | 5'CTG A+AC G+AC CTT ACA AA3' (SEQ ID NO: 233) | 59.9 |
| | | Reverse primer | 1I_Primer2 | 5'ATA CAC AAT T+CA AA+C +AAA3' (SEQ ID NO: 234) | 60.3 |

TABLE 18-continued

Primers and probes for HPV35

| Set | Amplicon (size) (Assay) | Detail | Named as | Sequence | T_M¹ |
|---|---|---|---|---|---|
| | | TaqMan ® probe | 1I_Probe | 5'/Dye/TGA TTT GTG /Quencher-2/CAA CGA GGT AGA AGA AAG C/Quencher-1/3' (SEQ ID NO: 235) | 67.5 |
| | | | 1I_probe_v2 | 5'/Dye/CG+A G+G+T +A+GA A+GAA/ Quencher/3' (SEQ ID NO: 236) | 67.4 |
| 2 | 2I (72 bp) (E6 assay) | Forward primer | 2I_Primer1 | 5'CAA A+CA AGA A+TT AC+A GC3' (SEQ ID NO: 237) | 60 |
| | | Reverse primer | 2I_Primer2 | 5'CCT +T+CT +CTA TAT A+CT ATA3' (SEQ ID NO: 238) | 59.9 |
| | | TaqMan ® probe | 2I_probe | 5'/Dye/AG+T +C+A+T ATA +C+CT CAC/Quencher/3' (SEQ ID NO: 239) | 67.5 |
| 3 | 3I (80 bp) (E6 assay) | Forward primer | 3I_Primer1 | 5'ATT +C+AA AAA TAA +G+TG AAT3' (SEQ ID NO: 240) | 59.7 |
| | | Reverse primer | 3I_Primer2 | 5'TAA CTG TTT GTT +GCA TTG T3' (SEQ ID NO: 241) | 59.8 |
| | | TaqMan ® probe | 3I_Probe | 5'/Dye/TA+G +T+GT GTA +T+G+GA/ Quencher/3' (SEQ ID NO: 242) | 68.1 |
| 4 | 4I (75 bp) (E6 assay) | Forward primer | 4I_Primer1 | 5'TGT CAT T+TA +T+TA ATT +AGG T3' (SEQ ID NO: 243) | 60 |
| | | Reverse primer | 4I_Primer2 | 5'TTC TTC TAA +ATG T+CT TTG C3' (SEQ ID NO: 244) | 60 |
| | | TaqMan ® probe | 4I_Probe | 5'/Dye/TG+T +CAA AAA +C+C+GC/ Quencher/3' (SEQ ID NO: 245) | 68.4 |
| 5 | 5I (74 bp) (E6 assay) | Forward primer | 5I_Primer1 | 5'CGA TTC CAT AAC +ATC GGT3' (SEQ ID NO: 246) | 60 |
| | | Reverse primer | 5I_Primer2 | 5'TCG GTT TCT CTA CGT GT3' (SEQ ID NO: 247) | 59.7 |
| | | TaqMan ® probe | 5I_Probe | 5'/Dye/CG+G +T+G+T AT+G +TCCT/ Quencher/3' (SEQ ID NO: 248) | 68.1 |
| 6 | 6I (75 bp) (E7 assay) | Forward primer | 6I_Primer1 | 5'CAT GGA +GA+A ATA ACT A+CA3' (SEQ ID NO: 249) | 60 |
| | | Reverse primer | 6I_Primer2 | 5'CTC ATA ACA +GTA +TA+G GTC3' (SEQ ID NO: 250) | 60.2 |
| | | TaqMan ® probe | 6I_Probe | 5'/Dye/TG+C AA+G A+C+T A+T+GT/ Quencher/3' (SEQ ID NO: 251) | 67.5 |
| 7 | 7I (79 bp) (E7 assay) | Forward primer | 7I_Primer1 | 5'AAT T+GT GTG ACA GCT CA3' (SEQ ID NO: 252) | 60.1 |
| | | Reverse primer | 7I_Primer2 | 5'TAA TTG GAG GTG TCT GGT3' (SEQ ID NO: 253) | 60 |
| | | TaqMan ® probe | 7I_Probe | 5'/Dye/TT+G +C+TT +GTC +C+AGC/ Quencher/3' (SEQ ID NO: 254) | 68.1 |
| 8 | 8I (92 bp) (E7 assay) | Forward primer | 8I_Primer1 | 5'TA+A TAT TGT AAC GT+C CTG T3' (SEQ ID NO: 255) | 60 |
| | | Reverse primer | 8I_Primer2 | 5'AT+A A+AT CTT C+CA ATT +TAC G3' (SEQ ID NO: 256) | 59.9 |

TABLE 18-continued

| Set | Amplicon (size) (Assay) | Detail | Named as | Sequence | $T_M{}^1$ |
|---|---|---|---|---|---|
| | | TaqMan ® probe | 8I_Probe | 5'/Dye/CA+C +TA+C +G+TC TG+TG/ Quencher/3' (SEQ ID NO: 257) | 67.4 |
| 9 | U (72 bp) (E6 assay) | Forward primer | 1J_Primer1 | 5'TGC ATG ATT TGT +GCA AC3' (SEQ ID NO: 258) | 60.1 |
| | | Reverse primer | 1J_Primer2 | 5'CTT G+TT TGC AGT A+TA CAC3' (SEQ ID NO: 259) | 60.1 |
| | | TaqMan ® probe | 1J_Probe | 5'/Dye/AAA G+C+A T+C+C +AT+GA/ Quencher/3' (SEQ ID NO: 260) | 68.1 |
| 10 | 2J (95 bp) (E6 assay) | Forward primer | 2J_Primer1 | 5'CAG CGG AGT GAG GTA TAT3' (SEQ ID NO: 261) | 60 |
| | | Reverse primer | 2J_Primer2 | 5'AAT T+TT A+AA +CAT TT+C +ATG3' (SEQ ID NO: 262) | 60 |
| | | TaqMan ® probe | 2J_Probe | 5'/Dye/AG+A G+AA G+GC C+A+GC/ Quencher/3' (SEQ ID NO: 263) | 68 |
| 11 | 3J (76 bp) (E6 assay) | Forward primer | 3J_Primer1 | 5'AAT +ATA +GAT G+GT ATA +G+AT ATA3' (SEQ ID NO: 264) | 60 |
| | | Reverse primer | 3J_Primer2 | 5'AAT A+AA T+GA +CAT AAC T+GT TT3' (SEQ ID NO: 265) | 60.1 |
| | | TaqMan ® probe | 3J_Probe | 5'/Dye/TT+C +T+C+C A+TA +CACA/ Quencher/3' (SEQ ID NO: 266) | 67.8 |
| 12 | 4J (75 bp) (E6 assay) | Forward primer | 4J_Primer1 | 5'AA+T TA+G GT+G TAT TAC A+TG3' (SEQ ID NO: 267) | 59.8 |
| | | Reverse primer | 4J_Primer2 | 5'AAT +CGT TTT +TTT T+CT TCT3' (SEQ ID NO: 268) | 60 |
| | | TaqMan ® probe | 4J_Probe | 5'/Dye/C+C+A +G+TT +GAA AA+GCA/ Quencher/3' (SEQ ID NO: 269) | 67.3 |
| 13 | 5J (74 bp) (E6 assay) | Forward primer | 5J_Primer1 | 5'CC+A TAA CAT CGG TGG AC3' (SEQ ID NO: 270) | 60.1 |
| | | Reverse primer | 5J_Primer2 | 5'AC+A CCT CGG TTT CTC TA3' (SEQ ID NO: 271) | 60.1 |
| | | TaqMan ® probe | 5J_Probe | 5'/Dye/TGT +ATG +T+C+C +TG+TT/ Quencher/3' (SEQ ID NO: 272) | 67.9 |
| 14 | 6J (77 bp) (E7 assay) | Forward primer | 6J_Primer1 | 5'TTT AGA TTT GGA +ACC CGA3' (SEQ ID NO: 273) | 60 |
| | | Reverse primer | 6J_Primer2 | 5'TAT CTT CCT CCT +CCT CT3' (SEQ ID NO: 274) | 60.2 |
| | | TaqMan ® probe | 6J_Probe | 5'/Dye/AC+T +G+A+C +CTA TA+CT/ Quencher/3' (SEQ ID NO: 275) | 68.3 |
| 15 | 7J (73 bp) (E7 assay) | Forward primer | 7J_Primer1 | 5'CTA TTG ACG GTC CAG CT3' (SEQ ID NO: 276) | 60.5 |
| | | Reverse primer | 7J_Primer2 | 5'CAT TTA C+AA C+AG GAC GTT3' (SEQ ID NO: 277) | 60 |
| | | TaqMan ® probe | 7J_Probe | 5'/Dye/CCA +G+A+C +A+CC+TCC/ Quencher/3' (SEQ ID NO: 278) | 68.7 |

TABLE 18-continued

Primers and probes for HPV35

| Set | Amplicon (size) (Assay) | Detail | Named as | Sequence | $T_M{}^1$ |
|---|---|---|---|---|---|
| 16 | 8J (75 bp) (E7 Assay) | Forward primer | 8J_Primer1 | 5'TGA GGC GAC ACT ACG TC3' (SEQ ID NO: 279) | 62.9 |
| | | Reverse primer | 8J_Primer2 | 5'GTG CCC ATT AAT AAA TCT TCC AA3' (SEQ ID NO: 280) | 61.7 |
| | | TaqMan ® probe | 8J_Probe | 5'/Dye/AG+AG+C+ACA+C+ACAT/Quencher/3' (SEQ ID NO: 281) | 67.5 |
| | | Reverse primer | 1I_Primer1 | 5'CTG A+AC G+AC CTT ACA AA3' (SEQ ID NO: 282) | 59.9 |
| | | TaqMan ® probe | 1I_Primer2 | 5'ATA CAC AAT T+CA AA+C +AAA3' (SEQ ID NO: 283) | 60.3 |

[1]"Dye" stands for a fluorescent reporter dye.
Any reporter dyes such as FAM ™, HEX ™, VIC ®, Cy5 ™, and Cy5.5 ™ that is compatible with the detection channels for the instrument can be used.
A quencher compatible with the respective dye was used at 3' end of the probe (Quencher-1).
A second quencher (Quencher-2) such as ZEN was sometimes placed internally between [9th] and [10th] nucleotide base from the reporter dye to enhance the overall dye quenching.
[2]These estimates of melting temperature(TM) were calculated using IDT'S oligo analyzer tools with following settings:
(a) For primers:
Target type = DNA,
Oligo concentration = 0.9 μM,
Nat concentration = 50 mM,
$Mg^{++}$ concentration = 3 mM, and
dNTPs concentration = 0.8 mM.
(b) for Probe:
Target type = DNA,
Oligo concentration = 0.25 μM,
Nat concentration = 50 mM,
$Mg^{++}$ concentration = 3 mM, and
dNTPs concentration = 0.8 mM.
[3]+ = Locked nucleic acid

Example 12: Modified Oligonucleotide Compositions and Methods for Detection of Tumor-Derived HPV45

Provided in Table 19 below are primers and probes for detection of tumor-derived HPV45, where the "+" signifies a locked nucleic acid. Tumor derived HPV45 DNA can be detected and distinguished from non-tumor sources using any three primer/probe sets from Table 19 within a single multiplex digital PCR reaction, where the central probe has a detection color distinct from both of the other (boundary) probes. The two boundary probes may or may not have the same color. The DNA of the primer/probe sets is modified to include quenchers, dye moieties and locked nucleic acids. In this example, droplets that are positive for the central probe's detection label and negative for the boundary/distal probes detection label contain tumor derived viral DNA.

For example, modified primer probe sets 4, 7, and 10 from Table 19 could be used for the multiplexed digital PCR reaction to detect tumor-derived HPV45 DNA, where detection probe 7 is conjugated to FAM and detection probes 4 and 10 are conjugated to HEX. Alternatively, detection 7 could be conjugated to FAM, probe 4 conjugated to HEX, and probe 10 conjugated to a different detection moiety.

In some embodiments, the primer/probe sets may be selected so that no two sets are consecutive in Table 19. For illustration, examples of triads in this embodiment with no consecutive primer probe sets include {1, 3, 5}, {1, 3, 8}, {4, 6, 9}, . . . {13, 15, 17}. Examples of triads with a consecutive primer probe set include {1, 2, 5} and {10, 12, 13}.

For the purposes of this application, digital PCR refers to any method that will be understood to those versed in the art where PCR reactions are partitioned into many sub-reactions for analysis. The partition could be droplets or microwells or any other partition used for digital PCR.

It is to be understood that HEX and FAM are used solely for clarity and illustrative purposes in all the examples.

TABLE 19

Primers and probes for HPV45

| Set | Amplicon (size) (Assay) | Detail | Named as | Sequence | $T_M{}^1$ |
|---|---|---|---|---|---|
| 1 | 1K (74 bp) (E6 assay) | Forward primer | 1K_Primer1 | 5'CGC TTT GAC GAT CCA AA3' (SEQ ID NO: 284) | 60 |
| | | Reverse primer | 1 K_Primer2 | 5'TCT +TGT A+GT GAT G+TA TTC3' (SEQ ID NO: 285) | 60.0 |

TABLE 19-continued

| | | | | | |
|---|---|---|---|---|---|
| Set | Amplicon (size) (Assay) | Detail | Named as | Sequence | $T_M$[1] |
| | | | | Primers and probes for HPV45 | |
| | | TaqMan ® probe | 1 K_Probe | 5'/Dye/AG+C +TA+C +C+AG +ATT/Quencher/3' (SEQ ID NO: 286) | 68.4 |
| 2 | 2K (85 bp) (E6 assay) | Forward primer | 2K_Primer1 | 5'CGT ATC TA+T TGC CTG TGT A3' (SEQ ID NO: 287) | 60.4 |
| | | Reverse primer | 2K_Primer2 | 5'CAC TAT A+C+A +TAA AT+C TTT AA3' (SEQ ID NO: 288) | 60 |
| | | TaqMan ® probe | 2K_Probe | 5'/Dye/AGC AAC ATT /Quencher-2/GGA ACG CAC AGA GGT ATA TC/Quencher-1/3' (SEQ ID NO: 289) | 68.4 |
| 3 | 3K (74 bp) (E6 assay) | Forward primer | 3K_Primer1 | 5'ATA GAG A+CT +GTA T+AG CA3' (SEQ ID NO: 290) | 60 |
| | | Reverse primer | 3K_Primer2 | 5'ATA T+CT TAA TT+C +T+CT AAT TC3' (SEQ ID NO: 291) | 60.1 |
| | | TaqMan ® probe | 3K_Probe | 5'/Dye/TA+C +ATT TA+T +G+G+CAT/Quencher/3' (SEQ ID NO: 292) | 66.2 |
| 4 | 4K (75 bp) (E6 assay) | Forward primer | 4K_Primer1 | 5'TAT T+CA AAC +T+CT GTA +TAT3' (SEQ ID NO: 293) | 60 |
| | | Reverse primer | 4K_Primer2 | 5'CAC +C+TT ATT AA+C +AAA TTA T3' (SEQ ID NO: 294) | 59.9 |
| | | TaqMan ® probe | 4K_Probe | 5'/Dye/TC+C +AGT G+T+C T+CT C/Quencher/3' (SEQ ID NO: 295) | 68.1 |
| 5 | 5K (70 bp) (E6 assay) | Forward primer | 5K_Primer1 | 5'CCA GA+A ACC +ATT GAA CC3' (SEQ ID NO: 296) | 60 |
| | | Reverse primer | 5K_Primer2 | 5'AGC TAT GCT GTG AA+A TCT3' (SEQ ID NO: 297) | 60.1 |
| | | TaqMan ® probe | 5K_Probe | 5'/Dye/CG+T +AG+A +C+AC +CTT/Quencher/3' (SEQ ID NO: 298) | 67.4 |
| 6 | 6K (70 bp) (E6 assay) | Forward primer | 6K_Primer1 | 5'CGA GGG CAG TGT A+AT AC3' (SEQ ID NO: 299) | 60.3 |
| | | Reverse primer | 6K_Primer2 | 5'CTT GTG T+TT CCC TAC GT3' (SEQ ID NO: 300) | 60.4 |
| | | TaqMan ® probe | 6K_Probe_v1 | 5'/Dye/CC+T +GG+T +CAC +A+ACA/Quencher/3' (SEQ ID NO: 301) | 67.5 |
| | | | 6K_Probe_v2 | 5'/Dye/TGA CCA GGC /Quencher-2/ACG GCA AGA AAG A/Quencher-1/3' (SEQ ID NO: 302) | 68.6 |
| 7 | 7K (73 bp) (E7 assay) | Forward primer | 7K_Primer1 | 5'AAC ACT GCA AGA AAT +TGT A3' (SEQ ID NO: 303) | 60.1 |
| | | Reverse primer | 7K_Primer2 | 5'CTC GTA ACA CA+A CAG GT3' (SEQ ID NO: 304) | 60.2 |
| | | TaqMan® probe | 7K_Probe | 5'/Dye/TGG AA+C +CT+C A+G+AA/Quencher/3' (SEQ ID NO: 305) | 68.3 |
| 8 | 8K (71 bp) (E7 assay) | Forward primer | 8K_Primer1 | 5'CAA TTA AGC G+AG TCA GAG3' (SEQ ID NO: 306) | 60 |
| | | Reverse primer | 8K_Primer2 | 5'GTC GGG CTG GTA GTT GT3' (SEQ ID NO: 307) | 58.8 |

TABLE 19-continued

| | | | | | |
|---|---|---|---|---|---|
| | | | | Primers and probes for HPV45 | |
| Set | Amplicon (size) (Assay) | Detail | Named as | Sequence | $T_M$[1] |
| | | TaqMan® probe | 8K_Probe | 5'/Dye/CG+A +T+G+A AGC +AG+AT/ Quencher/3' (SEQ ID NO: 308) | 68 |
| 9 | 9K (85 bp) (E7 assay) | Forward primer | 9K_Primer1 | 5'AAT TTT GT+G +TGT ATG +TTG3' (SEQ ID NO: 309) | 59.8 |
| | | Reverse primer | 9K_Primer2 | 5'CTG +CTG TAG T+GT TCT AA3' (SEQ ID NO: 310) | 59.7 |
| | | TaqMan® probe | 9K_Probe | 5'/Dye/AC+G +G+CA +G+AA +TTGA/ Quencher/3' (SEQ ID NO: 311) | 68 |
| 10 | 1L (75 bp) (E6 assay) | Forward primer | 1L_Primer1 | 5'CCT ACA AGO +TAC CAG ATT3' (SEQ ID NO: 312) | 60.1 |
| | | Reverse primer | 1L_Primer2 | 5'TGC AAT ATA CAC AGG C+AA3' (SEQ ID NO: 313) | 59.8 |
| | | TaqMan® probe | 1L_Probe | 5'/Dye/CA+C TA+C +AA+G +A+CGT/ Quencher/3' (SEQ ID NO: 314) | 67.8 |
| 11 | 2L (75 bp) (E6 assay) | Forward primer | 2L_Primer1 | 5'AAC ATT GGA ACG CAC AG3' (SEQ ID NO: 315) | 60.3 |
| | | Reverse primer | 2L_Primer2 | 5'TAT GCT ATA CAG TCT C+TA TAC AC3' (SEQ ID NO: 316) | 60.3 |
| | | TaqMan® probe | 2L_Probe | 5'/Dye/AG+G +T+AT A+T+C AAT TTG+CTT/Quencher/3' (SEQ ID NO: 317) | 67.8 |
| 12 | 3L (70 bp) (E6 assay) | Forward primer | 3L_Primer1 | 5'CAT +GCC ATA +AAT GTA TAG +AC3' (SEQ ID NO: 318) | 60.1 |
| | | Reverse primer | 3L_Primer2 | 5'CC+A TA+T ACA GA+G TTT GAA T3' (SEQ ID NO: 319) | 59.7 |
| | | TaqMan® probe | 3L_Probe | 5'/Dye/T+C+C +A+GA ATT A+G+A GA (SEQ ID NO: 320) | 68.3 |
| 13 | 4L (84 bp) (E6 assay) | Forward primer | 4L_Primer1 | 5'AAT AAC T+AA TA+C AG+A GTT GT3' (SEQ ID NO: 321) | 60.1 |
| | | Reverse primer | 4L_Primer2 | 5'TGT CTA CGT TTT T+CT GC3' (SEQ ID NO: 322) | 59.9 |
| | | TaqMan® probe | 4L_Probe_v1 | 5'/Dye/AA+C +C+AT T+G+A +ACCC/ Quencher/3' (SEQ ID NO: 323) | 67.9 |
| | | | 4L_Probe_v2 | 5'/Dye/TTG TTA ATA /Quencher-2/AGG TGC CTG CGG TGC/Quencher-1/3' (SEQ ID NO: 324) | 67.7 |
| 14 | 5L (91 bp) (E6 assay) | Forward primer | 5L_Primer1 | 5'TTA AGG A+CA AAC +GAA GAT3' (SEQ ID NO: 325) | 60 |
| | | Reverse primer | 5L_Primer2 | 5'AAG TCT TTC TTG CCG TG3' (SEQ ID NO: 326) | 59.6 |
| | | TaqMan® probe | 5L_Probe_v1 | 5'/Dye/TGG ACA GTA /Quencher-2/CCG AGG GCA GTG TAA TA/Quencher-1/3' (SEQ ID NO: 327) | 68.4 |
| | | | 5L_Probe_v2 | 5'/Dye/TAG CTG GAC /Quencher-2/AGT ACC GAG GGC A/Quencher-1/3' (SEQ ID NO: 328) | 68.7 |
| 15 | 6L (75 bp) (E7 assay) | Forward primer | 6L_Primer 1 | 5'TCA GA+A TGA ATT +AGA TOO TG3' (SEQ ID NO: 329) | 60.1 |

TABLE 19-continued

| | | | | Primers and probes for HPV45 | | |
|---|---|---|---|---|---|
| Set | Amplicon (size) (Assay) | Detail | Named as | Sequence | $T_M{}^1$ |
| | | Reverse primer | 6L_Primer2 | 5'TGC TTC ATC GTT TTC CTC3' (SEQ ID NO: 330) | 59.8 |
| | | TaqMan® probe | 6L_Probe | 5'/Dye/TGA +C+C+T +GTT GT+G T/Quencher/3' (SEQ ID NO: 331) | 67.9 |
| 16 | 7L (75 bp) (E7 assay) | Forward primer | 7L_Primer1 | 5'TAG TCA TGC ACA ACT +ACC3' (SEQ ID NO: 332) | 59.7 |
| | | Reverse primer | 7L_Primer2 | 5'TCA CAC TTA CAA CAT A+CA C3' (SEQ ID NO: 333) | 59.8 |
| | | TaqMan® probe | 7L_Probe | 5'/Dye/CCG A+CG +A+GC CGA/Quencher/3' (SEQ ID NO: 334) | 67.5 |
| 17 | 8L (90 bp) (E7 assay) | Forward primer | 8L_Primer1_v1 | 5'CGG CAG AAT TGA GCT TAG A3' (SEQ ID NO: 335) | 62.4 |
| | | | 8L_Primer1_v2 | 5'CGG CAG AAT TGA GCT TAC3' (SEQ ID NO: 336) | 60.4 |
| | | Reverse primer | 8L_Primer2_v1 | 5'GGA CAC ACA AAG GAC AAG G3' (SEQ ID NO: 337) | 62.7 |
| | | | 8L_Primer2_v2 | 5'GGA CAC ACA AAG GAC AAG3' (SEQ ID NO: 338) | 60.2 |
| | | TaqMan® probe | 8L_Probe_v1 | 5'/Dye/TCG GCA GA+G G+A+CC/ Quencher/3' (SEQ ID NO: 339) | 65.7 |
| | | | 8L_Probe_v2 | 5'/Dye/TCG GC+A GA+G G+A+CC/ Quencher/3' (SEQ ID NO: 340) | 68.3 |

[1]"Dye" stands for a fluorescent reporter dye. Any reporter dyes such as FAM™, HEX™, VIC®, Cy5™, and Cy5.5™ that is compatible with the detection channels for the instrument can be used. A quencher compatible with the respective dye was used at 3' end of the probe (Quencher-1). A second quencher (Quencher-2) such as ZEN was sometimes placed internally between 9th and 10th nucleotide base from the reporter dye to enhance the overall dye quenching.

[2]These estimates of melting temperature (TM) were calculated using IDT'S oligo analyzer tools with following settings: (a) For primers: Target type = DNA, Oligo concentration = 0.9 pM, Nat concentration = 50 mM, Mg++ concentration = 3 mM, and dNTPs concentration = 0.8 mM. (b) for Probe: Target type = DNA, Oligo concentration = 0.25 pM, Nat concentration = 50 mM, Mg++ concentration = 3 mM, and dNTPs concentration = 0.8 mM.

[3]+ = Locked nucleic acid

Example 13: Modified Oligonucleotide Compositions and Methods for Detection of Tumor-Derived EBV Provided in Table 20 below are primers and probes for detection of tumor-derived EBV, where the "+" signifies a locked nucleic acid. Tumor derived EBV DNA can be detected and distinguished from non-tumor sources using any three consecutive primer/probe sets from Table 20 within a single multiplex digital PCR reaction, where the central probe has a detection color distinct from both of the other (boundary) probes. The two boundary probes may or may not have the same color. In this example, droplets that are positive for the central probe's detection label and negative for the boundary/distal probes detection label contain tumor derived viral DNA.

For example, modified primer probe sets 4, 5, and 6 from Table 20 could be used for the multiplexed digital PCR reaction to detect tumor-derived EBV DNA, where detection probe 5 is conjugated to FAM and detection probes 4 and 6 are conjugated to HEX. Alternatively, detection 5 could be conjugated to FAM, probe 4 conjugated to HEX, and probe 6 conjugated to a different detection moiety.

For illustration, examples of three consecutive primer probe sets include {1, 2, 3}, {2, 3, 4}, {3, 4, 5}, . . . {15, 16, 17}.

For the purposes of this application, digital PCR refers to any method that will be understood to those versed in the art where PCR reactions are partitioned into many sub-reactions for analysis. The partition could be droplets or microwells or any other partition used for digital PCR.

It is to be understood that HEX and FAM are used solely for clarity and illustrative purposes in all the examples.

TABLE 20

| | Amplicon (size) | | | | |
|---|---|---|---|---|---|
| Set | (Assay) | Detail | Named as | Sequence | $T_M^1$ |
| 1 | 1M (70 bp) | Forward primer | 1M_Primer1 | 5'GGG AGA CΘG AAG TGA A3' (SEQ ID NO: 341) | 59.9 |
| | | Reverse primer | 1M_Primer2 | 5'TCC ACT TAC CTC TGG C3' (SEQ ID NO: 342) | 59.7 |
| | | TaqMan ® probe | 1M_Probe | 5'/Dye/CT+G GA+C C+A+A +CCC G/Quencher/3' (SEQ ID NO: 343) | 68 |
| 2 | 2M (80 bp) | Forward primer | 2M_Primer1 | 5'CTC GGA CAG CTC CTA AG3' (SEQ ID NO: 344) | 60.3 |
| | | Reverse primer | 2M_Primer2 | 5'ACC CTT CT+A CGG ACT C3' (SEQ ID NO: 345) | 60.2 |
| | | TaqMan ® probe | 2M_Probe | 5'/Dye/CG+C CCA GT+C +CT+A C/Quencher/3' (SEQ ID NO: 346) | 68.5 |
| 3 | 3M (87 bp) | Forward primer | 3M_Primer1 | 5'TCT CTT AGA GAG +TGG CT3' (SEQ ID NO: 347) | 60.8 |
| | | Reverse primer | 3M_Primer2 | 5'TTC TTC +TAT G+TA GAC +AGA3' (SEQ ID NO: 348) | 60.4 |
| | | TaqMan ® probe | 3M_Probe | 5'/Dye/CG+C +ATT A+G+A +G+ACC/Quencher/3' (SEQ ID NO: 349) | 68.5 |
| 4 | 4M (78 bp) | Forward primer | 4M_Primer1 | 5'TGC CTA C+AT +TCT +ATC TTG3' (SEQ ID NO: 350) | 59.9 |
| | | Reverse primer | 4M_Primer2 | 5'ACG GGT TTC CAA GAC TA3' (SEQ ID NO: 351) | 59.8 |
| | | TaqMan ® probe | 4M_Probe | 5'/Dye/TA+T +G+TT TG+T +CC+CC/Quencher/3' (SEQ ID NO: 352) | 69.1 |
| 5 | 5M (75 bp) | Forward primer | 5M_Primer1 | 5'CAC TCT CAG TA+A TTC CCT C3' (SEQ ID NO: 353) | 60.2 |
| | | Reverse primer | 5M_Primer2 | 5'CAA AGA +TT+G TTA GTG G+AA T3' (SEQ ID NO: 354) | 60 |
| | | TaqMan ® probe | 5M_Probe | 5'/Dye/TCC +CTA +CC+A +GG+A A/Quencher/3' (SEQ ID NO: 355) | 68.6 |
| 6 | 6M (76 bp) | Forward primer | 6M_Primer1 | 5'CCG CTA GGA TAT GAC GT3' (SEQ ID NO: 356) | 59.9 |
| | | Reverse primer | 6M_Primer2 | 5'TTA CAA TAT +AAT TA+G +C+CA3' (SEQ ID NO: 357) | 59.9 |
| | | TaqMan ® probe | 5M_Probe | 5'/Dye/ACC TCT AGC /Quencher-2/ATC TGC TAT GCG AAT GC/Quencher-1/3' (SEQ ID NO: 358) | 68.2 |
| 7 | 17M (81 bp) | Forward primer | 7M_Primer1 | 5'GCT TAC CCC TCC ACA A3' (SEQ ID NO: 359) | 60.4 |
| | | Reverse primer | 7M_Primer2 | 5'GGC ACC GTT AGT GTT G3' (SEQ ID NO: 360) | 59.7 |
| | | TaqMan ® probe | 7M_Probe | 5'/Dye/TAC CCC TCC /Quencher-2/TAC CCC TCT GCC/Quencher-1/3' (SEQ ID NO: 361) | 68.5 |
| 8 | 8M (91 bp) | Forward primer | 8M_Primer1 | 5'TAC CGA ACT TCA ACC CA3' (SEQ ID NO: 362) | 60.1 |
| | | Reverse primer | 8M_Primer2 | 5'TTG +ATG AGT AAG AGG GTG3' (SEQ ID NO: 363) | 59.9 |

TABLE 20-continued

| | | Primers and probes for Epstein-Barr virus (EBV) | | | |
|---|---|---|---|---|---|
| Set | Amplicon (size) (Assay) | Detail | Named as | Sequence | $T_M{}^1$ |
| | | TaqMan ® probe | 8M_Probe_v1 | 5'/Dye/CC+A TCA C+CA +C+C+AC/ Quencher/3' (SEQ ID NO: 364) | 68.9 |
| | | | 8M_Probe_v2 | 5'/Dye/TG+C +C+AG A+CC AATC/ Quencher/3' (SEQ ID NO: 365) | 68.4 |
| 9 | 9M (75 bp) | Forward primer | 9M_Primer1 | 5'AGC ACC CCA +AAT GAT C3' (SEQ ID NO: 366) | 60.2 |
| | | Reverse primer | 9M_Primer2 | 5'TAA TGG +CAT AGG TGG AA3' (SEQ ID NO: 367) | 59.8 |
| | | TaqMan ® probe | 9M_Probe | 5'/Dye/TCC AGA ACC /Quencher-2/ACG TCC CCC G/Quencher-1/3' (SEQ ID NO: 368) | 68.1 |
| 10 | 10M (87 bp) | Forward primer | 10M_Primer1 | 5'ATC AAC GAC CAA CAA +TTA C3' (SEQ ID NO: 369) | 60 |
| | | Reverse primer | 10M_Primer2 | 5'TTG AGT CTT AGA GGG T+TG3' (SEQ ID NO: 370) | 60.1 |
| | | TaqMan ® probe | 10M_Probe | 5'/Dye/CC+C +GAG +GG+T AG+A T/Quencher/ 3' (SEQ ID NO: 371) | 68.8 |
| 11 | 11M (76 bp) | Forward primer | 11M_Primer1 | 5'TTG GAG ACC AGA GCC3' (SEQ ID NO: 372) | 59.6 |
| | | Reverse primer | 11M_Primer2 | 5'TTG TCC CTG ATG AAG +AC3' (SEQ ID NO: 373) | 60.1 |
| | | TaqMan ® probe | 11M_Probe | 5'/Dye/GC+C +T+GA A+C+T AA+GT/ Quencher/3' (SEQ ID NO: 374) | 67.8 |
| 12 | 12M (86 bp) | Forward primer | 12M_Primer1 | 5'ACT CAC CAA CTC CTG G3' (SEQ ID NO: 375) | 60 |
| | | Reverse primer | 12M_Primer2 | 5'TTC ATG TAT TG+G TGA AAC G3' (SEQ ID NO: 376) | 60.1 |
| | | TaqMan ® probe | 12M_Probe | 5'/Dye/CAA TGC CGC /Quencher-2/CCC CGT TTG TAG/Quencher-1/3' (SEQ ID NO: 377) | 68 |
| 13 | 13M (78 bp) | Forward primer | 13M_Primer1 | 5'CGG AGT CCC ATA +ATA GC3' (SEQ ID NO: 378) | 59.9 |
| | | Reverse primer | 13M_Primer2 | 5'GTC TGC GGG GTC TAT AG3' (SEQ ID NO: 379) | 60.1 |
| | | TaqMan ® probe | 13M_Probe | 5'/Dye/CA+G +AG+G +C+TC CCA T/Quencher/ 3' (SEQ ID NO: 380) | 68.7 |
| 14 | 14M (84 bp) | Forward primer | 14M_Primer1 | 5'AAA GTT GG+G ATT A+CA TTT3' (SEQ ID NO: 381) | 59.9 |
| | | Reverse primer | 14M_Primer2 | 5'GGC GAG GTC TTT T+AC TG3' (SEQ ID NO: 382) | 60.4 |
| | | TaqMan ® probe | 14M_Probe | 5'/Dye/TGA GAC AAC /Quencher-2/AGA ATC TCC TAG CTC AGA TGA/Quencher-1/3' (SEQ ID NO: 383) | 68 |
| 15 | 15M (86 bp) | Forward primer | 15M_Primer1 | 5'TAGGCCCACTTAACACTAC3' (SEQ ID NO: 384) | 60.6 |
| | | Reverse primer | 15M_Primer2 | 5'GGAGGCCCTTAGACTTAC3' (SEQ ID NO: 385) | 60.5 |

TABLE 20-continued

| Primers and probes for Epstein-Barr virus (EBV) | | | | |
|---|---|---|---|---|
| Set | Amplicon (size) (Assay) | Detail | Named as | Sequence | $T_M{}^1$ |

| | | | | | |
|---|---|---|---|---|---|
| | | TaqMan ® probe | 15M_Probe | 5'/Dye/CGCCTCTCCATTCATCATGTAACCCAC/ Quencher/3' (SEQ ID NO: 386) | 68.4 |
| 16 | 16M (85 bp) | Forward primer | 16M_Primer1 | 5'ATCCCTAGGATAATACCACAC3' (SEQ ID NO: 387) | 60.5 |
| | | Reverse primer | 16M_Primer2 | 5'CACGTAAAGCCACAAGC3' (SEQ ID NO: 388) | 60.8 |
| | | TaqMan ® probe | 16M_Probe | 5'/Dye/AGCAGTGTAGTCCTGTCAATCTCCTGA/ Quencher/3' (SEQ ID NO: 389) | 68.3 |
| 17 | 1N (93 bp) | Forward primer | 1 N_Primer1 | 5'CTC CTA AGA AGG +CAC C3' (SEQ ID NO: 390) | 60.4 |
| | | Reverse primer | 1 N_Primer2 | 5'CTC CTC TTC TTG CTG GA3' (SEQ ID NO: 391) | 60.1 |
| | | TaqMan ® probe | 1 N_Probe | 5'/Dye/CA+A +G+AA C+C+C AG+AC/ Quencher/3' (SEQ ID NO: 392) | 68.9 |
| 18 | 2N (81 bp) | Forward primer | 2N_Primer1 | 5'ATT +AGA GAC C+AC TTT +GAG3' (SEQ ID NO: 393) | 60.1 |
| | | Reverse primer | 2N_Primer2 | 5'TTA GTC +TTC ATC CTC T+TC T3' (SEQ ID NO: 394) | 60.3 |
| | | TaqMan ® probe | 2N_Probe | 5'/Dye/CG+C C+AA T+C+T +G+TCT/ Quencher/3' (SEQ ID NO: 395) | 68.7 |
| 19 | 3N (83 bp) | Forward primer | 3N_Primer1 | 5'TCT AAT TGT TGA CAC +GGA T3' (SEQ ID NO: 396) | 60.3 |
| | | Reverse primer | 3N_Primer2 | 5'TGT CT+G ACA GTT GTT CC3' (SEQ ID NO: 397) | 60.4 |
| | | TaqMan ® probe | 3N_Probe | 5'/Dye/CTT GGA AAC /Quencher-2/CCG TCA CTC TCA GTA ATT CC/Quencher-1/3' (SEQ ID NO: 398) | 68.1 |
| 20 | 4N (84 bp) | Forward primer | 4N_Primer1 | 5'TCA CCT CTT GAT AGG GAT C3' (SEQ ID NO: 399) | 59.8 |
| | | Reverse primer | 4N_Primer2 | 5'ATT AGC CAT CCA AAG C+AT3' (SEQ ID NO: 400) | 60.3 |
| | | TaqMan ® probe | 4N_Probe | 5'/Dye/CGG GCA TGG /Quencher-2/ACC TCT AGC ATC T/Quencher-1/3' (SEQ ID NO: 401) | 67.7 |
| 21 | 5N (89 bp) | Forward primer | 5N_Primer1 | 5'ATA TTG +TAA GA+C A+A+T CAC3' (SEQ ID NO: 402) | 60.3 |
| | | Reverse primer | 5N_Primer2 | 5'ATG TGG CTG GAC CAA3' (SEQ ID NO: 403) | 60.1 |
| | | TaqMan ® probe | 5N_Probe | 5'/Dye/CC+T G+AG +GGG C+TG T/Quencher/3' (SEQ ID NO: 404) | 68.4 |
| 22 | 6N (84 bp) | Forward primer | 6N_Primer1 | 5'CTC TAC GCC CGA CAG3' (SEQ ID NO: 405) | 60.2 |

TABLE 20-continued

| | Amplicon (size) | | | | |
|---|---|---|---|---|---|
| Set | (Assay) | Detail | Named as | Sequence | $T_M{}^1$ |
| | | Reverse primer | 6N_Primer2 | 5'TTG GTG GCA TC+A TGA G3' (SEQ ID NO: 406) | 59.7 |
| | | TaqMan ® probe | 6N_Probe | 5'/Dye/TGT CAC CTC /Quencher-2/TGT CAC AAC CGA GG/Quencher-1/3' (SEQ ID NO: 407) | 67.7 |
| 23 | 7N (98 bp) | Forward primer | 7N_Primer1 | 5'ACC CAC ACC ACT ACT C3' (SEQ ID NO: 408) | 59.6 |
| | | Reverse primer | 7N_Primer2 | 5'TCT GGC ACA TGC AAG +A3' (SEQ ID NO: 409) | 60.4 |
| | | TaqMan ® probe | 7N_Probe | 5'/Dye/TAC CGA ACT /Quencher-2/TCA ACC CAC ACC ATC AC/Quencher-1/3' (SEQ ID NO: 410) | 68.2 |
| 24 | 8N (86 bp) | Forward primer | 8N_Primer1 | 5'AAT CAA TGC ACC CTC +TTA3' (SEQ ID NO: 411) | 59.9 |
| | | Reverse primer | 8N_Primer2 | 5'AAT G+TT ATA AAA TAC AG+T +CG3' (SEQ ID NO: 412) | 60.2 |
| | | TaqMan ® probe | 8N_Probe | 5'/Dye/TGA TCC AGA /Quencher-2/TAG TCC AGA ACC ACG GT/Quencher-1/3' (SEQ ID NO: 413) | 68.4 |
| 25 | 9N (85 bp) | Forward primer | 9N_Primer1 | 5'ATT ACC CCC CTC ACA AT3' (SEQ ID NO: 414) | 59.8 |
| | | Reverse primer | 9N_Primer2 | 5'TAG ATG AT+G TAA TTG TT+G GT3' (SEQ ID NO: 415) | 59.9 |
| | | TaqMan ® probe | 9N_Probe | 5'/Dye/CAC CAC CAG/Quencher-2/CAG CAC CAG C/Quencher-1/3' (SEQ ID NO: 416) | 68.1 |
| 26 | 10N (82 bp) | Forward primer | 10N_Primer 1 | 5'ACA AGC AAC GCA AGC3' (SEQ ID NO: 417) | 60.5 |
| | | Reverse primer | 10N_Primer 2 | 5'AGG ACT GGA C+TT AGT TCA3' (SEQ ID NO: 418) | 60.7 |
| | | TaqMan ® probe | 10N_Probe | 5'/Dye/ACC TTG GAG/Quencher-2/ACC AGA GCC AAA CA/Quencher-1/3' (SEQ ID NO: 419) | 68 |
| 27 | 11N (75 bp) | Forward primer | 11N_Primer 1 | 5'CGT +TTG TAG AAA T+TC ACA C3' (SEQ ID NO: 420) | 60.2 |
| | | Reverse primer | 11N_Primer 2 | 5'TCT GGG CTA TT+A TGG GA3' (SEQ ID NO: 421) | 60.1 |
| | | TaqMan ® probe | 11 N_Probe | 5'/Dye/TCA +C+C+A ATA +C+AT+GA/Quencher/3' (SEQ ID NO: 422) | 68 |
| 28 | 12N (77 bp) | Forward primer | 12N_Primer 1 | 5'CCA TTC TCT TCC CCG AT3' (SEQ ID NO: 423) | 60.3 |
| | | Reverse primer | 12N_Primer 2 | 5'AAA TGT AA+T CCC AA+C TTT3' (SEQ ID NO: 424) | 60.3 |

TABLE 20-continued

| | Primers and probes for Epstein-Barr virus (EBV) | | | |
|---|---|---|---|---|
| Set (Assay) | Amplicon (size) Detail | Named as | Sequence | $T_M^1$ |
| | TaqMan ® probe | 12N_Probe | 5'/Dye/CC+G +C+A+G ACT +TA+GA/ Quencher/3' (SEQ ID NO: 425) | 67.7 |

[1]"Dye" stands for a fluorescent reporter dye. Any reporter dyes such as FAM ™, HEX ™, VIC ®, Cy5 ™, and Cy5.5 ™ that is compatible with the detection channels for the instrument can be used. A quencher compatible with the respective dye was used at 3' end of the probe (Quencher-1).
A second quencher (Quencher-2) such as ZEN was sometimes placed internally between $9^{th}$ and $10^{th}$ nucleotide base from the reporter dye to enhance the overall dye quenching.
[2]These estimates of melting temperature(TM) were calculated using IDT'S oligo analyzer tools with following settings:
(a) For primers:
Target type = DNA,
Oligo concentration = 0.9 µM,
Nat concentration = 50 mM,
$Mg^{++}$ concentration = 3 mM, and
dNTPs concentration = 0.8 mM.
(b) for Probe:
Target type = DNA,
Oligo concentration = 0.25 µM,
Nat concentration = 50 mM,
$Mg^{++}$ concentration = 3 mM, and
dNTPs concentration = 0.8 mM.
[3]+ = Locked nucleic acid

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition for detecting tumor-derived Human Papilloma Virus type 31 (HPV31) in a sample from a subject, comprising at least a triad of modified oligonucleotide primer and probe sets selected from the group consisting of:

Set 1: SEQ ID NO: 134, SEQ ID NO: 135, and SEQ ID NO: 136,

Set 2: SEQ ID NO: 137, SEQ ID NO: 138, and SEQ ID NO: 139,

Set 3: SEQ ID NO: 140, SEQ ID NO: 141, and SEQ ID NO: 142,

Set 4: SEQ ID NO: 143, SEQ ID NO: 144, and SEQ ID NO: 145,

Set 5: SEQ ID NO: 146, SEQ ID NO: 147, and SEQ ID NO: 148,

Set 6: SEQ ID NO: 149, SEQ ID NO: 150, and SEQ ID NO: 151,

Set 7: SEQ ID NO: 152, SEQ ID NO: 153, and SEQ ID NO: 154,

Set 8: SEQ ID NO: 155, SEQ ID NO: 156, and SEQ ID NO: 157,

Set 9: SEQ ID NO: 158, SEQ ID NO: 159, and SEQ ID NO: 160,

Set 10: SEQ ID NO: 161, SEQ ID NO: 162, and SEQ ID NO: 163,

Set 11: SEQ ID NO: 164, SEQ ID NO: 165, and SEQ ID NO: 166,

Set 12: SEQ ID NO: 167, SEQ ID NO: 168, and SEQ ID NO: 169,

Set 13: SEQ ID NO: 170, SEQ ID NO: 171, and SEQ ID NO: 172,

Set 14: SEQ ID NO: 173, SEQ ID NO: 174, and SEQ ID NO: 175,

Set 15: SEQ ID NO: 176, SEQ ID NO: 177, and SEQ ID NO: 178,

Set 16: SEQ ID NO: 179, SEQ ID NO: 180, and SEQ ID NO: 181, and

Set 17: SEQ ID NO: 182, SEQ ID NO: 183, and SEQ ID NO: 184, wherein the first primer and probe set of the triad is configured to produce a first amplicon signal, wherein the second primer and probe set of the triad is configured to produce a second amplicon signal, wherein the third primer and probe set of the triad is configured to produce a third amplicon signal, and wherein the primer and probe set of the triad with the smallest set number corresponds to the first primer and probe set, and the primer and probe set of the triad with the largest set number corresponds to the third primer and probe set.

2. The composition of claim 1, wherein the triad contains three primer and probes sets of which no two primer and probe sets have consecutive set numbers.

3. The composition of claim 1, wherein the triad contains three non-consecutive numbered primer and probe sets.

4. The composition of claim 1, comprising primer and probe sets numbered 4, 7, and 10.

5. A method for detecting tumor-derived Human Papilloma Virus type 31 (HPV31) in a sample from a subject, the method comprising:

providing at least a triad of modified oligonucleotide primer and probe sets comprising the composition of any one of claim 1;

fractionating a plurality of HPV DNA fragments from the sample into droplets at a concentration wherein only 0 or 1 molecule of the DNA fragments is present in each droplet;

amplifying HPV DNA in each droplet with the triad of primer and probe sets to produce amplicon signals;

detecting in each droplet any amplicon signals;

wherein detection within a droplet of the second amplicon, but not the first or third amplicon, indicates that the HPV DNA fragment fractionated into the droplet is a tumor-derived HPV DNA fragment.

* * * * *

SEQUENCE LISTING

<160> NUMBER OF SEQ ID NOS: 425

<210> SEQ ID NO 1
<211> LENGTH: 19
<212> TYPE: DNA
<213> ORGANISM: Artificial Sequence
<220> FEATURE:
<223> OTHER INFORMATION: Synthetic Construct

<400> SEQUENCE: 1
tgactctacg cttcggttg                                                          19

<210> SEQ ID NO 2
<211> LENGTH: 19
<212> TYPE: DNA
<213> ORGANISM: Artificial Sequence
<220> FEATURE:
<223> OTHER INFORMATION: Synthetic Construct

<400> SEQUENCE: 2
gcccattaac aggtcttcc                                                          19

<210> SEQ ID NO 3
<211> LENGTH: 30
<212> TYPE: DNA
<213> ORGANISM: Artificial Sequence
<220> FEATURE:
<223> OTHER INFORMATION: Synthetic Construct

<400> SEQUENCE: 3
cgtacaaagc acacacgtag acattcgtac                                              30

-continued

```
<210> SEQ ID NO 4
<211> LENGTH: 19
<212> TYPE: DNA
<213> ORGANISM: Artificial Sequence
<220> FEATURE:
<223> OTHER INFORMATION: Synthetic Construct

<400> SEQUENCE: 4
ggtttgtaac atcccaggc                                                    19

<210> SEQ ID NO 5
<211> LENGTH: 25
<212> TYPE: DNA
<213> ORGANISM: Artificial Sequence
<220> FEATURE:
<223> OTHER INFORMATION: Synthetic Construct

<400> SEQUENCE: 5
gtgtattttt taaggggatc ttctt                                             25

<210> SEQ ID NO 6
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(7)
<223> OTHER INFORMATION: locked nucleic acid
<220> FEATURE:
<221> NAME/KEY: misc_feature
<222> LOCATION: (9)..(9)
<223> OTHER INFORMATION: locked nucleic acid

<400> SEQUENCE: 6
cacctccagc acc                                                          13

<210> SEQ ID NO 7
<211> LENGTH: 24
<212> TYPE: DNA
<213> ORGANISM: Artificial Sequence
<220> FEATURE:
<223> OTHER INFORMATION: Synthetic Construct

<400> SEQUENCE: 7
atctgtacag catgaagtgc aaga                                              24

<210> SEQ ID NO 8
<211> LENGTH: 19
<212> TYPE: DNA
<213> ORGANISM: Artificial Sequence
<220> FEATURE:
<223> OTHER INFORMATION: Synthetic Construct

<400> SEQUENCE: 8
ctagtgggcg catgtaggc                                                    19

<210> SEQ ID NO 9
<211> LENGTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(4)
<223> OTHER INFORMATION: locked nucleic acid
```

```
<220> FEATURE:
<221> NAME/KEY: misc_feature
<222> LOCATION: (5)..(7)
<223> OTHER INFORMATION: locked nucleic acid

<400> SEQUENCE: 9
tctatgacct g                                                      11

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
tgaagccaga attgagctag                                             20

<210> SEQ ID NO 11
<211> LENGTH: 18
<212> TYPE: DNA
<213> ORGANISM: Artificial Sequence
<220> FEATURE:
<223> OTHER INFORMATION: Synthetic Construct

<400> SEQUENCE: 11
aggacagggt gttcagaa                                               18

<210> SEQ ID NO 12
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (5)..(6)
<223> OTHER INFORMATION: locked nucleic acid
<220> FEATURE:
<221> NAME/KEY: misc_feature
<222> LOCATION: (9)..(9)
<223> OTHER INFORMATION: locked nucleic acid

<400> SEQUENCE: 12
cagacgacct tcg                                                    13

<210> SEQ ID NO 13
<211> LENGTH: 21
<212> TYPE: DNA
<213> ORGANISM: Artificial Sequence
<220> FEATURE:
<223> OTHER INFORMATION: Synthetic Construct

<400> SEQUENCE: 13
agcacacaag tagatattcg c                                           21

<210> SEQ ID NO 14
<211> LENGTH: 19
<212> TYPE: DNA
<213> ORGANISM: Artificial Sequence
<220> FEATURE:
<223> OTHER INFORMATION: Synthetic Construct

<400> SEQUENCE: 14
```

```
tagtagaaca gttggggca                                           19

<210> SEQ ID NO 15
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: locked nucleic acid
<220> FEATURE:
<221> NAME/KEY: misc_feature
<222> LOCATION: (7)..(7)
<223> OTHER INFORMATION: locked nucleic acid
<220> FEATURE:
<221> NAME/KEY: misc_feature
<222> LOCATION: (9)..(10)
<223> OTHER INFORMATION: locked nucleic acid
<220> FEATURE:
<221> NAME/KEY: misc_feature
<222> LOCATION: (13)..(13)
<223> OTHER INFORMATION: locked nucleic acid

<400> SEQUENCE: 15
taacagctct tgc                                                 13

<210> SEQ ID NO 16
<211> LENGTH: 22
<212> TYPE: DNA
<213> ORGANISM: Artificial Sequence
<220> FEATURE:
<223> OTHER INFORMATION: Synthetic Construct

<400> SEQUENCE: 16
taacaccaca gttcgtttat gt                                       22

<210> SEQ ID NO 17
<211> LENGTH: 21
<212> TYPE: DNA
<213> ORGANISM: Artificial Sequence
<220> FEATURE:
<223> OTHER INFORMATION: Synthetic Construct

<400> SEQUENCE: 17
acaatattca ctgtgcccat a                                        21

<210> SEQ ID NO 18
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (5)..(6)
<223> OTHER INFORMATION: locked nucleic acid
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (10)..(11)
<223> OTHER INFORMATION: locked nucleic acid

<400> SEQUENCE: 18
```

-continued tgacctacga acc                                                        13

<210> SEQ ID NO 19
<211> LENGTH: 17
<212> TYPE: DNA
<213> ORGANISM: Artificial Sequence
<220> FEATURE:
<223> OTHER INFORMATION: Synthetic Construct

<400> SEQUENCE: 19
tgaggcgaca ctacgtc                                                    17

<210> SEQ ID NO 20
<211> LENGTH: 23
<212> TYPE: DNA
<213> ORGANISM: Artificial Sequence
<220> FEATURE:
<223> OTHER INFORMATION: Synthetic Construct

<400> SEQUENCE: 20
gtgcccatta ataaatcttc caa                                             23

<210> SEQ ID NO 21
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (5)..(6)
<223> OTHER INFORMATION: locked nucleic acid
<220> FEATURE:
<221> NAME/KEY: misc_feature
<222> LOCATION: (9)..(10)
<223> OTHER INFORMATION: locked nucleic acid

<400> SEQUENCE: 21
agagcacaca cat                                                        13

<210> SEQ ID NO 22
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (5)..(7)
<223> OTHER INFORMATION: locked nucleic acid
<220> FEATURE:
<221> NAME/KEY: misc_feature
<222> LOCATION: (9)..(10)
<223> OTHER INFORMATION: locked nucleic acid

<400> SEQUENCE: 22
cacacgtaga cat                                                        13

<210> SEQ ID NO 23
<211> LENGTH: 17
<212> TYPE: DNA

```
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (15)..(15)
<223> OTHER INFORMATION: locked nucleic acid

<400> SEQUENCE: 23
tgcaccaaaa gagaact                                                                17

<210> SEQ ID NO 24
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(16)
<223> OTHER INFORMATION: locked nucleic acid

<400> SEQUENCE: 24
gtgcataact gtggtaact                                                              19

<210> SEQ ID NO 25
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: locked nucleic acid
<220> FEATURE:
<221> NAME/KEY: misc_feature
<222> LOCATION: (6)..(6)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid
<220> FEATURE:
<221> NAME/KEY: misc_feature
<222> LOCATION: (12)..(12)
<223> OTHER INFORMATION: locked nucleic acid

<400> SEQUENCE: 25
ctgtgggtcc tga                                                                    13

<210> SEQ ID NO 26
<211> LENGTH: 21
<212> TYPE: DNA
<213> ORGANISM: Artificial Sequence
<220> FEATURE:
<223> OTHER INFORMATION: Synthetic Construct

<400> SEQUENCE: 26
agagctgcaa acaactatac a                                                           21

<210> SEQ ID NO 27
<211> LENGTH: 18
<212> TYPE: DNA
<213> ORGANISM: Artificial Sequence
<220> FEATURE:
<223> OTHER INFORMATION: Synthetic Construct

<400> SEQUENCE: 27
tatacctcac gtcgcagt                                                               18
```

```
<210> SEQ ID NO 28
<211> LENGTH: 27
<212> TYPE: DNA
<213> ORGANISM: Artificial Sequence
<220> FEATURE:
<223> OTHER INFORMATION: Synthetic Construct

<400> SEQUENCE: 28
agaatgtgtg tactgcaagc aacagtt                                           27

<210> SEQ ID NO 29
<211> LENGTH: 22
<212> TYPE: DNA
<213> ORGANISM: Artificial Sequence
<220> FEATURE:
<223> OTHER INFORMATION: Synthetic Construct

<400> SEQUENCE: 29
cgtgaggtat atgactttgc tt                                                22

<210> SEQ ID NO 30
<211> LENGTH: 22
<212> TYPE: DNA
<213> ORGANISM: Artificial Sequence
<220> FEATURE:
<223> OTHER INFORMATION: Synthetic Construct

<400> SEQUENCE: 30
tcacatacag catatggatt cc                                                22

<210> SEQ ID NO 31
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: locked nucleic acid
<220> FEATURE:
<221> NAME/KEY: misc_feature
<222> LOCATION: (7)..(7)
<223> OTHER INFORMATION: locked nucleic acid
<220> FEATURE:
<221> NAME/KEY: misc_feature
<222> LOCATION: (10)..(12)
<223> OTHER INFORMATION: locked nucleic acid

<400> SEQUENCE: 31
cgggatttat gca                                                          13

<210> SEQ ID NO 32
<211> LENGTH: 24
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (22)..(23)
<223> OTHER INFORMATION: locked nucleic acid

<400> SEQUENCE: 32
gttttattct aaaattagtg agta                                              24

<210> SEQ ID NO 33
```

```
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(16)
<223> OTHER INFORMATION: locked nucleic acid

<400> SEQUENCE: 33
ttgtattgct gttctaatgt t                                               21

<210> SEQ ID NO 34
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(7)
<223> OTHER INFORMATION: locked nucleic acid
<220> FEATURE:
<221> NAME/KEY: misc_feature
<222> LOCATION: (9)..(11)
<223> OTHER INFORMATION: locked nucleic acid

<400> SEQUENCE: 34
agtttgtatg ga                                                        12

<210> SEQ ID NO 35
<211> LENGTH: 20
<212> TYPE: DNA
<213> ORGANISM: Artificial Sequence
<220> FEATURE:
<223> OTHER INFORMATION: Synthetic Construct

<400> SEQUENCE: 35
caaaccgttg tgtgatttgt                                                20

<210> SEQ ID NO 36
<211> LENGTH: 22
<212> TYPE: DNA
<213> ORGANISM: Artificial Sequence
<220> FEATURE:
<223> OTHER INFORMATION: Synthetic Construct

<400> SEQUENCE: 36
gatgtctttg cttttcttca gg                                             22

<210> SEQ ID NO 37
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(7)
<223> OTHER INFORMATION: locked nucleic acid
<220> FEATURE:
<221> NAME/KEY: misc_feature
<222> LOCATION: (10)..(11)
<223> OTHER INFORMATION: locked nucleic acid

<400> SEQUENCE: 37
aagccactgt gt                                                        12
```

-continued

```
<210> SEQ ID NO 38
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (17)..(17)
<223> OTHER INFORMATION: locked nucleic acid

<400> SEQUENCE: 38
tctggacaaa aagcaaag                                                 18

<210> SEQ ID NO 39
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid

<400> SEQUENCE: 39
gatgatctgc aacaagac                                                 18

<210> SEQ ID NO 40
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: locked nucleic acid
<220> FEATURE:
<221> NAME/KEY: misc_feature
<222> LOCATION: (8)..(9)
<223> OTHER INFORMATION: locked nucleic acid

<400> SEQUENCE: 40
tccaccgacc cct                                                      13

<210> SEQ ID NO 41
<211> LENGTH: 25
<212> TYPE: DNA
<213> ORGANISM: Artificial Sequence
<220> FEATURE:
<223> OTHER INFORMATION: Synthetic Construct

<400> SEQUENCE: 41
tgcatgaata tatgttagat ttgca                                         25

<210> SEQ ID NO 42
<211> LENGTH: 22
<212> TYPE: DNA
<213> ORGANISM: Artificial Sequence
<220> FEATURE:
<223> OTHER INFORMATION: Synthetic Construct

<400> SEQUENCE: 42
tcctctgagc tgtcatttaa tt                                            22

<210> SEQ ID NO 43
<211> LENGTH: 13
<212> TYPE: DNA
```

```
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: locked nucleic acid
<220> FEATURE:
<221> NAME/KEY: misc_feature
<222> LOCATION: (5)..(7)
<223> OTHER INFORMATION: locked nucleic acid
<220> FEATURE:
<221> NAME/KEY: misc_feature
<222> LOCATION: (12)..(12)
<223> OTHER INFORMATION: locked nucleic acid

<400> SEQUENCE: 43
acaactgatc tct                                                          13

<210> SEQ ID NO 44
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: locked nucleic acid

<400> SEQUENCE: 44
tgaaatagat ggtccagc                                                     18

<210> SEQ ID NO 45
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (18)..(18)
<223> OTHER INFORMATION: locked nucleic acid

<400> SEQUENCE: 45
tgcaacaaaa ggttacaata                                                   20

<210> SEQ ID NO 46
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: locked nucleic acid
<220> FEATURE:
<221> NAME/KEY: misc_feature
<222> LOCATION: (8)..(9)
<223> OTHER INFORMATION: locked nucleic acid
<220> FEATURE:
<221> NAME/KEY: misc_feature
<222> LOCATION: (11)..(12)
<223> OTHER INFORMATION: locked nucleic acid

<400> SEQUENCE: 46
cagagcccat tac                                                          13

<210> SEQ ID NO 47
<211> LENGTH: 19
```

-continued

```
<212> TYPE: DNA
<213> ORGANISM: Artificial Sequence
<220> FEATURE:
<223> OTHER INFORMATION: Synthetic Construct

<400> SEQUENCE: 47
tgactctacg cttcggttg                                                    19

<210> SEQ ID NO 48
<211> LENGTH: 19
<212> TYPE: DNA
<213> ORGANISM: Artificial Sequence
<220> FEATURE:
<223> OTHER INFORMATION: Synthetic Construct

<400> SEQUENCE: 48
gcccattaac aggtcttcc                                                    19

<210> SEQ ID NO 49
<211> LENGTH: 30
<212> TYPE: DNA
<213> ORGANISM: Artificial Sequence
<220> FEATURE:
<223> OTHER INFORMATION: Synthetic Construct

<400> SEQUENCE: 49
tacaaagcac acacgtagac attcgtactt                                        30

<210> SEQ ID NO 50
<211> LENGTH: 30
<212> TYPE: DNA
<213> ORGANISM: Artificial Sequence
<220> FEATURE:
<223> OTHER INFORMATION: Synthetic Construct

<400> SEQUENCE: 50
cgtacaaagc acacacgtag acattcgtac                                        30

<210> SEQ ID NO 51
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (5)..(7)
<223> OTHER INFORMATION: locked nucleic acid
<220> FEATURE:
<221> NAME/KEY: misc_feature
<222> LOCATION: (9)..(10)
<223> OTHER INFORMATION: locked nucleic acid

<400> SEQUENCE: 51
cacacgtaga cat                                                          13

<210> SEQ ID NO 52
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (11)..(11)
```

-continued

```
<223> OTHER INFORMATION: locked nucleic acid
<220> FEATURE:
<221> NAME/KEY: misc_feature
<222> LOCATION: (17)..(17)
<223> OTHER INFORMATION: locked nucleic acid

<400> SEQUENCE: 52
actgcaatgt ttcagga                                                 17

<210> SEQ ID NO 53
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: locked nucleic acid
<220> FEATURE:
<221> NAME/KEY: misc_feature
<222> LOCATION: (7)..(7)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid
<220> FEATURE:
<221> NAME/KEY: misc_feature
<222> LOCATION: (16)..(16)
<223> OTHER INFORMATION: locked nucleic acid

<400> SEQUENCE: 53
catgtatagt tgtttgc                                                 17

<210> SEQ ID NO 54
<211> LENGTH: 28
<212> TYPE: DNA
<213> ORGANISM: Artificial Sequence
<220> FEATURE:
<223> OTHER INFORMATION: Synthetic Construct

<400> SEQUENCE: 54
cgacccagaa agttaccaca gttatgca                                     28

<210> SEQ ID NO 55
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (19)..(19)
<223> OTHER INFORMATION: locked nucleic acid

<400> SEQUENCE: 55
ttagaatgtg tgtactgcaa                                              20

<210> SEQ ID NO 56
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (10)..(10)
<223> OTHER INFORMATION: locked nucleic acid

<400> SEQUENCE: 56
```

-continued cataaatccc gaaaagca                                                          18

<210> SEQ ID NO 57
<211> LENGTH: 26
<212> TYPE: DNA
<213> ORGANISM: Artificial Sequence
<220> FEATURE:
<223> OTHER INFORMATION: Synthetic Construct

<400> SEQUENCE: 57
gcaacagtta ctgcgacgtg aggtat                                                 26

<210> SEQ ID NO 58
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (11)..(11)
<223> OTHER INFORMATION: locked nucleic acid
<220> FEATURE:
<221> NAME/KEY: misc_feature
<222> LOCATION: (15)..(15)
<223> OTHER INFORMATION: locked nucleic acid

<400> SEQUENCE: 58
catagtatat agagatggga                                                        20

<210> SEQ ID NO 59
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (11)..(11)
<223> OTHER INFORMATION: locked nucleic acid
<220> FEATURE:
<221> NAME/KEY: misc_feature
<222> LOCATION: (18)..(18)
<223> OTHER INFORMATION: locked nucleic acid

<400> SEQUENCE: 59
tctatactca ctaattttag                                                        20

<210> SEQ ID NO 60
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: locked nucleic acid
<220> FEATURE:

```
<221> NAME/KEY: misc_feature
<222> LOCATION: (5)..(6)
<223> OTHER INFORMATION: locked nucleic acid
<220> FEATURE:
<221> NAME/KEY: misc_feature
<222> LOCATION: (9)..(10)
<223> OTHER INFORMATION: locked nucleic acid

<400> SEQUENCE: 60
atcacataca gc                                                      12

<210> SEQ ID NO 61
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (14)..(15)
<223> OTHER INFORMATION: locked nucleic acid
<220> FEATURE:
<221> NAME/KEY: misc_feature
<222> LOCATION: (17)..(18)
<223> OTHER INFORMATION: locked nucleic acid

<400> SEQUENCE: 61
cattattgtt atagtttgta                                              20

<210> SEQ ID NO 62
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (17)..(17)
<223> OTHER INFORMATION: locked nucleic acid

<400> SEQUENCE: 62
taattaacaa atcacacaac g                                            21

<210> SEQ ID NO 63
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(6)
<223> OTHER INFORMATION: locked nucleic acid
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (11)..(11)
<223> OTHER INFORMATION: locked nucleic acid

<400> SEQUENCE: 63
tatggaacaa cat                                                     13

<210> SEQ ID NO 64
<211> LENGTH: 18
<212> TYPE: DNA
<213> ORGANISM: Artificial Sequence
<220> FEATURE:
<223> OTHER INFORMATION: Synthetic Construct
```

-continued

```
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (9)..(9)
<223> OTHER INFORMATION: locked nucleic acid
<220> FEATURE:
<221> NAME/KEY: misc_feature
<222> LOCATION: (11)..(11)
<223> OTHER INFORMATION: locked nucleic acid
<220> FEATURE:
<221> NAME/KEY: misc_feature
<222> LOCATION: (14)..(14)
<223> OTHER INFORMATION: locked nucleic acid

<400> SEQUENCE: 64
tgtattaact gtcaaaag                                              18

<210> SEQ ID NO 65
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: locked nucleic acid
<220> FEATURE:
<221> NAME/KEY: misc_feature
<222> LOCATION: (16)..(16)
<223> OTHER INFORMATION: locked nucleic acid

<400> SEQUENCE: 65
ggaatctttg ctttttgt                                              18

<210> SEQ ID NO 66
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: locked nucleic acid
<220> FEATURE:
<221> NAME/KEY: misc_feature
<222> LOCATION: (9)..(10)
<223> OTHER INFORMATION: locked nucleic acid
<220> FEATURE:
<221> NAME/KEY: misc_feature
<222> LOCATION: (12)..(12)
<223> OTHER INFORMATION: locked nucleic acid

<400> SEQUENCE: 66
tgtgtcctga aga                                                  13

<210> SEQ ID NO 67
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (17)..(17)
<223> OTHER INFORMATION: locked nucleic acid

<400> SEQUENCE: 67
```

```
ataatataag gggtcggtg                                                    19

<210> SEQ ID NO 68
<211> LENGTH: 17
<212> TYPE: DNA
<213> ORGANISM: Artificial Sequence
<220> FEATURE:
<223> OTHER INFORMATION: Synthetic Construct

<400> SEQUENCE: 68
agctgggttt ctctacg                                                      17

<210> SEQ ID NO 69
<211> LENGTH: 30
<212> TYPE: DNA
<213> ORGANISM: Artificial Sequence
<220> FEATURE:
<223> OTHER INFORMATION: Synthetic Construct

<400> SEQUENCE: 69
cggtcgatgt atgtcttgtt gcagatcatc                                        30

<210> SEQ ID NO 70
<211> LENGTH: 27
<212> TYPE: DNA
<213> ORGANISM: Artificial Sequence
<220> FEATURE:
<223> OTHER INFORMATION: Synthetic Construct

<400> SEQUENCE: 70
ccggtcgatg tatgtcttgt tgcagat                                           27

<210> SEQ ID NO 71
<211> LENGTH: 17
<212> TYPE: DNA
<213> ORGANISM: Artificial Sequence
<220> FEATURE:
<223> OTHER INFORMATION: Synthetic Construct

<400> SEQUENCE: 71
tgcatggaga tacacct                                                      17

<210> SEQ ID NO 72
<211> LENGTH: 18
<212> TYPE: DNA
<213> ORGANISM: Artificial Sequence
<220> FEATURE:
<223> OTHER INFORMATION: Synthetic Construct

<400> SEQUENCE: 72
acagtagaga tcagttgt                                                     18

<210> SEQ ID NO 73
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (5)..(6)
<223> OTHER INFORMATION: locked nucleic acid
<220> FEATURE:
<221> NAME/KEY: misc_feature
```

-continued

```
<222> LOCATION: (8)..(9)
<223> OTHER INFORMATION: locked nucleic acid
<220> FEATURE:
<221> NAME/KEY: misc_feature
<222> LOCATION: (11)..(11)
<223> OTHER INFORMATION: locked nucleic acid

<400> SEQUENCE: 73
ccagagacaa ct                                              12

<210> SEQ ID NO 74
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (14)..(15)
<223> OTHER INFORMATION: locked nucleic acid
<220> FEATURE:
<221> NAME/KEY: misc_feature
<222> LOCATION: (17)..(17)
<223> OTHER INFORMATION: locked nucleic acid

<400> SEQUENCE: 74
tatgagcaat taaatgaca                                       19

<210> SEQ ID NO 75
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: locked nucleic acid

<400> SEQUENCE: 75
attgtaatgg gctctgtc                                        18

<210> SEQ ID NO 76
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(6)
<223> OTHER INFORMATION: locked nucleic acid
<220> FEATURE:
<221> NAME/KEY: misc_feature
<222> LOCATION: (9)..(12)
<223> OTHER INFORMATION: locked nucleic acid

<400> SEQUENCE: 76
atttcatcct cct                                             13

<210> SEQ ID NO 77
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: locked nucleic acid
```

-continued

<400> SEQUENCE: 77
tacaaagcac acacgtag                                                                18

<210> SEQ ID NO 78
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid

<400> SEQUENCE: 78
ttatggtttc tgagaacaga t                                                            21

<210> SEQ ID NO 79
<211> LENGTH: 25
<212> TYPE: DNA
<213> ORGANISM: Artificial Sequence
<220> FEATURE:
<223> OTHER INFORMATION: Synthetic Construct

<400> SEQUENCE: 79
tggaagacct gttaatgggc acact                                                        25

<210> SEQ ID NO 80
<211> LENGTH: 17
<212> TYPE: DNA
<213> ORGANISM: Artificial Sequence
<220> FEATURE:
<223> OTHER INFORMATION: Synthetic Construct

<400> SEQUENCE: 80
cgctttgagg atccaac                                                                 17

<210> SEQ ID NO 81
<211> LENGTH: 18
<212> TYPE: DNA
<213> ORGANISM: Artificial Sequence
<220> FEATURE:
<223> OTHER INFORMATION: Synthetic Construct

<400> SEQUENCE: 81
gcagtgaagt gttcagtt                                                                18

<210> SEQ ID NO 82
<211> LENGTH: 25
<212> TYPE: DNA
<213> ORGANISM: Artificial Sequence
<220> FEATURE:
<223> OTHER INFORMATION: Synthetic Construct

<400> SEQUENCE: 82
accctacaag ctacctgatc tgtgc                                                        25

<210> SEQ ID NO 83
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: locked nucleic acid -continued

```
<220> FEATURE:
<221> NAME/KEY: misc_feature
<222> LOCATION: (19)..(19)
<223> OTHER INFORMATION: locked nucleic acid

<400> SEQUENCE: 83
aagacataga ataaacctgt                                                20

<210> SEQ ID NO 84
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(8)
<223> OTHER INFORMATION: locked nucleic acid

<400> SEQUENCE: 84
ttaaatgcaa attcaaat                                                  18

<210> SEQ ID NO 85
<211> LENGTH: 29
<212> TYPE: DNA
<213> ORGANISM: Artificial Sequence
<220> FEATURE:
<223> OTHER INFORMATION: Synthetic Construct

<400> SEQUENCE: 85
tgcaagacag tattggaact tacagaggt                                      29

<210> SEQ ID NO 86
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: locked nucleic acid

<400> SEQUENCE: 86
ttatttgtgg tgtatagaga                                                20

<210> SEQ ID NO 87
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (7)..(7)
<223> OTHER INFORMATION: locked nucleic acid
<220> FEATURE:
<221> NAME/KEY: misc_feature
<222> LOCATION: (13)..(13)
<223> OTHER INFORMATION: locked nucleic acid

<400> SEQUENCE: 87
aattctctaa ttctagaata a                                              21

<210> SEQ ID NO 88
```

-continued

```
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (5)..(8)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid

<400> SEQUENCE: 88
catgcggtat act                                                         13

<210> SEQ ID NO 89
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid
<220> FEATURE:
<221> NAME/KEY: misc_feature
<222> LOCATION: (17)..(17)
<223> OTHER INFORMATION: locked nucleic acid

<400> SEQUENCE: 89
aagacattat tcagactct                                                   19

<210> SEQ ID NO 90
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (10)..(10)
<223> OTHER INFORMATION: locked nucleic acid
<220> FEATURE:
<221> NAME/KEY: misc_feature
<222> LOCATION: (16)..(17)
<223> OTHER INFORMATION: locked nucleic acid

<400> SEQUENCE: 90
aataaattgt ataaccca                                                    18

<210> SEQ ID NO 91
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: locked nucleic acid
<220> FEATURE:
<221> NAME/KEY: misc_feature
```

```
<222> LOCATION: (7)..(10)
<223> OTHER INFORMATION: locked nucleic acid

<400> SEQUENCE: 91
tggagacaca tt                                          12

<210> SEQ ID NO 92
<211> LENGTH: 18
<212> TYPE: DNA
<213> ORGANISM: Artificial Sequence
<220> FEATURE:
<223> OTHER INFORMATION: Synthetic Construct

<400> SEQUENCE: 92
agaaaccgtt gaatccag                                    18

<210> SEQ ID NO 93
<211> LENGTH: 19
<212> TYPE: DNA
<213> ORGANISM: Artificial Sequence
<220> FEATURE:
<223> OTHER INFORMATION: Synthetic Construct

<400> SEQUENCE: 93
atttcacaac atagctggg                                   19

<210> SEQ ID NO 94
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (6)..(8)
<223> OTHER INFORMATION: locked nucleic acid
<220> FEATURE:
<221> NAME/KEY: misc_feature
<222> LOCATION: (11)..(12)
<223> OTHER INFORMATION: locked nucleic acid

<400> SEQUENCE: 94
agacacctta atga                                        14

<210> SEQ ID NO 95
<211> LENGTH: 16
<212> TYPE: DNA
<213> ORGANISM: Artificial Sequence
<220> FEATURE:
<223> OTHER INFORMATION: Synthetic Construct

<400> SEQUENCE: 95
ccagtgccat tcgtgc                                      16

<210> SEQ ID NO 96
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: locked nucleic acid
<220> FEATURE:
```

```
<221> NAME/KEY: misc_feature
<222> LOCATION: (10)..(10)
<223> OTHER INFORMATION: locked nucleic acid

<400> SEQUENCE: 96
ttatacttgt gtttctctg                                              19

<210> SEQ ID NO 97
<211> LENGTH: 24
<212> TYPE: DNA
<213> ORGANISM: Artificial Sequence
<220> FEATURE:
<223> OTHER INFORMATION: Synthetic Construct

<400> SEQUENCE: 97
cacgacagga acgactccaa cgac                                        24

<210> SEQ ID NO 98
<211> LENGTH: 17
<212> TYPE: DNA
<213> ORGANISM: Artificial Sequence
<220> FEATURE:
<223> OTHER INFORMATION: Synthetic Construct

<400> SEQUENCE: 98
atggacctaa ggcaaca                                                17

<210> SEQ ID NO 99
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid

<400> SEQUENCE: 99
tgacatagaa ggtcaacc                                               18

<210> SEQ ID NO 100
<211> LENGTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (5)..(8)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid

<400> SEQUENCE: 100
tttagagccc c                                                      11

<210> SEQ ID NO 101
<211> LENGTH: 18
<212> TYPE: DNA
<213> ORGANISM: Artificial Sequence
<220> FEATURE:
<223> OTHER INFORMATION: Synthetic Construct
```

-continued

```
<220> FEATURE:
<221> NAME/KEY: misc_feature
<222> LOCATION: (8)..(8)
<223> OTHER INFORMATION: locked nucleic acid

<400> SEQUENCE: 101
cgagcaatta agcgactc                                              18

<210> SEQ ID NO 102
<211> LENGTH: 18
<212> TYPE: DNA
<213> ORGANISM: Artificial Sequence
<220> FEATURE:
<223> OTHER INFORMATION: Synthetic Construct

<400> SEQUENCE: 102
cgggctggta aatgttga                                             18

<210> SEQ ID NO 103
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(4)
<223> OTHER INFORMATION: locked nucleic acid
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (11)..(12)
<223> OTHER INFORMATION: locked nucleic acid

<400> SEQUENCE: 103
tcgttttctt cct                                                  13

<210> SEQ ID NO 104
<211> LENGTH: 18
<212> TYPE: DNA
<213> ORGANISM: Artificial Sequence
<220> FEATURE:
<223> OTHER INFORMATION: Synthetic Construct

<400> SEQUENCE: 104
acaacgtcac acaatgtt                                             18

<210> SEQ ID NO 105
<211> LENGTH: 18
<212> TYPE: DNA
<213> ORGANISM: Artificial Sequence
<220> FEATURE:
<223> OTHER INFORMATION: Synthetic Construct

<400> SEQUENCE: 105
tctgctgagc tttctact                                             18

<210> SEQ ID NO 106
<211> LENGTH: 29
<212> TYPE: DNA
<213> ORGANISM: Artificial Sequence
<220> FEATURE:
<223> OTHER INFORMATION: Synthetic Construct

<400> SEQUENCE: 106
```

-continued tgtatgtgtt gtaagtgtga agccagaat                                                    29

<210> SEQ ID NO 107
<211> LENGTH: 16
<212> TYPE: DNA
<213> ORGANISM: Artificial Sequence
<220> FEATURE:
<223> OTHER INFORMATION: Synthetic Construct

<400> SEQUENCE: 107
accttcgagc attcca                                                                  16

<210> SEQ ID NO 108
<211> LENGTH: 16
<212> TYPE: DNA
<213> ORGANISM: Artificial Sequence
<220> FEATURE:
<223> OTHER INFORMATION: Synthetic Construct

<400> SEQUENCE: 108
ttactgctgg gatgca                                                                  16

<210> SEQ ID NO 109
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(7)
<223> OTHER INFORMATION: locked nucleic acid
<220> FEATURE:
<221> NAME/KEY: misc_feature
<222> LOCATION: (9)..(9)
<223> OTHER INFORMATION: locked nucleic acid
<220> FEATURE:
<221> NAME/KEY: misc_feature
<222> LOCATION: (11)..(12)
<223> OTHER INFORMATION: locked nucleic acid

<400> SEQUENCE: 109
ctgaacaccc tgt                                                                     13

<210> SEQ ID NO 110
<211> LENGTH: 18
<212> TYPE: DNA
<213> ORGANISM: Artificial Sequence
<220> FEATURE:
<223> OTHER INFORMATION: Synthetic Construct

<400> SEQUENCE: 110
ccctacaagc tacctgat                                                                18

<210> SEQ ID NO 111
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid
<220> FEATURE:
<221> NAME/KEY: misc_feature -continued

```
<222> LOCATION: (13)..(13)
<223> OTHER INFORMATION: locked nucleic acid
<220> FEATURE:
<221> NAME/KEY: misc_feature
<222> LOCATION: (15)..(15)
<223> OTHER INFORMATION: locked nucleic acid

<400> SEQUENCE: 111
caatatacac aggttattt                                                  19

<210> SEQ ID NO 112
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(5)
<223> OTHER INFORMATION: locked nucleic acid
<220> FEATURE:
<221> NAME/KEY: misc_feature
<222> LOCATION: (8)..(9)
<223> OTHER INFORMATION: locked nucleic acid

<400> SEQUENCE: 112
cacggaactg aac                                                        13

<210> SEQ ID NO 113
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(7)
<223> OTHER INFORMATION: locked nucleic acid
<220> FEATURE:
<221> NAME/KEY: misc_feature
<222> LOCATION: (12)..(13)
<223> OTHER INFORMATION: locked nucleic acid
<220> FEATURE:
<221> NAME/KEY: misc_feature
<222> LOCATION: (16)..(16)
<223> OTHER INFORMATION: locked nucleic acid

<400> SEQUENCE: 113
tatttgaatt tgcattta                                                   18

<210> SEQ ID NO 114
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: locked nucleic acid
<220> FEATURE:
<221> NAME/KEY: misc_feature
<222> LOCATION: (9)..(10)
<223> OTHER INFORMATION: locked nucleic acid
<220> FEATURE:
<221> NAME/KEY: misc_feature
<222> LOCATION: (16)..(6)
<223> OTHER INFORMATION: locked nucleic acid

<400> SEQUENCE: 114
aatctataca tttatggc                                                   18
```

-continued

```
<210> SEQ ID NO 115
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (7)..(7)
<223> OTHER INFORMATION: locked nucleic acid
<220> FEATURE:
<221> NAME/KEY: misc_feature
<222> LOCATION: (9)..(9)
<223> OTHER INFORMATION: locked nucleic acid
<220> FEATURE:
<221> NAME/KEY: misc_feature
<222> LOCATION: (12)..(12)
<223> OTHER INFORMATION: locked nucleic acid

<400> SEQUENCE: 115
agacagtata ccgc                                                    14

<210> SEQ ID NO 116
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: locked nucleic acid
<220> FEATURE:
<221> NAME/KEY: misc_feature
<222> LOCATION: (10)..(12)
<223> OTHER INFORMATION: locked nucleic acid
<220> FEATURE:
<221> NAME/KEY: misc_feature
<222> LOCATION: (17)..(17)
<223> OTHER INFORMATION: locked nucleic acid

<400> SEQUENCE: 116
ctagaattag agaattaaga                                              20

<210> SEQ ID NO 117
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(16)
<223> OTHER INFORMATION: locked nucleic acid

<400> SEQUENCE: 117
agtgttagtt agtttttcca at                                           22

<210> SEQ ID NO 118
<211> LENGTH: 13
<212> TYPE: DNA
<213> ORGANISM: Artificial Sequence
<220> FEATURE:
<223> OTHER INFORMATION: Synthetic Construct
```

-continued

```
<220> FEATURE:
<221> NAME/KEY: misc_feature
<222> LOCATION: (3)..(6)
<223> OTHER INFORMATION: locked nucleic acid
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (11)..(11)
<223> OTHER INFORMATION: locked nucleic acid

<400> SEQUENCE: 118
tcagactctg tgt                                                    13

<210> SEQ ID NO 119
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (15)..(15)
<223> OTHER INFORMATION: locked nucleic acid

<400> SEQUENCE: 119
attaataagg tgcctgc                                                17

<210> SEQ ID NO 120
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (14)..(14)
<223> OTHER INFORMATION: locked nucleic acid

<400> SEQUENCE: 120
tcgtttttca ttaaggtgt                                              19

<210> SEQ ID NO 121
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(8)
<223> OTHER INFORMATION: locked nucleic acid
<220> FEATURE:
<221> NAME/KEY: misc_feature
<222> LOCATION: (11)..(12)
<223> OTHER INFORMATION: locked nucleic acid

<400> SEQUENCE: 121
tgaatccagc aga                                                    13

<210> SEQ ID NO 122
<211> LENGTH: 19
<212> TYPE: DNA
<213> ORGANISM: Artificial Sequence
<220> FEATURE:
```

-continued

<223> OTHER INFORMATION: Synthetic Construct

<400> SEQUENCE: 122
atttcacaac atagctggg                                              19

<210> SEQ ID NO 123
<211> LENGTH: 17
<212> TYPE: DNA
<213> ORGANISM: Artificial Sequence
<220> FEATURE:
<223> OTHER INFORMATION: Synthetic Construct

<400> SEQUENCE: 123
gtttctctgc gtcgttg                                                17

<210> SEQ ID NO 124
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (5)..(8)
<223> OTHER INFORMATION: locked nucleic acid
<220> FEATURE:
<221> NAME/KEY: misc_feature
<222> LOCATION: (11)..(11)
<223> OTHER INFORMATION: locked nucleic acid

<400> SEQUENCE: 124
agtgccattc gtg                                                    13

<210> SEQ ID NO 125
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: locked nucleic acid

<400> SEQUENCE: 125
attgtattgc atttagagcc                                             20

<210> SEQ ID NO 126
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(16)
<223> OTHER INFORMATION: locked nucleic acid

<400> SEQUENCE: 126
ttcatcgttt tcttcctc                                               18

<210> SEQ ID NO 127
<211> LENGTH: 13
<212> TYPE: DNA
<213> ORGANISM: Artificial Sequence

```
<220> FEATURE:
<223> OTHER INFORMATION: Synthetic Construct
<220> FEATURE:
<221> NAME/KEY: misc_feature
<222> LOCATION: (7)..(9)
<223> OTHER INFORMATION: locked nucleic acid
<220> FEATURE:
<221> NAME/KEY: misc_feature
<222> LOCATION: (9)..(11)
<223> OTHER INFORMATION: locked nucleic acid

<400> SEQUENCE: 127
ctatgtcacg agc                                                      13

<210> SEQ ID NO 128
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (14)..(14)
<223> OTHER INFORMATION: locked nucleic acid

<400> SEQUENCE: 128
atagatggag ttaatcatca                                               20

<210> SEQ ID NO 129
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (13)..(13)
<223> OTHER INFORMATION: locked nucleic acid

<400> SEQUENCE: 129
acttacaaca catacaca                                                 18

<210> SEQ ID NO 130
<211> LENGTH: 25
<212> TYPE: DNA
<213> ORGANISM: Artificial Sequence
<220> FEATURE:
<223> OTHER INFORMATION: Synthetic Construct

<400> SEQUENCE: 130
ccgaaccaca acgtcacaca atgtt                                         25

<210> SEQ ID NO 131
<211> LENGTH: 20
<212> TYPE: DNA
<213> ORGANISM: Artificial Sequence
<220> FEATURE:
<223> OTHER INFORMATION: Synthetic Construct

<400> SEQUENCE: 131
tgaagccaga attgagctag                                               20
```

-continued

<210> SEQ ID NO 132
<211> LENGTH: 18
<212> TYPE: DNA
<213> ORGANISM: Artificial Sequence
<220> FEATURE:
<223> OTHER INFORMATION: Synthetic Construct

<400> SEQUENCE: 132
aggacagggt gttcagaa                                                          18

<210> SEQ ID NO 133
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (5)..(6)
<223> OTHER INFORMATION: locked nucleic acid
<220> FEATURE:
<221> NAME/KEY: misc_feature
<222> LOCATION: (9)..(9)
<223> OTHER INFORMATION: locked nucleic acid

<400> SEQUENCE: 133
cagacgacct tcg                                                               13

<210> SEQ ID NO 134
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (12)..(12)
<223> OTHER INFORMATION: locked nucleic acid

<400> SEQUENCE: 134
atgttcaaaa atcctgca                                                          18

<210> SEQ ID NO 135
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(16)
<223> OTHER INFORMATION: locked nucleic acid

<400> SEQUENCE: 135
ttcatcgtag ggtatttcc                                                         19

<210> SEQ ID NO 136
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: locked nucleic acid

```
<220> FEATURE:
<221> NAME/KEY: misc_feature
<222> LOCATION: (8)..(9)
<223> OTHER INFORMATION: locked nucleic acid
<220> FEATURE:
<221> NAME/KEY: misc_feature
<222> LOCATION: (11)..(12)
<223> OTHER INFORMATION: locked nucleic acid

<400> SEQUENCE: 136
aactaagctc ggc                                                         13

<210> SEQ ID NO 137
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (11)..(11)
<223> OTHER INFORMATION: locked nucleic acid
<220> FEATURE:
<221> NAME/KEY: misc_feature
<222> LOCATION: (18)..(18)
<223> OTHER INFORMATION: locked nucleic acid

<400> SEQUENCE: 137
ctaagattga attgtgtct                                                   19

<210> SEQ ID NO 138
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: locked nucleic acid
<220> FEATURE:
<221> NAME/KEY: misc_feature
<222> LOCATION: (18)..(18)
<223> OTHER INFORMATION: locked nucleic acid

<400> SEQUENCE: 138
taaatctgta aatgcaaaat cta                                              23

<210> SEQ ID NO 139
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (6)..(6)
<223> OTHER INFORMATION: locked nucleic acid
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (10)..(11)
```

-continued

```
<223> OTHER INFORMATION: locked nucleic acid
<220> FEATURE:
<221> NAME/KEY: misc_feature
<222> LOCATION: (13)..(13)
<223> OTHER INFORMATION: locked nucleic acid

<400> SEQUENCE: 139
acagaaacag aggt                                                      14

<210> SEQ ID NO 140
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: locked nucleic acid

<400> SEQUENCE: 140
acaatagtat atagggacga c                                              21

<210> SEQ ID NO 141
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: locked nucleic acid
<220> FEATURE:
<221> NAME/KEY: misc_feature
<222> LOCATION: (16)..(16)
<223> OTHER INFORMATION: locked nucleic acid
<220> FEATURE:
<221> NAME/KEY: misc_feature
<222> LOCATION: (19)..(19)
<223> OTHER INFORMATION: locked nucleic acid

<400> SEQUENCE: 141
ttcacttact tttgaataaa at                                             22

<210> SEQ ID NO 142
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(5)
<223> OTHER INFORMATION: locked nucleic acid
<220> FEATURE:
<221> NAME/KEY: misc_feature
<222> LOCATION: (9)..(10)
<223> OTHER INFORMATION: locked nucleic acid

<400> SEQUENCE: 142
acggagtgtg tac                                                       13

<210> SEQ ID NO 143
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
```

-continued

```
<222> LOCATION: (5)..(5)
<223> OTHER INFORMATION: locked nucleic acid
<220> FEATURE:
<221> NAME/KEY: misc_feature
<222> LOCATION: (9)..(9)
<223> OTHER INFORMATION: locked nucleic acid

<400> SEQUENCE: 143
tttagatggt atagatatag tgt                                    23

<210> SEQ ID NO 144
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (10)..(11)
<223> OTHER INFORMATION: locked nucleic acid

<400> SEQUENCE: 144
cctaattaac aaatcacata                                        20

<210> SEQ ID NO 145
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(5)
<223> OTHER INFORMATION: locked nucleic acid
<220> FEATURE:
<221> NAME/KEY: misc_feature
<222> LOCATION: (7)..(8)
<223> OTHER INFORMATION: locked nucleic acid

<400> SEQUENCE: 145
atggaacaac att                                               13

<210> SEQ ID NO 146
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: locked nucleic acid
<220> FEATURE:
<221> NAME/KEY: misc_feature
<222> LOCATION: (13)..(13)
<223> OTHER INFORMATION: locked nucleic acid

<400> SEQUENCE: 146
tgtataacgt gtcaaagac                                         19

<210> SEQ ID NO 147
<211> LENGTH: 18
<212> TYPE: DNA
<213> ORGANISM: Artificial Sequence
<220> FEATURE:
<223> OTHER INFORMATION: Synthetic Construct
<220> FEATURE:
```

-continued

```
<221> NAME/KEY: misc_feature
<222> LOCATION: (11)..(11)
<223> OTHER INFORMATION: locked nucleic acid
<220> FEATURE:
<221> NAME/KEY: misc_feature
<222> LOCATION: (14)..(14)
<223> OTHER INFORMATION: locked nucleic acid

<400> SEQUENCE: 147
ttgtggaatc gtttcttt                                                  18

<210> SEQ ID NO 148
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: locked nucleic acid
<220> FEATURE:
<221> NAME/KEY: misc_feature
<222> LOCATION: (7)..(8)
<223> OTHER INFORMATION: locked nucleic acid
<220> FEATURE:
<221> NAME/KEY: misc_feature
<222> LOCATION: (11)..(12)
<223> OTHER INFORMATION: locked nucleic acid

<400> SEQUENCE: 148
tgtgtccaga aga                                                       13

<210> SEQ ID NO 149
<211> LENGTH: 18
<212> TYPE: DNA
<213> ORGANISM: Artificial Sequence
<220> FEATURE:
<223> OTHER INFORMATION: Synthetic Construct

<400> SEQUENCE: 149
cataggagga aggtggac                                                  18

<210> SEQ ID NO 150
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (9)..(9)
<223> OTHER INFORMATION: locked nucleic acid
<220> FEATURE:
<221> NAME/KEY: misc_feature
<222> LOCATION: (13)..(13)
<223> OTHER INFORMATION: locked nucleic acid

<400> SEQUENCE: 150
ttacacttgg gtttcag                                                   17

<210> SEQ ID NO 151
<211> LENGTH: 26
<212> TYPE: DNA
<213> ORGANISM: Artificial Sequence
<220> FEATURE:
<223> OTHER INFORMATION: Synthetic Construct

<400> SEQUENCE: 151
cgttgcatag catgttggag aagacc                                         26
```

```
<210> SEQ ID NO 152
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: locked nucleic acid
<220> FEATURE:
<221> NAME/KEY: misc_feature
<222> LOCATION: (16)..(16)
<223> OTHER INFORMATION: locked nucleic acid

<400> SEQUENCE: 152
caagactatg tgttagatt                                                  19

<210> SEQ ID NO 153
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (14)..(14)
<223> OTHER INFORMATION: locked nucleic acid
<220> FEATURE:
<221> NAME/KEY: misc_feature
<222> LOCATION: (17)..(17)
<223> OTHER INFORMATION: locked nucleic acid

<400> SEQUENCE: 153
tcatctgagc tgtcgggtaa tt                                              22

<210> SEQ ID NO 154
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(9)
<223> OTHER INFORMATION: locked nucleic acid
<220> FEATURE:
<221> NAME/KEY: misc_feature
<222> LOCATION: (11)..(12)
<223> OTHER INFORMATION: locked nucleic acid

<400> SEQUENCE: 154
aactgacctc cac                                                        13

<210> SEQ ID NO 155
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (12)..(12)
<223> OTHER INFORMATION: locked nucleic acid

<400> SEQUENCE: 155
aggatgtcat agacagtc                                                   18

<210> SEQ ID NO 156
```

-continued

```
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid

<400> SEQUENCE: 156
tgtagactta cactgacaa                                                     19

<210> SEQ ID NO 157
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: locked nucleic acid
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (10)..(11)
<223> OTHER INFORMATION: locked nucleic acid

<400> SEQUENCE: 157
ctggacaagc aga                                                           13

<210> SEQ ID NO 158
<211> LENGTH: 21
<212> TYPE: DNA
<213> ORGANISM: Artificial Sequence
<220> FEATURE:
<223> OTHER INFORMATION: Synthetic Construct

<400> SEQUENCE: 158
agcacacaag tagatattcg c                                                  21

<210> SEQ ID NO 159
<211> LENGTH: 19
<212> TYPE: DNA
<213> ORGANISM: Artificial Sequence
<220> FEATURE:
<223> OTHER INFORMATION: Synthetic Construct

<400> SEQUENCE: 159
tagtagaaca gttggggca                                                     19

<210> SEQ ID NO 160
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: locked nucleic acid
<220> FEATURE:
<221> NAME/KEY: misc_feature
<222> LOCATION: (7)..(7)
<223> OTHER INFORMATION: locked nucleic acid
<220> FEATURE:
<221> NAME/KEY: misc_feature
```

<222> LOCATION: (9)..(10)
<223> OTHER INFORMATION: locked nucleic acid

<400> SEQUENCE: 160
taacagctct tgc                                                      13

<210> SEQ ID NO 161
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (10)..(10)
<223> OTHER INFORMATION: locked nucleic acid
<220> FEATURE:
<221> NAME/KEY: misc_feature
<222> LOCATION: (16)..(16)
<223> OTHER INFORMATION: locked nucleic acid

<400> SEQUENCE: 161
aaattgcatg aactaagc                                                 18

<210> SEQ ID NO 162
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid

<400> SEQUENCE: 162
ttaactgacc tttgcagt                                                 18

<210> SEQ ID NO 163
<211> LENGTH: 30
<212> TYPE: DNA
<213> ORGANISM: Artificial Sequence
<220> FEATURE:
<223> OTHER INFORMATION: Synthetic Construct

<400> SEQUENCE: 163
cggcattgga aataccctac gatgaactaa                                    30

<210> SEQ ID NO 164
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: locked nucleic acid
<220> FEATURE:
<221> NAME/KEY: misc_feature
<222> LOCATION: (18)..(18)
<223> OTHER INFORMATION: locked nucleic acid

<400> SEQUENCE: 164
cagaaacaga ggtattagat                                               20

<210> SEQ ID NO 165
<211> LENGTH: 20
<212> TYPE: DNA

```
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: locked nucleic acid
<220> FEATURE:
<221> NAME/KEY: misc_feature
<222> LOCATION: (17)..(17)
<223> OTHER INFORMATION: locked nucleic acid

<400> SEQUENCE: 165
ttaaacattt tgtacacact                                                 20

<210> SEQ ID NO 166
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(5)
<223> OTHER INFORMATION: locked nucleic acid
<220> FEATURE:
<221> NAME/KEY: misc_feature
<222> LOCATION: (7)..(8)
<223> OTHER INFORMATION: locked nucleic acid

<400> SEQUENCE: 166
acgacacacc aca                                                        13

<210> SEQ ID NO 167
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (12)..(12)
<223> OTHER INFORMATION: locked nucleic acid
<220> FEATURE:
<221> NAME/KEY: misc_feature
<222> LOCATION: (17)..(17)
<223> OTHER INFORMATION: locked nucleic acid

<400> SEQUENCE: 167
attttattca aaagtaagtg a                                               21

<210> SEQ ID NO 168
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: locked nucleic acid
<220> FEATURE:
<221> NAME/KEY: misc_feature
<222> LOCATION: (13)..(13)
<223> OTHER INFORMATION: locked nucleic acid
<220> FEATURE:
<221> NAME/KEY: misc_feature
<222> LOCATION: (17)..(17)
<223> OTHER INFORMATION: locked nucleic acid
```

-continued

<400> SEQUENCE: 168
cctttgtttg tcaatttttc                                                                    20

<210> SEQ ID NO 169
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(6)
<223> OTHER INFORMATION: locked nucleic acid
<220> FEATURE:
<221> NAME/KEY: misc_feature
<222> LOCATION: (10)..(12)
<223> OTHER INFORMATION: locked nucleic acid

<400> SEQUENCE: 169
tagtgtgtat gga                                                                           13

<210> SEQ ID NO 170
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (17)..(17)
<223> OTHER INFORMATION: locked nucleic acid
<220> FEATURE:
<221> NAME/KEY: misc_feature
<222> LOCATION: (21)..(21)
<223> OTHER INFORMATION: locked nucleic acid

<400> SEQUENCE: 170
tatatgtgat ttgttaatta ggt                                                                23

<210> SEQ ID NO 171
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: locked nucleic acid
<220> FEATURE:
<221> NAME/KEY: misc_feature
<222> LOCATION: (11)..(11)
<223> OTHER INFORMATION: locked nucleic acid

<400> SEQUENCE: 171
tccaaatgtc tttgttttc                                                                     20

<210> SEQ ID NO 172
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (6)..(6)

-continued

```
<223> OTHER INFORMATION: locked nucleic acid
<220> FEATURE:
<221> NAME/KEY: misc_feature
<222> LOCATION: (8)..(11)
<223> OTHER INFORMATION: locked nucleic acid

<400> SEQUENCE: 172
ccgttgtgtc cag                                                    13

<210> SEQ ID NO 173
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(16)
<223> OTHER INFORMATION: locked nucleic acid
<220> FEATURE:
<221> NAME/KEY: misc_feature
<222> LOCATION: (7)..(7)
<223> OTHER INFORMATION: locked nucleic acid

<400> SEQUENCE: 173
taaaaagaaa cgattccac                                              19

<210> SEQ ID NO 174
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid

<400> SEQUENCE: 174
tttcagtacg aggtcttc                                               18

<210> SEQ ID NO 175
<211> LENGTH: 20
<212> TYPE: DNA
<213> ORGANISM: Artificial Sequence
<220> FEATURE:
<223> OTHER INFORMATION: Synthetic Construct

<400> SEQUENCE: 175
aaggtggaca ggacgttgca                                             20

<210> SEQ ID NO 176
<211> LENGTH: 17
<212> TYPE: DNA
<213> ORGANISM: Artificial Sequence
<220> FEATURE:
<223> OTHER INFORMATION: Synthetic Construct

<400> SEQUENCE: 176
tggagaaaca cctacgt                                                17

<210> SEQ ID NO 177
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
```

-continued

```
<222> LOCATION: (12)..(12)
<223> OTHER INFORMATION: locked nucleic acid

<400> SEQUENCE: 177
taattgctca taacagtgga                                          20

<210> SEQ ID NO 178
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(6)
<223> OTHER INFORMATION: locked nucleic acid

<400> SEQUENCE: 178
aacctgaggc aac                                                 13

<210> SEQ ID NO 179
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (17)..(17)
<223> OTHER INFORMATION: locked nucleic acid

<400> SEQUENCE: 179
agatgaggag gatgtcat                                            18

<210> SEQ ID NO 180
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (7)..(7)
<223> OTHER INFORMATION: locked nucleic acid
<220> FEATURE:
<221> NAME/KEY: misc_feature
<222> LOCATION: (14)..(14)
<223> OTHER INFORMATION: locked nucleic acid

<400> SEQUENCE: 180
aggtaacgat attgtaatt                                           19

<210> SEQ ID NO 181
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(6)
<223> OTHER INFORMATION: locked nucleic acid
<220> FEATURE:
<221> NAME/KEY: misc_feature
<222> LOCATION: (8)..(8)
<223> OTHER INFORMATION: locked nucleic acid
<220> FEATURE:
```

-continued

```
<221> NAME/KEY: misc_feature
<222> LOCATION: (11)..(11)
<223> OTHER INFORMATION: locked nucleic acid

<400> SEQUENCE: 181
caagcagaac cg                                                      12

<210> SEQ ID NO 182
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (15)..(15)
<223> OTHER INFORMATION: locked nucleic acid

<400> SEQUENCE: 182
tgtcagtgta agtctaca                                                18

<210> SEQ ID NO 183
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (14)..(14)
<223> OTHER INFORMATION: locked nucleic acid

<400> SEQUENCE: 183
tccaaatgag cccattaa                                                18

<210> SEQ ID NO 184
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(7)
<223> OTHER INFORMATION: locked nucleic acid
<220> FEATURE:
<221> NAME/KEY: misc_feature
<222> LOCATION: (9)..(9)
<223> OTHER INFORMATION: locked nucleic acid
<220> FEATURE:
<221> NAME/KEY: misc_feature
<222> LOCATION: (12)..(12)
<223> OTHER INFORMATION: locked nucleic acid

<400> SEQUENCE: 184
tgtacagagc aca                                                     13

<210> SEQ ID NO 185
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(16)
<223> OTHER INFORMATION: locked nucleic acid
```

<400> SEQUENCE: 185
ttcaagacac tgaggaaa                                                            18

<210> SEQ ID NO 186
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (9)..(9)
<223> OTHER INFORMATION: locked nucleic acid
<220> FEATURE:
<221> NAME/KEY: misc_feature
<222> LOCATION: (17)..(17)
<223> OTHER INFORMATION: locked nucleic acid

<400> SEQUENCE: 186
aatgttgtgt atagttgtct c                                                        21

<210> SEQ ID NO 187
<211> LENGTH: 27
<212> TYPE: DNA
<213> ORGANISM: Artificial Sequence
<220> FEATURE:
<223> OTHER INFORMATION: Synthetic Construct

<400> SEQUENCE: 187
aacattgcat gatttgtgcc aagcatt                                                  27

<210> SEQ ID NO 188
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(16)
<223> OTHER INFORMATION: locked nucleic acid

<400> SEQUENCE: 188
aatgcaaaaa acctttgc                                                            18

<210> SEQ ID NO 189
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid
<220> FEATURE:
<221> NAME/KEY: misc_feature
<222> LOCATION: (17)..(17)
<223> OTHER INFORMATION: locked nucleic acid

<400> SEQUENCE: 189
tccctctcta tatacaact                                                           19

<210> SEQ ID NO 190

```
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (6)..(8)
<223> OTHER INFORMATION: locked nucleic acid
<220> FEATURE:
<221> NAME/KEY: misc_feature
<222> LOCATION: (11)..(12)
<223> OTHER INFORMATION: locked nucleic acid

<400> SEQUENCE: 190
cgatctgagg tat                                                           13

<210> SEQ ID NO 191
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: locked nucleic acid
<220> FEATURE:
<221> NAME/KEY: misc_feature
<222> LOCATION: (11)..(11)
<223> OTHER INFORMATION: locked nucleic acid
<220> FEATURE:
<221> NAME/KEY: misc_feature
<222> LOCATION: (18)..(18)
<223> OTHER INFORMATION: locked nucleic acid

<400> SEQUENCE: 191
aatccatttg gaatatgta                                                     19

<210> SEQ ID NO 192
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: locked nucleic acid
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid
<220> FEATURE:
<221> NAME/KEY: misc_feature
<222> LOCATION: (14)..(14)
<223> OTHER INFORMATION: locked nucleic acid

<400> SEQUENCE: 192
ccatatacag aataattata atg                                                23

<210> SEQ ID NO 193
<211> LENGTH: 13
<212> TYPE: DNA
<213> ORGANISM: Artificial Sequence
```

-continued

```
<220> FEATURE:
<223> OTHER INFORMATION: Synthetic Construct
<220> FEATURE:
<221> NAME/KEY: misc_feature
<222> LOCATION: (3)..(5)
<223> OTHER INFORMATION: locked nucleic acid
<220> FEATURE:
<221> NAME/KEY: misc_feature
<222> LOCATION: (10)..(11)
<223> OTHER INFORMATION: locked nucleic acid

<400> SEQUENCE: 193
ctgtgtttgc ggt                                                      13

<210> SEQ ID NO 194
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: locked nucleic acid
<220> FEATURE:
<221> NAME/KEY: misc_feature
<222> LOCATION: (15)..(16)
<223> OTHER INFORMATION: locked nucleic acid

<400> SEQUENCE: 194
tgaaatatta attaggtgt                                                19

<210> SEQ ID NO 195
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(16)
<223> OTHER INFORMATION: locked nucleic acid

<400> SEQUENCE: 195
tttaaatcca catgtcgtt                                                19

<210> SEQ ID NO 196
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (7)..(10)
<223> OTHER INFORMATION: locked nucleic acid
<220> FEATURE:
<221> NAME/KEY: misc_feature
<222> LOCATION: (12)..(12)
<223> OTHER INFORMATION: locked nucleic acid

<400> SEQUENCE: 196
tgtgtcctca aga                                                      13

<210> SEQ ID NO 197
<211> LENGTH: 19
<212> TYPE: DNA
```

-continued

```
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (7)..(7)
<223> OTHER INFORMATION: locked nucleic acid
<220> FEATURE:
<221> NAME/KEY: misc_feature
<222> LOCATION: (11)..(11)
<223> OTHER INFORMATION: locked nucleic acid
<220> FEATURE:
<221> NAME/KEY: misc_feature
<222> LOCATION: (18)..(18)
<223> OTHER INFORMATION: locked nucleic acid

<400> SEQUENCE: 197
caaacgattt cataatatt                                                19

<210> SEQ ID NO 198
<211> LENGTH: 18
<212> TYPE: DNA
<213> ORGANISM: Artificial Sequence
<220> FEATURE:
<223> OTHER INFORMATION: Synthetic Construct

<400> SEQUENCE: 198
cagtgcagtt tctctacg                                                 18

<210> SEQ ID NO 199
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: locked nucleic acid
<220> FEATURE:
<221> NAME/KEY: misc_feature
<222> LOCATION: (6)..(6)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid

<400> SEQUENCE: 199
acacgccgca cag                                                      13

<210> SEQ ID NO 200
<211> LENGTH: 18
<212> TYPE: DNA
<213> ORGANISM: Artificial Sequence
<220> FEATURE:
<223> OTHER INFORMATION: Synthetic Construct

<400> SEQUENCE: 200
acacaagcca acgttaaa                                                 18

<210> SEQ ID NO 201
<211> LENGTH: 19
<212> TYPE: DNA
<213> ORGANISM: Artificial Sequence
<220> FEATURE:
<223> OTHER INFORMATION: Synthetic Construct
```

-continued

```
<220> FEATURE:
<221> NAME/KEY: misc_feature
<222> LOCATION: (12)..(12)
<223> OTHER INFORMATION: locked nucleic acid
<220> FEATURE:
<221> NAME/KEY: misc_feature
<222> LOCATION: (15)..(15)
<223> OTHER INFORMATION: locked nucleic acid

<400> SEQUENCE: 201
aattgctcat agcagtata                                             19

<210> SEQ ID NO 202
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(6)
<223> OTHER INFORMATION: locked nucleic acid
<220> FEATURE:
<221> NAME/KEY: misc_feature
<222> LOCATION: (9)..(10)
<223> OTHER INFORMATION: locked nucleic acid

<400> SEQUENCE: 202
atcctgaacc aac                                                   13

<210> SEQ ID NO 203
<211> LENGTH: 18
<212> TYPE: DNA
<213> ORGANISM: Artificial Sequence
<220> FEATURE:
<223> OTHER INFORMATION: Synthetic Construct

<400> SEQUENCE: 203
aagtgacagc tcagatga                                              18

<210> SEQ ID NO 204
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: locked nucleic acid
<220> FEATURE:
<221> NAME/KEY: misc_feature
<222> LOCATION: (15)..(15)
<223> OTHER INFORMATION: locked nucleic acid

<400> SEQUENCE: 204
ttacaatgta gtaatcagct                                            20

<210> SEQ ID NO 205
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (5)..(6)
```

-continued

<223> OTHER INFORMATION: locked nucleic acid
<220> FEATURE:
<221> NAME/KEY: misc_feature
<222> LOCATION: (9)..(9)
<223> OTHER INFORMATION: locked nucleic acid

<400> SEQUENCE: 205
cggtccaagc ctt                                                                         13

<210> SEQ ID NO 206
<211> LENGTH: 22
<212> TYPE: DNA
<213> ORGANISM: Artificial Sequence
<220> FEATURE:
<223> OTHER INFORMATION: Synthetic Construct

<400> SEQUENCE: 206
taacaccaca gttcgtttat gt                                                               22

<210> SEQ ID NO 207
<211> LENGTH: 21
<212> TYPE: DNA
<213> ORGANISM: Artificial Sequence
<220> FEATURE:
<223> OTHER INFORMATION: Synthetic Construct

<400> SEQUENCE: 207
acaatattca ctgtgcccat a                                                                21

<210> SEQ ID NO 208
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (5)..(6)
<223> OTHER INFORMATION: locked nucleic acid
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (10)..(11)
<223> OTHER INFORMATION: locked nucleic acid

<400> SEQUENCE: 208
tgacctacga acc                                                                         13

<210> SEQ ID NO 209
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: locked nucleic acid
<220> FEATURE:
<221> NAME/KEY: misc_feature
<222> LOCATION: (6)..(7)
<223> OTHER INFORMATION: locked nucleic acid
<220> FEATURE:
<221> NAME/KEY: misc_feature -continued

```
<222> LOCATION: (9)..(9)
<223> OTHER INFORMATION: locked nucleic acid
<220> FEATURE:
<221> NAME/KEY: misc_feature
<222> LOCATION: (11)..(12)
<223> OTHER INFORMATION: locked nucleic acid

<400> SEQUENCE: 209
cagtacagca agt                                                    13

<210> SEQ ID NO 210
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (15)..(15)
<223> OTHER INFORMATION: locked nucleic acid

<400> SEQUENCE: 210
caagcattgg agacaacta                                              19

<210> SEQ ID NO 211
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (15)..(15)
<223> OTHER INFORMATION: locked nucleic acid

<400> SEQUENCE: 211
tatacctcag atcgttgc                                               18

<210> SEQ ID NO 212
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (5)..(6)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid
<220> FEATURE:
<221> NAME/KEY: misc_feature
<222> LOCATION: (12)..(12)
<223> OTHER INFORMATION: locked nucleic acid

<400> SEQUENCE: 212
tccacgcact gta                                                    13

<210> SEQ ID NO 213
<211> LENGTH: 18
<212> TYPE: DNA
<213> ORGANISM: Artificial Sequence
<220> FEATURE:
<223> OTHER INFORMATION: Synthetic Construct
<220> FEATURE:
```

-continued

```
<221> NAME/KEY: misc_feature
<222> LOCATION: (6)..(6)
<223> OTHER INFORMATION: locked nucleic acid

<400> SEQUENCE: 213
tgattttgca tttgcaga                                                      18

<210> SEQ ID NO 214
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (9)..(9)
<223> OTHER INFORMATION: locked nucleic acid
<220> FEATURE:
<221> NAME/KEY: misc_feature
<222> LOCATION: (14)..(14)
<223> OTHER INFORMATION: locked nucleic acid

<400> SEQUENCE: 214
caaacacagt ttacatat                                                      18

<210> SEQ ID NO 215
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(5)
<223> OTHER INFORMATION: locked nucleic acid
<220> FEATURE:
<221> NAME/KEY: misc_feature
<222> LOCATION: (7)..(9)
<223> OTHER INFORMATION: locked nucleic acid

<400> SEQUENCE: 215
ttccctctct ata                                                           13

<210> SEQ ID NO 216
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: locked nucleic acid
<220> FEATURE:
<221> NAME/KEY: misc_feature
<222> LOCATION: (9)..(9)
<223> OTHER INFORMATION: locked nucleic acid
<220> FEATURE:
<221> NAME/KEY: misc_feature
<222> LOCATION: (18)..(18)
<223> OTHER INFORMATION: locked nucleic acid

<400> SEQUENCE: 216
gttcttatct aaaattagtg                                                    20

<210> SEQ ID NO 217
<211> LENGTH: 21
```

```
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (9)..(9)
<223> OTHER INFORMATION: locked nucleic acid
<220> FEATURE:
<221> NAME/KEY: misc_feature
<222> LOCATION: (16)..(16)
<223> OTHER INFORMATION: locked nucleic acid

<400> SEQUENCE: 217
tttaactgtt tgttctaatg t                                              21

<210> SEQ ID NO 218
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(5)
<223> OTHER INFORMATION: locked nucleic acid
<220> FEATURE:
<221> NAME/KEY: misc_feature
<222> LOCATION: (10)..(12)
<223> OTHER INFORMATION: locked nucleic acid

<400> SEQUENCE: 218
ttccatatac aga                                                       13

<210> SEQ ID NO 219
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: locked nucleic acid
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (9)..(12)
<223> OTHER INFORMATION: locked nucleic acid

<400> SEQUENCE: 219
tctgtatatg gaa                                                       13

<210> SEQ ID NO 220
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (14)..(14)
<223> OTHER INFORMATION: locked nucleic acid
<220> FEATURE:
<221> NAME/KEY: misc_feature
<222> LOCATION: (20)..(20)
<223> OTHER INFORMATION: locked nucleic acid

<400> SEQUENCE: 220
```
aggtgtatta tatgtcaaag a                                                                21

<210> SEQ ID NO 221
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (13)..(15)
<223> OTHER INFORMATION: locked nucleic acid

<400> SEQUENCE: 221
atattatgaa atcgtttgtt                                                                  20

<210> SEQ ID NO 222
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (7)..(9)
<223> OTHER INFORMATION: locked nucleic acid
<220> FEATURE:
<221> NAME/KEY: misc_feature
<222> LOCATION: (12)..(12)
<223> OTHER INFORMATION: locked nucleic acid

<400> SEQUENCE: 222
ttgtgtcctc aag                                                                         13

<210> SEQ ID NO 223
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: locked nucleic acid
<220> FEATURE:
<221> NAME/KEY: misc_feature
<222> LOCATION: (9)..(11)
<223> OTHER INFORMATION: locked nucleic acid

<400> SEQUENCE: 223
cgacatgtgg att                                                                         13

<210> SEQ ID NO 224
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: locked nucleic acid
<220> FEATURE:
<221> NAME/KEY: misc_feature

```
<222> LOCATION: (11)..(11)
<223> OTHER INFORMATION: locked nucleic acid
<220> FEATURE:
<221> NAME/KEY: misc_feature
<222> LOCATION: (15)..(15)
<223> OTHER INFORMATION: locked nucleic acid

<400> SEQUENCE: 224
aggaatatgt tttagatt                                                    18

<210> SEQ ID NO 225
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(16)
<223> OTHER INFORMATION: locked nucleic acid

<400> SEQUENCE: 225
atctgagctg tcacttaa                                                    18

<210> SEQ ID NO 226
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(6)
<223> OTHER INFORMATION: locked nucleic acid
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid

<400> SEQUENCE: 226
tgacctatac tgc                                                         13

<210> SEQ ID NO 227
<211> LENGTH: 17
<212> TYPE: DNA
<213> ORGANISM: Artificial Sequence
<220> FEATURE:
<223> OTHER INFORMATION: Synthetic Construct

<400> SEQUENCE: 227
gaggatgaag gcttgga                                                     17

<210> SEQ ID NO 228
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: locked nucleic acid
<220> FEATURE:
<221> NAME/KEY: misc_feature
<222> LOCATION: (14)..(14)
<223> OTHER INFORMATION: locked nucleic acid
```

-continued

```
<400> SEQUENCE: 228
tgacaacagg ttacaat                                                        17

<210> SEQ ID NO 229
<211> LENGTH: 23
<212> TYPE: DNA
<213> ORGANISM: Artificial Sequence
<220> FEATURE:
<223> OTHER INFORMATION: Synthetic Construct

<400> SEQUENCE: 229
ccagatggac aagcacaacc agc                                                 23

<210> SEQ ID NO 230
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: locked nucleic acid

<400> SEQUENCE: 230
tgtcaacagt acagcaa                                                        17

<210> SEQ ID NO 231
<211> LENGTH: 18
<212> TYPE: DNA
<213> ORGANISM: Artificial Sequence
<220> FEATURE:
<223> OTHER INFORMATION: Synthetic Construct

<400> SEQUENCE: 231
aggtagggca cacaatat                                                       18

<210> SEQ ID NO 232
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: locked nucleic acid
<220> FEATURE:
<221> NAME/KEY: misc_feature
<222> LOCATION: (7)..(10)
<223> OTHER INFORMATION: locked nucleic acid

<400> SEQUENCE: 232
accatacagc aac                                                            13

<210> SEQ ID NO 233
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (8)..(8)
<223> OTHER INFORMATION: locked nucleic acid
```

<400> SEQUENCE: 233
ctgaacgacc ttacaaa                                                        17

<210> SEQ ID NO 234
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (11)..(11)
<223> OTHER INFORMATION: locked nucleic acid
<220> FEATURE:
<221> NAME/KEY: misc_feature
<222> LOCATION: (15)..(16)
<223> OTHER INFORMATION: locked nucleic acid

<400> SEQUENCE: 234
atacacaatt caaacaaa                                                       18

<210> SEQ ID NO 235
<211> LENGTH: 28
<212> TYPE: DNA
<213> ORGANISM: Artificial Sequence
<220> FEATURE:
<223> OTHER INFORMATION: Synthetic Construct

<400> SEQUENCE: 235
tgatttgtgc aacgaggtag aagaaagc                                            28

<210> SEQ ID NO 236
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (5)..(8)
<223> OTHER INFORMATION: locked nucleic acid
<220> FEATURE:
<221> NAME/KEY: misc_feature
<222> LOCATION: (11)..(11)
<223> OTHER INFORMATION: locked nucleic acid

<400> SEQUENCE: 236
cgaggtagaa gaa                                                            13

<210> SEQ ID NO 237
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (11)..(11)
<223> OTHER INFORMATION: locked nucleic acid
<220> FEATURE:
<221> NAME/KEY: misc_feature
<222> LOCATION: (15)..(15)

-continued

<223> OTHER INFORMATION: locked nucleic acid

<400> SEQUENCE: 237
caaacaagaa ttacag                                                              16

<210> SEQ ID NO 238
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: locked nucleic acid
<220> FEATURE:
<221> NAME/KEY: misc_feature
<222> LOCATION: (7)..(7)
<223> OTHER INFORMATION: locked nucleic acid
<220> FEATURE:
<221> NAME/KEY: misc_feature
<222> LOCATION: (14)..(14)
<223> OTHER INFORMATION: locked nucleic acid

<400> SEQUENCE: 238
ccttctctat atactata                                                            18

<210> SEQ ID NO 239
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(6)
<223> OTHER INFORMATION: locked nucleic acid
<220> FEATURE:
<221> NAME/KEY: misc_feature
<222> LOCATION: (10)..(11)
<223> OTHER INFORMATION: locked nucleic acid

<400> SEQUENCE: 239
agtcatatac ctcac                                                               15

<210> SEQ ID NO 240
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: locked nucleic acid
<220> FEATURE:
<221> NAME/KEY: misc_feature
<222> LOCATION: (13)..(14)
<223> OTHER INFORMATION: locked nucleic acid

<400> SEQUENCE: 240
attcaaaaat aagtgaat                                                            18

<210> SEQ ID NO 241
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature -continued

```
<222> LOCATION: (13)..(13)
<223> OTHER INFORMATION: locked nucleic acid

<400> SEQUENCE: 241
taactgtttg ttgcattgt                                              19

<210> SEQ ID NO 242
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(5)
<223> OTHER INFORMATION: locked nucleic acid
<220> FEATURE:
<221> NAME/KEY: misc_feature
<222> LOCATION: (10)..(12)
<223> OTHER INFORMATION: locked nucleic acid

<400> SEQUENCE: 242
tagtgtgtat gga                                                    13

<210> SEQ ID NO 243
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (10)..(11)
<223> OTHER INFORMATION: locked nucleic acid
<220> FEATURE:
<221> NAME/KEY: misc_feature
<222> LOCATION: (16)..(16)
<223> OTHER INFORMATION: locked nucleic acid

<400> SEQUENCE: 243
tgtcatttat taattaggt                                              19

<210> SEQ ID NO 244
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (10)..(10)
<223> OTHER INFORMATION: locked nucleic acid
<220> FEATURE:
<221> NAME/KEY: misc_feature
<222> LOCATION: (14)..(14)
<223> OTHER INFORMATION: locked nucleic acid

<400> SEQUENCE: 244
ttcttctaaa tgtctttgc                                              19

<210> SEQ ID NO 245
<211> LENGTH: 13
<212> TYPE: DNA
<213> ORGANISM: Artificial Sequence
<220> FEATURE:
<223> OTHER INFORMATION: Synthetic Construct
<220> FEATURE:
```

-continued

```
<221> NAME/KEY: misc_feature
<222> LOCATION: (3)..(4)
<223> OTHER INFORMATION: locked nucleic acid
<220> FEATURE:
<221> NAME/KEY: misc_feature
<222> LOCATION: (10)..(12)
<223> OTHER INFORMATION: locked nucleic acid

<400> SEQUENCE: 245
tgtcaaaaac cgc                                                    13

<210> SEQ ID NO 246
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (13)..(13)
<223> OTHER INFORMATION: locked nucleic acid

<400> SEQUENCE: 246
cgattccata acatcggt                                               18

<210> SEQ ID NO 247
<211> LENGTH: 17
<212> TYPE: DNA
<213> ORGANISM: Artificial Sequence
<220> FEATURE:
<223> OTHER INFORMATION: Synthetic Construct

<400> SEQUENCE: 247
tcggtttctc tacgtgt                                                17

<210> SEQ ID NO 248
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(6)
<223> OTHER INFORMATION: locked nucleic acid
<220> FEATURE:
<221> NAME/KEY: misc_feature
<222> LOCATION: (9)..(10)
<223> OTHER INFORMATION: locked nucleic acid

<400> SEQUENCE: 248
cggtgtatgt cct                                                    13

<210> SEQ ID NO 249
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: locked nucleic acid
<220> FEATURE:
<221> NAME/KEY: misc_feature
<222> LOCATION: (9)..(9)
<223> OTHER INFORMATION: locked nucleic acid
<220> FEATURE:
<221> NAME/KEY: misc_feature
<222> LOCATION: (17)..(17)
<223> OTHER INFORMATION: locked nucleic acid
```

```
<400> SEQUENCE: 249
catggagaaa taactaca                                                    18

<210> SEQ ID NO 250
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (10)..(10)
<223> OTHER INFORMATION: locked nucleic acid
<220> FEATURE:
<221> NAME/KEY: misc_feature
<222> LOCATION: (13)..(13)
<223> OTHER INFORMATION: locked nucleic acid
<220> FEATURE:
<221> NAME/KEY: misc_feature
<222> LOCATION: (15)..(15)
<223> OTHER INFORMATION: locked nucleic acid

<400> SEQUENCE: 250
ctcataacag tataggtc                                                    18

<210> SEQ ID NO 251
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (6)..(6)
<223> OTHER INFORMATION: locked nucleic acid
<220> FEATURE:
<221> NAME/KEY: misc_feature
<222> LOCATION: (8)..(9)
<223> OTHER INFORMATION: locked nucleic acid
<220> FEATURE:
<221> NAME/KEY: misc_feature
<222> LOCATION: (11)..(12)
<223> OTHER INFORMATION: locked nucleic acid

<400> SEQUENCE: 251
tgcaagacta tgt                                                         13

<210> SEQ ID NO 252
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: locked nucleic acid

<400> SEQUENCE: 252
aattgtgtga cagctca                                                     17

<210> SEQ ID NO 253
<211> LENGTH: 18
<212> TYPE: DNA
<213> ORGANISM: Artificial Sequence
<220> FEATURE:
```

-continued

<223> OTHER INFORMATION: Synthetic Construct

<400> SEQUENCE: 253
taattggagg tgtctggt                                                                                             18

<210> SEQ ID NO 254
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(5)
<223> OTHER INFORMATION: locked nucleic acid
<220> FEATURE:
<221> NAME/KEY: misc_feature
<222> LOCATION: (7)..(7)
<223> OTHER INFORMATION: locked nucleic acid
<220> FEATURE:
<221> NAME/KEY: misc_feature
<222> LOCATION: (10)..(11)
<223> OTHER INFORMATION: locked nucleic acid

<400> SEQUENCE: 254
ttgcttgtcc agc                                                                                                  13

<210> SEQ ID NO 255
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (15)..(15)
<223> OTHER INFORMATION: locked nucleic acid

<400> SEQUENCE: 255
taatattgta acgtcctgt                                                                                            19

<210> SEQ ID NO 256
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (11)..(11)
<223> OTHER INFORMATION: locked nucleic acid
<220> FEATURE:
<221> NAME/KEY: misc_feature
<222> LOCATION: (16)..(16)
<223> OTHER INFORMATION: locked nucleic acid

<400> SEQUENCE: 256
ataaatcttc caatttacg                                                                                            19

-continued

```
<210> SEQ ID NO 257
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: locked nucleic acid
<220> FEATURE:
<221> NAME/KEY: misc_feature
<222> LOCATION: (6)..(7)
<223> OTHER INFORMATION: locked nucleic acid
<220> FEATURE:
<221> NAME/KEY: misc_feature
<222> LOCATION: (12)..(12)
<223> OTHER INFORMATION: locked nucleic acid

<400> SEQUENCE: 257
cactacgtct gtg                                             13

<210> SEQ ID NO 258
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (13)..(13)
<223> OTHER INFORMATION: locked nucleic acid

<400> SEQUENCE: 258
tgcatgattt gtgcaac                                         17

<210> SEQ ID NO 259
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (14)..(4)
<223> OTHER INFORMATION: locked nucleic acid

<400> SEQUENCE: 259
cttgtttgca gtatacac                                        18

<210> SEQ ID NO 260
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(6)
<223> OTHER INFORMATION: locked nucleic acid
<220> FEATURE:
<221> NAME/KEY: misc_feature
<222> LOCATION: (8)..(10)
<223> OTHER INFORMATION: locked nucleic acid
<220> FEATURE:
<221> NAME/KEY: misc_feature
<222> LOCATION: (12)..(12)
<223> OTHER INFORMATION: locked nucleic acid
```

```
<400> SEQUENCE: 260
aaagcatcca tga                                                    13

<210> SEQ ID NO 261
<211> LENGTH: 18
<212> TYPE: DNA
<213> ORGANISM: Artificial Sequence
<220> FEATURE:
<223> OTHER INFORMATION: Synthetic Construct

<400> SEQUENCE: 261
cagcggagtg aggtatat                                               18

<210> SEQ ID NO 262
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid
<220> FEATURE:
<221> NAME/KEY: misc_feature
<222> LOCATION: (15)..(16)
<223> OTHER INFORMATION: locked nucleic acid

<400> SEQUENCE: 262
aattttaaac atttcatg                                              18

<210> SEQ ID NO 263
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (11)..(12)
<223> OTHER INFORMATION: locked nucleic acid

<400> SEQUENCE: 263
agagaaggcc agc                                                   13

<210> SEQ ID NO 264
<211> LENGTH: 21
<212> TYPE: DNA
<213> ORGANISM: Artificial Sequence
<220> FEATURE:
<223> OTHER INFORMATION: Synthetic Construct
```

-continued

```
<220> FEATURE:
<221> NAME/KEY: misc_feature
<222> LOCATION: (4)..(4)
<223> OTHER INFORMATION: locked nucleic acid
<220> FEATURE:
<221> NAME/KEY: misc_feature
<222> LOCATION: (7)..(7)
<223> OTHER INFORMATION: locked nucleic acid
<220> FEATURE:
<221> NAME/KEY: misc_feature
<222> LOCATION: (11)..(11)
<223> OTHER INFORMATION: locked nucleic acid
<220> FEATURE:
<221> NAME/KEY: misc_feature
<222> LOCATION: (16)..(17)
<223> OTHER INFORMATION: locked nucleic acid

<400> SEQUENCE: 264
aatatagatg gtatagatat a                                            21

<210> SEQ ID NO 265
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid
<220> FEATURE:
<221> NAME/KEY: misc_feature
<222> LOCATION: (17)..(17)
<223> OTHER INFORMATION: locked nucleic acid

<400> SEQUENCE: 265
aataaatgac ataactgttt                                              20

<210> SEQ ID NO 266
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(6)
<223> OTHER INFORMATION: locked nucleic acid
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid

<400> SEQUENCE: 266
ttctccatac aca                                                     13

<210> SEQ ID NO 267
<211> LENGTH: 18
<212> TYPE: DNA
<213> ORGANISM: Artificial Sequence
<220> FEATURE:
```

```
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (6)..(6)
<223> OTHER INFORMATION: locked nucleic acid
<220> FEATURE:
<221> NAME/KEY: misc_feature
<222> LOCATION: (9)..(9)
<223> OTHER INFORMATION: locked nucleic acid
<220> FEATURE:
<221> NAME/KEY: misc_feature
<222> LOCATION: (17)..(17)
<223> OTHER INFORMATION: locked nucleic acid

<400> SEQUENCE: 267
aattaggtgt attacatg                                                    18

<210> SEQ ID NO 268
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid
<220> FEATURE:
<221> NAME/KEY: misc_feature
<222> LOCATION: (14)..(14)
<223> OTHER INFORMATION: locked nucleic acid

<400> SEQUENCE: 268
aatcgttttt tttcttct                                                    18

<210> SEQ ID NO 269
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(5)
<223> OTHER INFORMATION: locked nucleic acid
<220> FEATURE:
<221> NAME/KEY: misc_feature
<222> LOCATION: (7)..(7)
<223> OTHER INFORMATION: locked nucleic acid
<220> FEATURE:
<221> NAME/KEY: misc_feature
<222> LOCATION: (12)..(12)
<223> OTHER INFORMATION: locked nucleic acid

<400> SEQUENCE: 269
ccagttgaaa agca                                                        14

<210> SEQ ID NO 270
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
```

-continued

```
<222> LOCATION: (3)..(3)
<223> OTHER INFORMATION: locked nucleic acid

<400> SEQUENCE: 270
ccataacatc ggtggac                                          17

<210> SEQ ID NO 271
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid

<400> SEQUENCE: 271
acacctcggt ttctcta                                          17

<210> SEQ ID NO 272
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: locked nucleic acid
<220> FEATURE:
<221> NAME/KEY: misc_feature
<222> LOCATION: (7)..(10)
<223> OTHER INFORMATION: locked nucleic acid
<220> FEATURE:
<221> NAME/KEY: misc_feature
<222> LOCATION: (12)..(12)
<223> OTHER INFORMATION: locked nucleic acid

<400> SEQUENCE: 272
tgtatgtcct gtt                                              13

<210> SEQ ID NO 273
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (13)..(13)
<223> OTHER INFORMATION: locked nucleic acid

<400> SEQUENCE: 273
tttagatttg gaacccga                                         18

<210> SEQ ID NO 274
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (13)..(13)
<223> OTHER INFORMATION: locked nucleic acid

<400> SEQUENCE: 274
tatcttcctc ctcctct                                          17
```

```
<210> SEQ ID NO 275
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(7)
<223> OTHER INFORMATION: locked nucleic acid
<220> FEATURE:
<221> NAME/KEY: misc_feature
<222> LOCATION: (12)..(12)
<223> OTHER INFORMATION: locked nucleic acid

<400> SEQUENCE: 275
actgacctat act                                                          13

<210> SEQ ID NO 276
<211> LENGTH: 17
<212> TYPE: DNA
<213> ORGANISM: Artificial Sequence
<220> FEATURE:
<223> OTHER INFORMATION: Synthetic Construct

<400> SEQUENCE: 276
ctattgacgg tccagct                                                      17

<210> SEQ ID NO 277
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid

<400> SEQUENCE: 277
catttacaac aggacgtt                                                     18

<210> SEQ ID NO 278
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(8)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid

<400> SEQUENCE: 278
ccagacacct cc                                                           12

<210> SEQ ID NO 279
<211> LENGTH: 17
<212> TYPE: DNA
<213> ORGANISM: Artificial Sequence
<220> FEATURE:
<223> OTHER INFORMATION: Synthetic Construct
```

<400> SEQUENCE: 279
tgaggcgaca ctacgtc                                                                                          17

<210> SEQ ID NO 280
<211> LENGTH: 23
<212> TYPE: DNA
<213> ORGANISM: Artificial Sequence
<220> FEATURE:
<223> OTHER INFORMATION: Synthetic Construct

<400> SEQUENCE: 280
gtgcccatta ataaatcttc caa                                                                                    23

<210> SEQ ID NO 281
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: locked nucleic acid
<220> FEATURE:
<221> NAME/KEY: misc_feature
<222> LOCATION: (5)..(6)
<223> OTHER INFORMATION: locked nucleic acid
<220> FEATURE:
<221> NAME/KEY: misc_feature
<222> LOCATION: (9)..(10)
<223> OTHER INFORMATION: locked nucleic acid

<400> SEQUENCE: 281
agagcacaca cat                                                                                               13

<210> SEQ ID NO 282
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (8)..(8)
<223> OTHER INFORMATION: locked nucleic acid

<400> SEQUENCE: 282
ctgaacgacc ttacaaa                                                                                           17

<210> SEQ ID NO 283
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (11)..(11)
<223> OTHER INFORMATION: locked nucleic acid
<220> FEATURE:
<221> NAME/KEY: misc_feature
<222> LOCATION: (15)..(16)
<223> OTHER INFORMATION: locked nucleic acid

<400> SEQUENCE: 283

-continued atacacaatt caaacaaa                                                    18

<210> SEQ ID NO 284
<211> LENGTH: 17
<212> TYPE: DNA
<213> ORGANISM: Artificial Sequence
<220> FEATURE:
<223> OTHER INFORMATION: Synthetic Construct

<400> SEQUENCE: 284
cgctttgacg atccaaa                                                     17

<210> SEQ ID NO 285
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: locked nucleic acid
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (14)..(14)
<223> OTHER INFORMATION: locked nucleic acid

<400> SEQUENCE: 285
tcttgtagtg atgtattc                                                    18

<210> SEQ ID NO 286
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: locked nucleic acid
<220> FEATURE:
<221> NAME/KEY: misc_feature
<222> LOCATION: (6)..(8)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid

<400> SEQUENCE: 286
agctaccaga tt                                                          12

<210> SEQ ID NO 287
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (9)..(9)
<223> OTHER INFORMATION: locked nucleic acid

<400> SEQUENCE: 287
cgtatctatt gcctgtgt                                                    18

```
<210> SEQ ID NO 288
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(10)
<223> OTHER INFORMATION: locked nucleic acid
<220> FEATURE:
<221> NAME/KEY: misc_feature
<222> LOCATION: (15)..(15)
<223> OTHER INFORMATION: locked nucleic acid

<400> SEQUENCE: 288
cactatacat aaatctttaa                                              20

<210> SEQ ID NO 289
<211> LENGTH: 29
<212> TYPE: DNA
<213> ORGANISM: Artificial Sequence
<220> FEATURE:
<223> OTHER INFORMATION: Synthetic Construct

<400> SEQUENCE: 289
agcaacattg gaacgcacag aggtatatc                                    29

<210> SEQ ID NO 290
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid
<220> FEATURE:
<221> NAME/KEY: misc_feature
<222> LOCATION: (14)..(14)
<223> OTHER INFORMATION: locked nucleic acid

<400> SEQUENCE: 290
atagagactg tatagca                                                 17

<210> SEQ ID NO 291
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (12)..(14)
<223> OTHER INFORMATION: locked nucleic acid

<400> SEQUENCE: 291
atatcttaat tctctaattc                                              20

<210> SEQ ID NO 292
<211> LENGTH: 14
<212> TYPE: DNA
```

-continued

```
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: locked nucleic acid
<220> FEATURE:
<221> NAME/KEY: misc_feature
<222> LOCATION: (9)..(12)
<223> OTHER INFORMATION: locked nucleic acid

<400> SEQUENCE: 292
tacatttatg gcat                                              14

<210> SEQ ID NO 293
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (10)..(11)
<223> OTHER INFORMATION: locked nucleic acid
<220> FEATURE:
<221> NAME/KEY: misc_feature
<222> LOCATION: (16)..(16)
<223> OTHER INFORMATION: locked nucleic acid

<400> SEQUENCE: 293
tattcaaact ctgtatat                                          18

<210> SEQ ID NO 294
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: locked nucleic acid
<220> FEATURE:
<221> NAME/KEY: misc_feature
<222> LOCATION: (12)..(13)
<223> OTHER INFORMATION: locked nucleic acid

<400> SEQUENCE: 294
caccttatta acaaattat                                         19

<210> SEQ ID NO 295
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: locked nucleic acid
<220> FEATURE:
<221> NAME/KEY: misc_feature
<222> LOCATION: (8)..(9)
<223> OTHER INFORMATION: locked nucleic acid
<220> FEATURE:
<221> NAME/KEY: misc_feature
<222> LOCATION: (11)..(11)
<223> OTHER INFORMATION: locked nucleic acid
```

-continued

<400> SEQUENCE: 295
tccagtgtct ctc                                                                13

<210> SEQ ID NO 296
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid

<400> SEQUENCE: 296
ccagaaacca ttgaacc                                                            17

<210> SEQ ID NO 297
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (15)..(15)
<223> OTHER INFORMATION: locked nucleic acid

<400> SEQUENCE: 297
agctatgctg tgaaatct                                                           18

<210> SEQ ID NO 298
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: locked nucleic acid
<220> FEATURE:
<221> NAME/KEY: misc_feature
<222> LOCATION: (6)..(8)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid

<400> SEQUENCE: 298
cgtagacacc tt                                                                 12

<210> SEQ ID NO 299
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (14)..(14)
<223> OTHER INFORMATION: locked nucleic acid

<400> SEQUENCE: 299
cgagggcagt gtaatac                                                 17

<210> SEQ ID NO 300
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(8)
<223> OTHER INFORMATION: locked nucleic acid

<400> SEQUENCE: 300
cttgtgtttc cctacgt                                                 17

<210> SEQ ID NO 301
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: locked nucleic acid
<220> FEATURE:
<221> NAME/KEY: misc_feature
<222> LOCATION: (6)..(7)
<223> OTHER INFORMATION: locked nucleic acid
<220> FEATURE:
<221> NAME/KEY: misc_feature
<222> LOCATION: (10)..(11)
<223> OTHER INFORMATION: locked nucleic acid

<400> SEQUENCE: 301
cctggtcaca aca                                                     13

<210> SEQ ID NO 302
<211> LENGTH: 22
<212> TYPE: DNA
<213> ORGANISM: Artificial Sequence
<220> FEATURE:
<223> OTHER INFORMATION: Synthetic Construct

<400> SEQUENCE: 302
tgaccaggca cggcaagaaa ga                                           22

<210> SEQ ID NO 303
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(16)
<223> OTHER INFORMATION: locked nucleic acid

<400> SEQUENCE: 303
aacactgcaa gaaattgta                                               19

<210> SEQ ID NO 304
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (12)..(12)
<223> OTHER INFORMATION: locked nucleic acid

<400> SEQUENCE: 304
ctcgtaacac aacaggt                                                      17

<210> SEQ ID NO 305
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(7)
<223> OTHER INFORMATION: locked nucleic acid
<220> FEATURE:
<221> NAME/KEY: misc_feature
<222> LOCATION: (9)..(9)
<223> OTHER INFORMATION: locked nucleic acid
<220> FEATURE:
<221> NAME/KEY: misc_feature
<222> LOCATION: (11)..(12)
<223> OTHER INFORMATION: locked nucleic acid

<400> SEQUENCE: 305
tggaacctca gaa                                                          13

<210> SEQ ID NO 306
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (11)..(11)
<223> OTHER INFORMATION: locked nucleic acid

<400> SEQUENCE: 306
caattaagcg agtcagag                                                     18

<210> SEQ ID NO 307
<211> LENGTH: 17
<212> TYPE: DNA
<213> ORGANISM: Artificial Sequence
<220> FEATURE:
<223> OTHER INFORMATION: Synthetic Construct

<400> SEQUENCE: 307
gtcgggctgg tagttgt                                                      17

<210> SEQ ID NO 308
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(6)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid
<220> FEATURE:
<221> NAME/KEY: misc_feature
<222> LOCATION: (12)..(12)
<223> OTHER INFORMATION: locked nucleic acid -continued

<400> SEQUENCE: 308
cgatgaagca gat                                                          13

<210> SEQ ID NO 309
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (9)..(10)
<223> OTHER INFORMATION: locked nucleic acid
<220> FEATURE:
<221> NAME/KEY: misc_feature
<222> LOCATION: (16)..(16)
<223> OTHER INFORMATION: locked nucleic acid

<400> SEQUENCE: 309
aattttgtgt gtatgttg                                                     18

<210> SEQ ID NO 310
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: locked nucleic acid
<220> FEATURE:
<221> NAME/KEY: misc_feature
<222> LOCATION: (11)..(11)
<223> OTHER INFORMATION: locked nucleic acid

<400> SEQUENCE: 310
ctgctgtagt gttctaa                                                      17

<210> SEQ ID NO 311
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(5)
<223> OTHER INFORMATION: locked nucleic acid
<220> FEATURE:
<221> NAME/KEY: misc_feature
<222> LOCATION: (7)..(8)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid

<400> SEQUENCE: 311
acggcagaat tga                                                          13

<210> SEQ ID NO 312
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (10)..(10)
<223> OTHER INFORMATION: locked nucleic acid 225                                                                                  226

-continued

<400> SEQUENCE: 312
cctacaagct accagatt                                                                  18

<210> SEQ ID NO 313
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (17)..(17)
<223> OTHER INFORMATION: locked nucleic acid

<400> SEQUENCE: 313
tgcaatatac acaggcaa                                                                  18

<210> SEQ ID NO 314
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (6)..(7)
<223> OTHER INFORMATION: locked nucleic acid
<220> FEATURE:
<221> NAME/KEY: misc_feature
<222> LOCATION: (9)..(11)
<223> OTHER INFORMATION: locked nucleic acid

<400> SEQUENCE: 314
cactacaaga cgt                                                                       13

<210> SEQ ID NO 315
<211> LENGTH: 17
<212> TYPE: DNA
<213> ORGANISM: Artificial Sequence
<220> FEATURE:
<223> OTHER INFORMATION: Synthetic Construct

<400> SEQUENCE: 315
aacattggaa cgcacag                                                                   17

<210> SEQ ID NO 316
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (17)..(17)
<223> OTHER INFORMATION: locked nucleic acid

<400> SEQUENCE: 316
tatgctatac agtctctata cac                                                            23

<210> SEQ ID NO 317
<211> LENGTH: 18
<212> TYPE: DNA
<213> ORGANISM: Artificial Sequence
<220> FEATURE:

-continued

```
<223> OTHER INFORMATION: Synthetic Construct
<220> FEATURE:
<221> NAME/KEY: misc_feature
<222> LOCATION: (3)..(5)
<223> OTHER INFORMATION: locked nucleic acid
<220> FEATURE:
<221> NAME/KEY: misc_feature
<222> LOCATION: (8)..(9)
<223> OTHER INFORMATION: locked nucleic acid
<220> FEATURE:
<221> NAME/KEY: misc_feature
<222> LOCATION: (16)..(16)
<223> OTHER INFORMATION: locked nucleic acid

<400> SEQUENCE: 317
aggtatatca atttgctt                                                18

<210> SEQ ID NO 318
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid
<220> FEATURE:
<221> NAME/KEY: misc_feature
<222> LOCATION: (19)..(19)
<223> OTHER INFORMATION: locked nucleic acid

<400> SEQUENCE: 318
catgccataa atgtatagac                                              20

<210> SEQ ID NO 319
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (6)..(6)
<223> OTHER INFORMATION: locked nucleic acid
<220> FEATURE:
<221> NAME/KEY: misc_feature
<222> LOCATION: (12)..(12)
<223> OTHER INFORMATION: locked nucleic acid

<400> SEQUENCE: 319
ccatatacag agtttgaa                                                18

<210> SEQ ID NO 320
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(5)
<223> OTHER INFORMATION: locked nucleic acid
<220> FEATURE:
<221> NAME/KEY: misc_feature
```

-continued

```
<222> LOCATION: (11)..(12)
<223> OTHER INFORMATION: locked nucleic acid

<400> SEQUENCE: 320
tccagaatta gaga                                                14

<210> SEQ ID NO 321
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (12)..(12)
<223> OTHER INFORMATION: locked nucleic acid
<220> FEATURE:
<221> NAME/KEY: misc_feature
<222> LOCATION: (15)..(15)
<223> OTHER INFORMATION: locked nucleic acid

<400> SEQUENCE: 321
ataaactaat acagagttgt                                          20

<210> SEQ ID NO 322
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (14)..(14)
<223> OTHER INFORMATION: locked nucleic acid

<400> SEQUENCE: 322
tgtctacgtt tttctgc                                             17

<210> SEQ ID NO 323
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(5)
<223> OTHER INFORMATION: locked nucleic acid
<220> FEATURE:
<221> NAME/KEY: misc_feature
<222> LOCATION: (8)..(10)
<223> OTHER INFORMATION: locked nucleic acid

<400> SEQUENCE: 323
aaccattgaa ccc                                                 13

<210> SEQ ID NO 324
<211> LENGTH: 24
<212> TYPE: DNA
<213> ORGANISM: Artificial Sequence
<220> FEATURE:
<223> OTHER INFORMATION: Synthetic Construct

<400> SEQUENCE: 324
ttgttaataa ggtgcctgcg gtgc                                     24
```

-continued

```
<210> SEQ ID NO 325
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid

<400> SEQUENCE: 325
ttaaggacaa acgaagat                                                         18

<210> SEQ ID NO 326
<211> LENGTH: 17
<212> TYPE: DNA
<213> ORGANISM: Artificial Sequence
<220> FEATURE:
<223> OTHER INFORMATION: Synthetic Construct

<400> SEQUENCE: 326
aagtctttct tgccgtg                                                          17

<210> SEQ ID NO 327
<211> LENGTH: 26
<212> TYPE: DNA
<213> ORGANISM: Artificial Sequence
<220> FEATURE:
<223> OTHER INFORMATION: Synthetic Construct

<400> SEQUENCE: 327
tggacagtac cgagggcagt gtaata                                                26

<210> SEQ ID NO 328
<211> LENGTH: 22
<212> TYPE: DNA
<213> ORGANISM: Artificial Sequence
<220> FEATURE:
<223> OTHER INFORMATION: Synthetic Construct

<400> SEQUENCE: 328
tagctggaca gtaccgaggg ca                                                    22

<210> SEQ ID NO 329
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: locked nucleic acid
<220> FEATURE:
<221> NAME/KEY: misc_feature
<222> LOCATION: (13)..(13)
<223> OTHER INFORMATION: locked nucleic acid

<400> SEQUENCE: 329
tcagaatgaa ttagatcctg                                                       20

<210> SEQ ID NO 330
<211> LENGTH: 18
```

-continued

```
<212> TYPE: DNA
<213> ORGANISM: Artificial Sequence
<220> FEATURE:
<223> OTHER INFORMATION: Synthetic Construct

<400> SEQUENCE: 330
tgcttcatcg ttttcctc                                                  18

<210> SEQ ID NO 331
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(7)
<223> OTHER INFORMATION: locked nucleic acid
<220> FEATURE:
<221> NAME/KEY: misc_feature
<222> LOCATION: (12)..(12)
<223> OTHER INFORMATION: locked nucleic acid

<400> SEQUENCE: 331
tgacctgttg tgt                                                       13

<210> SEQ ID NO 332
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(16)
<223> OTHER INFORMATION: locked nucleic acid

<400> SEQUENCE: 332
tagtcatgca caactacc                                                  18

<210> SEQ ID NO 333
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (17)..(17)
<223> OTHER INFORMATION: locked nucleic acid

<400> SEQUENCE: 333
tcacacttac aacatacac                                                 19

<210> SEQ ID NO 334
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (7)..(8)
<223> OTHER INFORMATION: locked nucleic acid

<400> SEQUENCE: 334
```

-continued

```
ccgacgagcc ga                                                    12

<210> SEQ ID NO 335
<211> LENGTH: 18
<212> TYPE: DNA
<213> ORGANISM: Artificial Sequence
<220> FEATURE:
<223> OTHER INFORMATION: Synthetic Construct

<400> SEQUENCE: 335
cggcagaatt gagcttac                                              18

<210> SEQ ID NO 336
<211> LENGTH: 18
<212> TYPE: DNA
<213> ORGANISM: Artificial Sequence
<220> FEATURE:
<223> OTHER INFORMATION: Synthetic Construct

<400> SEQUENCE: 336
cggcagaatt gagcttac                                              18

<210> SEQ ID NO 337
<211> LENGTH: 19
<212> TYPE: DNA
<213> ORGANISM: Artificial Sequence
<220> FEATURE:
<223> OTHER INFORMATION: Synthetic Construct

<400> SEQUENCE: 337
ggacacacaa aggacaagg                                             19

<210> SEQ ID NO 338
<211> LENGTH: 18
<212> TYPE: DNA
<213> ORGANISM: Artificial Sequence
<220> FEATURE:
<223> OTHER INFORMATION: Synthetic Construct

<400> SEQUENCE: 338
ggacacacaa aggacaag                                              18

<210> SEQ ID NO 339
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (9)..(9)
<223> OTHER INFORMATION: locked nucleic acid
<220> FEATURE:
<221> NAME/KEY: misc_feature
<222> LOCATION: (11)..(12)
<223> OTHER INFORMATION: locked nucleic acid

<400> SEQUENCE: 339
tcggcagagg acc                                                   13

<210> SEQ ID NO 340
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
```

-continued

```
<222> LOCATION: (6)..(6)
<223> OTHER INFORMATION: locked nucleic acid
<220> FEATURE:
<221> NAME/KEY: misc_feature
<222> LOCATION: (9)..(9)
<223> OTHER INFORMATION: locked nucleic acid
<220> FEATURE:
<221> NAME/KEY: misc_feature
<222> LOCATION: (11)..(12)
<223> OTHER INFORMATION: locked nucleic acid

<400> SEQUENCE: 340
tcggcagagg acc                                                    13

<210> SEQ ID NO 341
<211> LENGTH: 16
<212> TYPE: DNA
<213> ORGANISM: Artificial Sequence
<220> FEATURE:
<223> OTHER INFORMATION: Synthetic Construct

<400> SEQUENCE: 341
gggagaccga agtgaa                                                 16

<210> SEQ ID NO 342
<211> LENGTH: 16
<212> TYPE: DNA
<213> ORGANISM: Artificial Sequence
<220> FEATURE:
<223> OTHER INFORMATION: Synthetic Construct

<400> SEQUENCE: 342
tccacttacc tctggc                                                 16

<210> SEQ ID NO 343
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (6)..(6)
<223> OTHER INFORMATION: locked nucleic acid
<220> FEATURE:
<221> NAME/KEY: misc_feature
<222> LOCATION: (8)..(10)
<223> OTHER INFORMATION: locked nucleic acid

<400> SEQUENCE: 343
ctggaccaac ccg                                                    13

<210> SEQ ID NO 344
<211> LENGTH: 17
<212> TYPE: DNA
<213> ORGANISM: Artificial Sequence
<220> FEATURE:
<223> OTHER INFORMATION: Synthetic Construct

<400> SEQUENCE: 344
ctcggacagc tcctaag                                                17

<210> SEQ ID NO 345
<211> LENGTH: 16
<212> TYPE: DNA
```

-continued

```
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (9)..(9)
<223> OTHER INFORMATION: locked nucleic acid

<400> SEQUENCE: 345
acccttctac ggactc                                                   16

<210> SEQ ID NO 346
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (9)..(10)
<223> OTHER INFORMATION: locked nucleic acid
<220> FEATURE:
<221> NAME/KEY: misc_feature
<222> LOCATION: (12)..(12)
<223> OTHER INFORMATION: locked nucleic acid

<400> SEQUENCE: 346
cgcccagtcc tac                                                      13

<210> SEQ ID NO 347
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (13)..(13)
<223> OTHER INFORMATION: locked nucleic acid

<400> SEQUENCE: 347
tctcttagag agtggct                                                  17

<210> SEQ ID NO 348
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: locked nucleic acid
<220> FEATURE:
<221> NAME/KEY: misc_feature
<222> LOCATION: (11)..(11)
<223> OTHER INFORMATION: locked nucleic acid
<220> FEATURE:
<221> NAME/KEY: misc_feature
<222> LOCATION: (16)..(16)
<223> OTHER INFORMATION: locked nucleic acid

<400> SEQUENCE: 348
ttcttctatg tagacaga                                                 18

<210> SEQ ID NO 349
<211> LENGTH: 13
```

```
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: locked nucleic acid
<220> FEATURE:
<221> NAME/KEY: misc_feature
<222> LOCATION: (8)..(11)
<223> OTHER INFORMATION: locked nucleic acid

<400> SEQUENCE: 349
cgcattagag acc                                                        13

<210> SEQ ID NO 350
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid
<220> FEATURE:
<221> NAME/KEY: misc_feature
<222> LOCATION: (13)..(13)
<223> OTHER INFORMATION: locked nucleic acid

<400> SEQUENCE: 350
tgcctacatt ctatcttg                                                   18

<210> SEQ ID NO 351
<211> LENGTH: 17
<212> TYPE: DNA
<213> ORGANISM: Artificial Sequence
<220> FEATURE:
<223> OTHER INFORMATION: Synthetic Construct

<400> SEQUENCE: 351
acgggtttcc aagacta                                                    17

<210> SEQ ID NO 352
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(5)
<223> OTHER INFORMATION: locked nucleic acid
<220> FEATURE:
<221> NAME/KEY: misc_feature
<222> LOCATION: (9)..(10)
<223> OTHER INFORMATION: locked nucleic acid
<220> FEATURE:
<221> NAME/KEY: misc_feature
<222> LOCATION: (12)..(12)
<223> OTHER INFORMATION: locked nucleic acid

<400> SEQUENCE: 352
tatgtttgtc ccc                                                        13

<210> SEQ ID NO 353
```

-continued

```
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (12)..(12)
<223> OTHER INFORMATION: locked nucleic acid

<400> SEQUENCE: 353
cactctcagt aattccct                                              18

<210> SEQ ID NO 354
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: locked nucleic acid
<220> FEATURE:
<221> NAME/KEY: misc_feature
<222> LOCATION: (9)..(9)
<223> OTHER INFORMATION: locked nucleic acid
<220> FEATURE:
<221> NAME/KEY: misc_feature
<222> LOCATION: (17)..(17)
<223> OTHER INFORMATION: locked nucleic acid

<400> SEQUENCE: 354
caaagattgt tagtggaat                                             19

<210> SEQ ID NO 355
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: locked nucleic acid
<220> FEATURE:
<221> NAME/KEY: misc_feature
<222> LOCATION: (7)..(7)
<223> OTHER INFORMATION: locked nucleic acid
<220> FEATURE:
<221> NAME/KEY: misc_feature
<222> LOCATION: (9)..(10)
<223> OTHER INFORMATION: locked nucleic acid
<220> FEATURE:
<221> NAME/KEY: misc_feature
<222> LOCATION: (12)..(12)
<223> OTHER INFORMATION: locked nucleic acid

<400> SEQUENCE: 355
tccctaccag gaa                                                   13

<210> SEQ ID NO 356
<211> LENGTH: 17
<212> TYPE: DNA
<213> ORGANISM: Artificial Sequence
<220> FEATURE:
<223> OTHER INFORMATION: Synthetic Construct

<400> SEQUENCE: 356
ccgctaggat atgacgt                                               17
```

-continued

```
<210> SEQ ID NO 357
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (10)..(10)
<223> OTHER INFORMATION: locked nucleic acid
<220> FEATURE:
<221> NAME/KEY: misc_feature
<222> LOCATION: (15)..(17)
<223> OTHER INFORMATION: locked nucleic acid

<400> SEQUENCE: 357
ttacaatata attagcca                                                      18

<210> SEQ ID NO 358
<211> LENGTH: 26
<212> TYPE: DNA
<213> ORGANISM: Artificial Sequence
<220> FEATURE:
<223> OTHER INFORMATION: Synthetic Construct

<400> SEQUENCE: 358
acctctagca tctgctatgc gaatgc                                             26

<210> SEQ ID NO 359
<211> LENGTH: 16
<212> TYPE: DNA
<213> ORGANISM: Artificial Sequence
<220> FEATURE:
<223> OTHER INFORMATION: Synthetic Construct

<400> SEQUENCE: 359
gcttacccct ccacaa                                                        16

<210> SEQ ID NO 360
<211> LENGTH: 16
<212> TYPE: DNA
<213> ORGANISM: Artificial Sequence
<220> FEATURE:
<223> OTHER INFORMATION: Synthetic Construct

<400> SEQUENCE: 360
ggcaccgtta gtgttg                                                        16

<210> SEQ ID NO 361
<211> LENGTH: 21
<212> TYPE: DNA
<213> ORGANISM: Artificial Sequence
<220> FEATURE:
<223> OTHER INFORMATION: Synthetic Construct

<400> SEQUENCE: 361
tacccctcct acccctctgc c                                                  21

<210> SEQ ID NO 362
<211> LENGTH: 17
<212> TYPE: DNA
<213> ORGANISM: Artificial Sequence
<220> FEATURE:
<223> OTHER INFORMATION: Synthetic Construct

<400> SEQUENCE: 362
taccgaactt caaccca                                                       17
```

-continued

```
<210> SEQ ID NO 363
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: locked nucleic acid

<400> SEQUENCE: 363
ttgatgagta agagggtg                                                    18

<210> SEQ ID NO 364
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (10)..(12)
<223> OTHER INFORMATION: locked nucleic acid

<400> SEQUENCE: 364
ccatcaccac cac                                                         13

<210> SEQ ID NO 365
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(5)
<223> OTHER INFORMATION: locked nucleic acid
<220> FEATURE:
<221> NAME/KEY: misc_feature
<222> LOCATION: (8)..(8)
<223> OTHER INFORMATION: locked nucleic acid

<400> SEQUENCE: 365
tgccagacca atc                                                         13

<210> SEQ ID NO 366
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (10)..(10)
<223> OTHER INFORMATION: locked nucleic acid

<400> SEQUENCE: 366
agcaccccaa atgatc                                                      16

<210> SEQ ID NO 367
<211> LENGTH: 17
```

-continued

```
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: locked nucleic acid

<400> SEQUENCE: 367
taatggcata ggtggaa                                               17

<210> SEQ ID NO 368
<211> LENGTH: 19
<212> TYPE: DNA
<213> ORGANISM: Artificial Sequence
<220> FEATURE:
<223> OTHER INFORMATION: Synthetic Construct

<400> SEQUENCE: 368
tccagaacca cggtccccg                                             19

<210> SEQ ID NO 369
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(16)
<223> OTHER INFORMATION: locked nucleic acid

<400> SEQUENCE: 369
atcaacgacc aacaattac                                             19

<210> SEQ ID NO 370
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (17)..(17)
<223> OTHER INFORMATION: locked nucleic acid

<400> SEQUENCE: 370
ttgagtctta gagggttg                                              18

<210> SEQ ID NO 371
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: locked nucleic acid
<220> FEATURE:
<221> NAME/KEY: misc_feature
<222> LOCATION: (7)..(7)
<223> OTHER INFORMATION: locked nucleic acid
<220> FEATURE:
<221> NAME/KEY: misc_feature
<222> LOCATION: (10)..(10)
<223> OTHER INFORMATION: locked nucleic acid
<220> FEATURE:
<221> NAME/KEY: misc_feature
<222> LOCATION: (12)..(12)
```

-continued

```
<223> OTHER INFORMATION: locked nucleic acid
<220> FEATURE:
<221> NAME/KEY: misc_feature
<222> LOCATION: (15)..(15)
<223> OTHER INFORMATION: locked nucleic acid

<400> SEQUENCE: 371
cccgagggta gat                                                        13

<210> SEQ ID NO 372
<211> LENGTH: 15
<212> TYPE: DNA
<213> ORGANISM: Artificial Sequence
<220> FEATURE:
<223> OTHER INFORMATION: Synthetic Construct

<400> SEQUENCE: 372
ttggagacca gagcc                                                      15

<210> SEQ ID NO 373
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(16)
<223> OTHER INFORMATION: locked nucleic acid

<400> SEQUENCE: 373
ttgtccctga tgaagac                                                    17

<210> SEQ ID NO 374
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(5)
<223> OTHER INFORMATION: locked nucleic acid
<220> FEATURE:
<221> NAME/KEY: misc_feature
<222> LOCATION: (8)..(9)
<223> OTHER INFORMATION: locked nucleic acid
<220> FEATURE:
<221> NAME/KEY: misc_feature
<222> LOCATION: (12)..(12)
<223> OTHER INFORMATION: locked nucleic acid

<400> SEQUENCE: 374
gcctgaacta agt                                                        13

<210> SEQ ID NO 375
<211> LENGTH: 16
<212> TYPE: DNA
<213> ORGANISM: Artificial Sequence
<220> FEATURE:
<223> OTHER INFORMATION: Synthetic Construct

<400> SEQUENCE: 375
actcaccaac tcctgg                                                     16

<210> SEQ ID NO 376
<211> LENGTH: 19
<212> TYPE: DNA
<213> ORGANISM: Artificial Sequence
```

-continued

```
<220> FEATURE:
<223> OTHER INFORMATION: Synthetic Construct
<220> FEATURE:
<221> NAME/KEY: misc_feature
<222> LOCATION: (12)..(12)
<223> OTHER INFORMATION: locked nucleic acid

<400> SEQUENCE: 376
ttcatgtatt ggtgaaacg                                              19

<210> SEQ ID NO 377
<211> LENGTH: 21
<212> TYPE: DNA
<213> ORGANISM: Artificial Sequence
<220> FEATURE:
<223> OTHER INFORMATION: Synthetic Construct

<400> SEQUENCE: 377
caatgccgcc cccgtttgta g                                           21

<210> SEQ ID NO 378
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (13)..(13)
<223> OTHER INFORMATION: locked nucleic acid

<400> SEQUENCE: 378
cggagtccca taatagc                                                17

<210> SEQ ID NO 379
<211> LENGTH: 17
<212> TYPE: DNA
<213> ORGANISM: Artificial Sequence
<220> FEATURE:
<223> OTHER INFORMATION: Synthetic Construct

<400> SEQUENCE: 379
gtctgcgggg tctatag                                                17

<210> SEQ ID NO 380
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(4)
<223> OTHER INFORMATION: locked nucleic acid
<220> FEATURE:
<221> NAME/KEY: misc_feature
<222> LOCATION: (6)..(8)
<223> OTHER INFORMATION: locked nucleic acid

<400> SEQUENCE: 380
cagaggctcc cat                                                    13

<210> SEQ ID NO 381
<211> LENGTH: 18
<212> TYPE: DNA
<213> ORGANISM: Artificial Sequence
<220> FEATURE:
<223> OTHER INFORMATION: Synthetic Construct
<220> FEATURE:
```

-continued

```
<221> NAME/KEY: misc_feature
<222> LOCATION: (9)..(9)
<223> OTHER INFORMATION: locked nucleic acid
<220> FEATURE:
<221> NAME/KEY: misc_feature
<222> LOCATION: (14)..(14)
<223> OTHER INFORMATION: locked nucleic acid

<400> SEQUENCE: 381
aaagttggga ttacattt                                              18

<210> SEQ ID NO 382
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (14)..(14)
<223> OTHER INFORMATION: locked nucleic acid

<400> SEQUENCE: 382
ggcgaggtct tttactg                                               17

<210> SEQ ID NO 383
<211> LENGTH: 30
<212> TYPE: DNA
<213> ORGANISM: Artificial Sequence
<220> FEATURE:
<223> OTHER INFORMATION: Synthetic Construct

<400> SEQUENCE: 383
tgagacaaca gaatctccta gctcagatga                                 30

<210> SEQ ID NO 384
<211> LENGTH: 19
<212> TYPE: DNA
<213> ORGANISM: Artificial Sequence
<220> FEATURE:
<223> OTHER INFORMATION: Synthetic Construct

<400> SEQUENCE: 384
taggcccact taacactac                                             19

<210> SEQ ID NO 385
<211> LENGTH: 18
<212> TYPE: DNA
<213> ORGANISM: Artificial Sequence
<220> FEATURE:
<223> OTHER INFORMATION: Synthetic Construct

<400> SEQUENCE: 385
ggaggccctt agacttac                                              18

<210> SEQ ID NO 386
<211> LENGTH: 27
<212> TYPE: DNA
<213> ORGANISM: Artificial Sequence
<220> FEATURE:
<223> OTHER INFORMATION: Synthetic Construct

<400> SEQUENCE: 386
cgcctctcca ttcatcatgt aacccac                                    27

<210> SEQ ID NO 387
<211> LENGTH: 21
```

-continued

```
<212> TYPE: DNA
<213> ORGANISM: Artificial Sequence
<220> FEATURE:
<223> OTHER INFORMATION: Synthetic Construct

<400> SEQUENCE: 387
atccctagga taataccaca c                                                  21

<210> SEQ ID NO 388
<211> LENGTH: 17
<212> TYPE: DNA
<213> ORGANISM: Artificial Sequence
<220> FEATURE:
<223> OTHER INFORMATION: Synthetic Construct

<400> SEQUENCE: 388
cacgtaaagc cacaagc                                                       17

<210> SEQ ID NO 389
<211> LENGTH: 27
<212> TYPE: DNA
<213> ORGANISM: Artificial Sequence
<220> FEATURE:
<223> OTHER INFORMATION: Synthetic Construct

<400> SEQUENCE: 389
agcagtgtag tcctgtcaat ctcctga                                            27

<210> SEQ ID NO 390
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (13)..(13)
<223> OTHER INFORMATION: locked nucleic acid

<400> SEQUENCE: 390
ctcctaagaa ggcacc                                                        16

<210> SEQ ID NO 391
<211> LENGTH: 17
<212> TYPE: DNA
<213> ORGANISM: Artificial Sequence
<220> FEATURE:
<223> OTHER INFORMATION: Synthetic Construct

<400> SEQUENCE: 391
ctcctcttct tgctgga                                                       17

<210> SEQ ID NO 392
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(5)
<223> OTHER INFORMATION: locked nucleic acid
<220> FEATURE:
<221> NAME/KEY: misc_feature
<222> LOCATION: (8)..(8)
<223> OTHER INFORMATION: locked nucleic acid
<220> FEATURE:
<221> NAME/KEY: misc_feature
<222> LOCATION: (12)..(12)
```

-continued

<223> OTHER INFORMATION: locked nucleic acid

<400> SEQUENCE: 392
caagaaccca gac                                                          13

<210> SEQ ID NO 393
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: locked nucleic acid
<220> FEATURE:
<221> NAME/KEY: misc_feature
<222> LOCATION: (11)..(11)
<223> OTHER INFORMATION: locked nucleic acid
<220> FEATURE:
<221> NAME/KEY: misc_feature
<222> LOCATION: (16)..(16)
<223> OTHER INFORMATION: locked nucleic acid

<400> SEQUENCE: 393
attagagacc actttgag                                                     18

<210> SEQ ID NO 394
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: locked nucleic acid
<220> FEATURE:
<221> NAME/KEY: misc_feature
<222> LOCATION: (17)..(17)
<223> OTHER INFORMATION: locked nucleic acid

<400> SEQUENCE: 394
ttagtcttca tcctcttct                                                    19

<210> SEQ ID NO 395
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (8)..(11)
<223> OTHER INFORMATION: locked nucleic acid

<400> SEQUENCE: 395
cgccaatctg tct                                                          13

<210> SEQ ID NO 396
<211> LENGTH: 19
<212> TYPE: DNA
<213> ORGANISM: Artificial Sequence -continued

```
<220> FEATURE:
<223> OTHER INFORMATION: Synthetic Construct
<220> FEATURE:
<221> NAME/KEY: misc_feature
<222> LOCATION: (16)..(16)
<223> OTHER INFORMATION: locked nucleic acid

<400> SEQUENCE: 396
tctaattgtt gacacggat                                                  19

<210> SEQ ID NO 397
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: locked nucleic acid

<400> SEQUENCE: 397
tgtctgacag ttgttcc                                                    17

<210> SEQ ID NO 398
<211> LENGTH: 29
<212> TYPE: DNA
<213> ORGANISM: Artificial Sequence
<220> FEATURE:
<223> OTHER INFORMATION: Synthetic Construct

<400> SEQUENCE: 398
cttggaaacc cgtcactctc agtaattcc                                       29

<210> SEQ ID NO 399
<211> LENGTH: 19
<212> TYPE: DNA
<213> ORGANISM: Artificial Sequence
<220> FEATURE:
<223> OTHER INFORMATION: Synthetic Construct

<400> SEQUENCE: 399
tcacctcttg atagggatc                                                  19

<210> SEQ ID NO 400
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (17)..(17)
<223> OTHER INFORMATION: locked nucleic acid

<400> SEQUENCE: 400
attagccatc caaagcat                                                   18

<210> SEQ ID NO 401
<211> LENGTH: 22
<212> TYPE: DNA
<213> ORGANISM: Artificial Sequence
<220> FEATURE:
<223> OTHER INFORMATION: Synthetic Construct

<400> SEQUENCE: 401
cgggcatgga cctctagcat ct                                              22
```

```
<210> SEQ ID NO 402
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (7)..(7)
<223> OTHER INFORMATION: locked nucleic acid
<220> FEATURE:
<221> NAME/KEY: misc_feature
<222> LOCATION: (12)..(12)
<223> OTHER INFORMATION: locked nucleic acid
<220> FEATURE:
<221> NAME/KEY: misc_feature
<222> LOCATION: (14)..(15)
<223> OTHER INFORMATION: locked nucleic acid

<400> SEQUENCE: 402
atattgtaag acaatcac                                                                         18

<210> SEQ ID NO 403
<211> LENGTH: 15
<212> TYPE: DNA
<213> ORGANISM: Artificial Sequence
<220> FEATURE:
<223> OTHER INFORMATION: Synthetic Construct

<400> SEQUENCE: 403
atgtggctgg accaa                                                                            15

<210> SEQ ID NO 404
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: locked nucleic acid
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (7)..(7)
<223> OTHER INFORMATION: locked nucleic acid
<220> FEATURE:
<221> NAME/KEY: misc_feature
<222> LOCATION: (11)..(11)
<223> OTHER INFORMATION: locked nucleic acid

<400> SEQUENCE: 404
cctgaggggc tgt                                                                              13

<210> SEQ ID NO 405
<211> LENGTH: 15
<212> TYPE: DNA
<213> ORGANISM: Artificial Sequence
<220> FEATURE:
<223> OTHER INFORMATION: Synthetic Construct

<400> SEQUENCE: 405
ctctacgccc gacag                                                                            15

<210> SEQ ID NO 406
<211> LENGTH: 16
```

-continued

```
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (12)..(12)
<223> OTHER INFORMATION: locked nucleic acid

<400> SEQUENCE: 406
ttggtggcat catgag                                                             16

<210> SEQ ID NO 407
<211> LENGTH: 23
<212> TYPE: DNA
<213> ORGANISM: Artificial Sequence
<220> FEATURE:
<223> OTHER INFORMATION: Synthetic Construct

<400> SEQUENCE: 407
tgtcacctct gtcacaaccg agg                                                     23

<210> SEQ ID NO 408
<211> LENGTH: 16
<212> TYPE: DNA
<213> ORGANISM: Artificial Sequence
<220> FEATURE:
<223> OTHER INFORMATION: Synthetic Construct

<400> SEQUENCE: 408
acccacacca ctactc                                                             16

<210> SEQ ID NO 409
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(16)
<223> OTHER INFORMATION: locked nucleic acid

<400> SEQUENCE: 409
tctggcacat gcaaga                                                             16

<210> SEQ ID NO 410
<211> LENGTH: 26
<212> TYPE: DNA
<213> ORGANISM: Artificial Sequence
<220> FEATURE:
<223> OTHER INFORMATION: Synthetic Construct

<400> SEQUENCE: 410
taccgaactt caacccacac catcac                                                  26

<210> SEQ ID NO 411
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(16)
<223> OTHER INFORMATION: locked nucleic acid

<400> SEQUENCE: 411
```
aatcaatgca ccctctta                                                    18

<210> SEQ ID NO 412
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: locked nucleic acid
<220> FEATURE:
<221> NAME/KEY: misc_feature
<222> LOCATION: (18)..(19)
<223> OTHER INFORMATION: locked nucleic acid

<400> SEQUENCE: 412
aatgttataa aatacagtcg                                                  20

<210> SEQ ID NO 413
<211> LENGTH: 26
<212> TYPE: DNA
<213> ORGANISM: Artificial Sequence
<220> FEATURE:
<223> OTHER INFORMATION: Synthetic Construct

<400> SEQUENCE: 413
tgatccagat agtccagaac cacggt                                           26

<210> SEQ ID NO 414
<211> LENGTH: 17
<212> TYPE: DNA
<213> ORGANISM: Artificial Sequence
<220> FEATURE:
<223> OTHER INFORMATION: Synthetic Construct

<400> SEQUENCE: 414
attacccccc tcacaat                                                     17

<210> SEQ ID NO 415
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (9)..(9)
<223> OTHER INFORMATION: locked nucleic acid
<220> FEATURE:
<221> NAME/KEY: misc_feature
<222> LOCATION: (18)..(18)
<223> OTHER INFORMATION: locked nucleic acid

<400> SEQUENCE: 415
tagatgatgt aattgttggt                                                  20

<210> SEQ ID NO 416
<211> LENGTH: 19
<212> TYPE: DNA
<213> ORGANISM: Artificial Sequence
<220> FEATURE:
<223> OTHER INFORMATION: Synthetic Construct

<400> SEQUENCE: 416
caccaccagc agcaccagc                                                   19

```
<210> SEQ ID NO 417
<211> LENGTH: 15
<212> TYPE: DNA
<213> ORGANISM: Artificial Sequence
<220> FEATURE:
<223> OTHER INFORMATION: Synthetic Construct

<400> SEQUENCE: 417
acaagcaacg caagc                                              15

<210> SEQ ID NO 418
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (11)..(11)
<223> OTHER INFORMATION: locked nucleic acid

<400> SEQUENCE: 418
aggactggac ttagttca                                           18

<210> SEQ ID NO 419
<211> LENGTH: 23
<212> TYPE: DNA
<213> ORGANISM: Artificial Sequence
<220> FEATURE:
<223> OTHER INFORMATION: Synthetic Construct

<400> SEQUENCE: 419
accttggaga ccagagccaa aca                                     23

<210> SEQ ID NO 420
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: locked nucleic acid
<220> FEATURE:
<221> NAME/KEY: misc_feature
<222> LOCATION: (14)..(14)
<223> OTHER INFORMATION: locked nucleic acid

<400> SEQUENCE: 420
cgtttgtaga aattcacac                                          19

<210> SEQ ID NO 421
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (12)..(12)
<223> OTHER INFORMATION: locked nucleic acid

<400> SEQUENCE: 421
tctgggctat tatggga                                            17

<210> SEQ ID NO 422
<211> LENGTH: 14
<212> TYPE: DNA
```

-continued

```
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(6)
<223> OTHER INFORMATION: locked nucleic acid
<220> FEATURE:
<221> NAME/KEY: misc_feature
<222> LOCATION: (10)..(11)
<223> OTHER INFORMATION: locked nucleic acid

<400> SEQUENCE: 422
tcaccaatac atga                                                    14

<210> SEQ ID NO 423
<211> LENGTH: 17
<212> TYPE: DNA
<213> ORGANISM: Artificial Sequence
<220> FEATURE:
<223> OTHER INFORMATION: Synthetic Construct

<400> SEQUENCE: 423
ccattctctt ccccgat                                                 17

<210> SEQ ID NO 424
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (9)..(9)
<223> OTHER INFORMATION: locked nucleic acid
<220> FEATURE:
<221> NAME/KEY: misc_feature
<222> LOCATION: (15)..(15)
<223> OTHER INFORMATION: locked nucleic acid

<400> SEQUENCE: 424
aaatgtaatc ccaacttt                                                18

<210> SEQ ID NO 425
<211> LENGTH: 13
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(6)
<223> OTHER INFORMATION: locked nucleic acid
<220> FEATURE:
<221> NAME/KEY: misc_feature
<222> LOCATION: (13)..(13)
<223> OTHER INFORMATION: locked nucleic acid
<220> FEATURE:
<221> NAME/KEY: misc_feature
<222> LOCATION: (15)..(15)
<223> OTHER INFORMATION: locked nucleic acid

<400> SEQUENCE: 425
ccgcagactt aga                                                     13
```